United States Patent [19]

Fariss

[11] Patent Number: 5,610,180

[45] Date of Patent: *Mar. 11, 1997

[54] IONIZABLE CONGENERS OF AROMATIC AND ALIPHATIC ALCOHOLS AS ANTI-LEUKEMIA AGENTS

[75] Inventor: Marc W. Fariss, Manakin-Sabot, Va.

[73] Assignee: Virginia Commonwealth University, Richmond, Va.

[*] Notice: The term of this patent shall not extend beyond the expiration date of Pat. No. 5,336,485.

[21] Appl. No.: 286,994

[22] Filed: Aug. 8, 1994

Related U.S. Application Data

[63] Continuation-in-part of Ser. No. 28,831, Mar. 10, 1993, Pat. No. 5,336,485, which is a continuation of Ser. No. 678,110, Apr. 1, 1991, Pat. No. 5,198,432, which is a continuation-in-part of Ser. No. 316,789, Feb. 28, 1989, abandoned, which is a continuation-in-part of Ser. No. 149,762, Jan. 29, 1988, abandoned.

[51] Int. Cl.⁶ .......................... A61K 31/355; A61K 31/56
[52] U.S. Cl. ................................. 514/458; 514/182
[58] Field of Search ........................... 514/182, 458

[56] References Cited

PUBLICATIONS

Prasad et al., "Biological rationale of using alph–tocopherol (vitamin E) in the treatment of cancer" (1983) see abstract enclosed.

Primary Examiner—Kevin E. Weddington
Attorney, Agent, or Firm—Whitham, Curtis, Whitham & McGinn

[57] ABSTRACT

Ionizable congeners of aromatic and aliphatic alcohols provide potent cytoprotective properties in vivo and in vitro. Alpha-tocopherol succinate, cholesteryl succinate, cholesteryl sulfate, dihydrocholesterol succinate, dihydrocholesterol sulfate, and ergosterol analogs are particularly good cytoprotective agents. In addition, the tris salts of these compounds have superior cytoprotective properties.

11 Claims, 29 Drawing Sheets

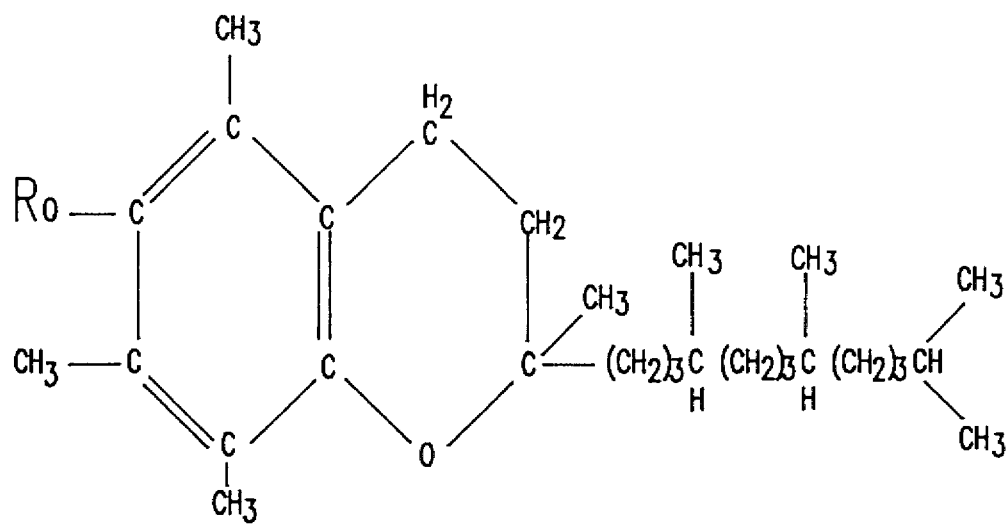

| | ANALOG | CYTOPROTECTION | IONIZABLE ESTER (R GROUP) |
|---|---|---|---|
| $R = -\overset{O}{\underset{OH}{\overset{\|}{P}}}-OH$ | d,α –Tocopheryl phosphate | ++ | Yes |
| $R = -\overset{O}{\overset{\|}{C}}-(\overset{H}{\underset{H}{C}})_3-\overset{O}{\overset{\|}{C}}-OH$ | d,α – Tocopheryl glutarate | +++ | Yes |
| $R = -\overset{O}{\overset{\|}{C}}-(\overset{H}{\underset{H}{C}})-\overset{O}{\overset{\|}{C}}-(O-\overset{H}{\underset{H}{C}}-\overset{H}{\underset{H}{C}})_n-OH$ | d,α – Tocopheryl succinate, polyethylene glycol ester | +++ | Yes (only after hydrolysis by esterases) |
| $R = -\overset{O}{\overset{\|}{C}}-\overset{H}{\underset{H}{C}}-\overset{H}{\underset{CH_3}{C}}-\overset{O}{\overset{\|}{C}}-OH$ | d,α – Tocopheryl 3-methyl succinate | +++ | Yes |
| $R = -\overset{O}{\overset{\|}{C}}-(\overset{H}{\underset{H}{C}})_2-\overset{O}{\overset{\|}{C}}-OH$ | d,α – Tocopheryl succinate | ++++ | Yes |

FIG.4A

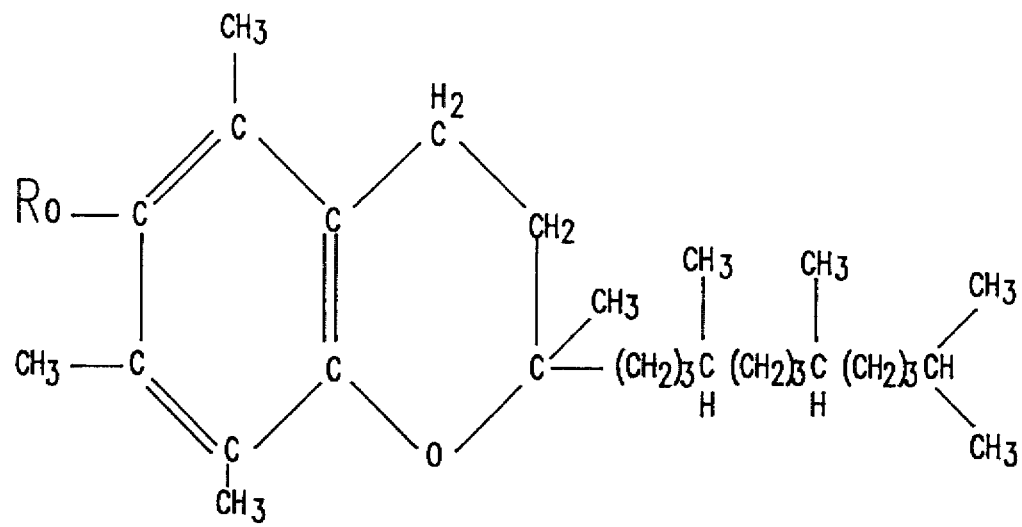

| | ANALOG | CYTOPROTECTION | IONIZABLE ESTER (R GROUP) |
|---|---|---|---|
| R = −C(=O)−CH₃ | d,α− Tocopheryl acetate | − | No |
| R = − H | d,α − Tocopherol | − | untestified |
| R = −C(=O)(CH)₂−C(=O)−NH₂ (with H) | d,α − Tocopheryl succinamide | +− | Yes (only after deamination by esterases) |
| R = −C(=O)(CH)₂−C(=O)−O−CH₃ (with H) | d,α − Tocopheryl succinate, methyl ester | ++ | Yes (only after demethylation by esterases) |
| 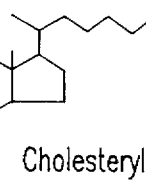 | Cholesteryl succinate | ++ | Yes |

FIG.4B

| | ANALOG | CYTOPROTECTION | IONIZABLE ESTER (R GROUP) |
|---|---|---|---|
| R = −C(=O)−CH₃ | d,α− Tocopheryl acetate | − | No |
| R = −H | d,α − Tocopheryl | − | unesterfied |
| R = −P(=O)(OH)−OH | d,α − Tocopheryl phosphate | − | Yes |
| R = −C(=O)−(CH)₃−C(=O)−OH | d,α − Tocopheryl glutarate | − | Yes |
| R = −C(=O)−CH₂−CH(CH₃)−C(=O)−OH | d,α− Tocopheryl 3−methyl succinate | − | Yes |

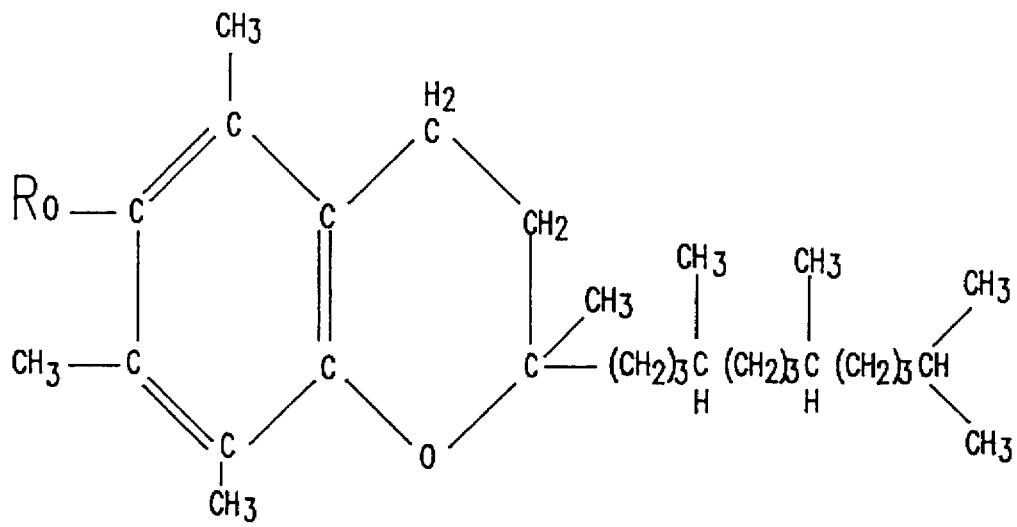
| | ANALOG | CYTOPROTECTION | IONIZABLE ESTER (R GROUP) |
|---|---|---|---|
| 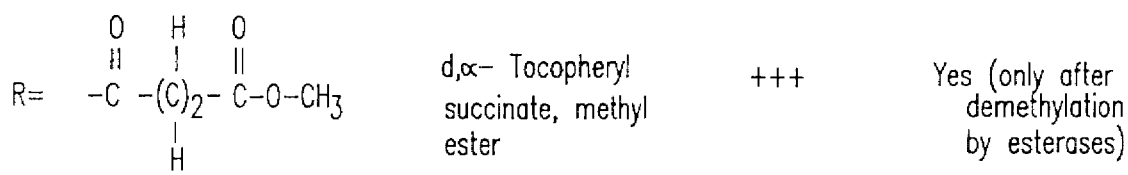 | d,α– Tocopheryl succinate, methyl ester | +++ | Yes (only after demethylation by esterases) |
| 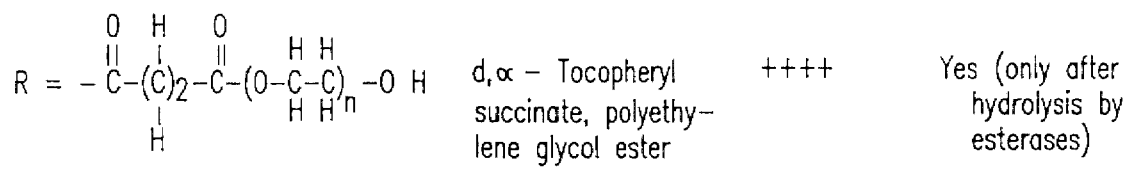 | d,α – Tocopheryl succinate, polyethylene glycol ester | ++++ | Yes (only after hydrolysis by esterases) |
| 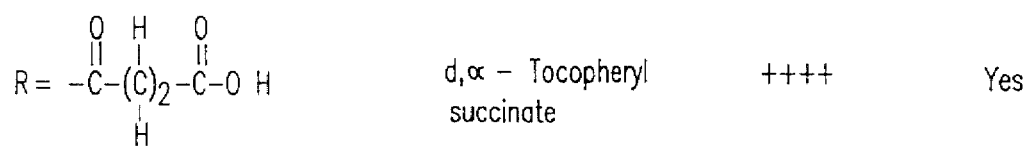 | d,α – Tocopheryl succinate | ++++ | Yes |
| 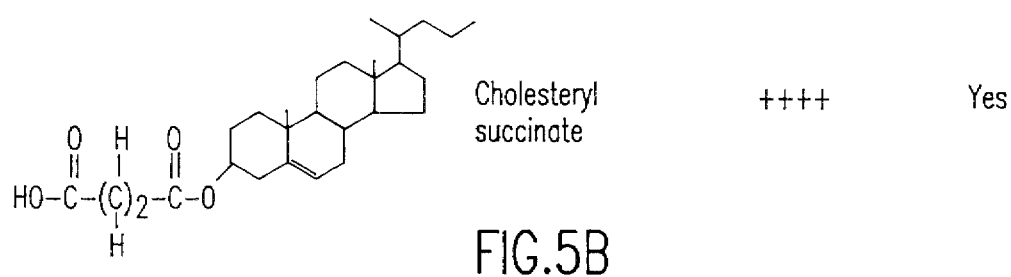 | Cholesteryl succinate | ++++ | Yes |
FIG. 5B

| R | ANALOG | CYTOPROTECTION | IONIZABLE ESTER (R Group) |
|---|---|---|---|
| -H | Cholesterol | 0 | No |
| -C(=O)-CH₃ | Cholesteryl acetate | 0 | No |
| -C(=O)-(CH)₂-C(=O)-O⁻ tris⁻ | Cholesteryl succinate tris salt | ++++ | Yes |
| -S(=O)(=O)-O⁻Na⁺ | Cholesteryl sulfate Sodium salt | +++ | Yes |
| ⁺H⁻O-C(=O)-C₆H₄-C- | Cholesteryl hydrogen phthalate | ++++ | Yes |

| R | ANALOG | CYTOPROTECTION | IONIZABLE ESTER (R Group) |
| --- | --- | --- | --- |
| -H | Dihydrocholesterol | 0 | No |
| $-\overset{O}{\underset{\|}{C}}-(CH)_2-\overset{O}{\underset{\|}{C}}-O^-tris^+$ | Dihydrocholesteryl succinate, tris salt | ++++ | Yes |
| $-\overset{O}{\underset{\underset{O}{\|}}{S}}-O^-Na^+$ | Dihydrocholesteryl Sulfate, sodium salt | ++++ | Yes |

| R | ANALOG | CYTOPROTECTION | IONIZABLE ESTER (R Group) |
| --- | --- | --- | --- |
| −H | Ergosterol | ++ | No |
| $-\overset{O}{\underset{\|}{C}}-(CH)_2-\overset{O}{\underset{\|}{C}}-O^-tris^+$ | Ergosterol succinate, tris salt | +++ | Yes |
| $-\overset{O}{\underset{\underset{O}{\|}}{\overset{\|}{S}}}-O^-K^+$ | Ergosterol Sulfate, potassium salt | +++ | Yes |

| R | ANALOG | CYTOPROTECTION | IONIZABLE ESTER (R Group) |
|---|---|---|---|
| -H | Estrone | ++ | No |
| -C(=O)-CH₃ | Estrone acetate | ++ | No |
| -C(=O)-(CH₂)₂-C(=O)-O⁻ H⁺ | Estrone succinate | ++ | Yes |
| -S(=O)(=O)-O⁻ K⁺ | Estrone sulfate potassium salt | ++ | Yes |

| R | ANALOG | CYTOPROTECTION | IONIZABLE ESTER (R Group) |
|---|---|---|---|
| -C(=O)-(CH$_2$)$_2$-C(=O)-O$^-$H$^+$ | Dehydroepiandosterone 3-succinate | 0 | Yes |
| -S(=O)(=O)-O$^-$H$^+$ | Dehydroepiandosterone 3-sulfate | 0 | Yes |

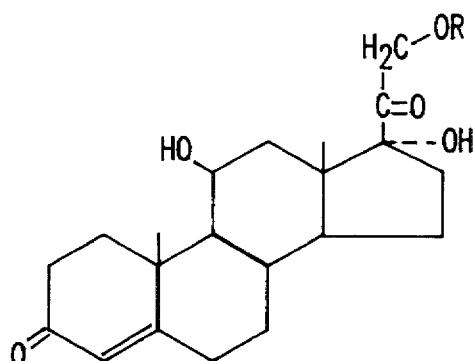
FIG.17A
| R | ANALOG | CYTOPROTECTION | IONIZABLE ESTER (R Group) |
|---|---|---|---|
| $-\overset{O}{\underset{\|}{C}}-(CH_2)_2-\overset{O}{\underset{\|}{C}}-O^-H^+$ | Hydrocortisone 21-succinate | 0 | Yes |
FIG.17B
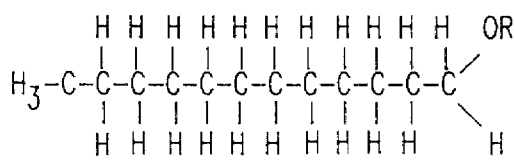
FIG.18A
| R | ANALOG | CYTOPROTECTION | IONIZABLE ESTER (R Group) |
|---|---|---|---|
| $-\overset{O}{\underset{\underset{O}{\|}}{\overset{\|}{S}}}-O^-Na^+$ | Lauryl sulfate Sodium salt | 0 | Yes |
FIG.18B

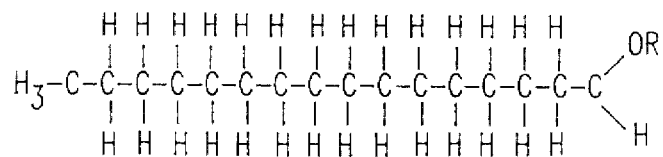
FIG.19A
| R | ANALOG | CYTOPROTECTION | IONIZABLE ESTER (R Group) |
| --- | --- | --- | --- |
| -H | Palmityl alcohol | 0 | No |
| -C(=O)-(CH$_2$)$_2$-C(=O)-O$^-$H$^+$ | Palmityl succinate | 0 | Yes |
FIG.19B
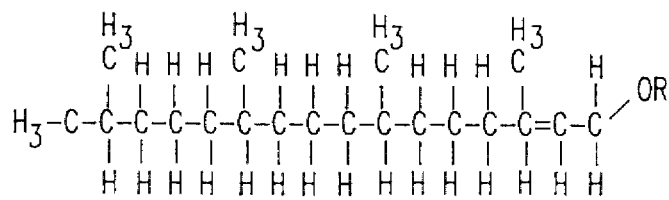
FIG.20A
| R | ANALOG | CYTOPROTECTION | IONIZABLE ESTER (R Group) |
| --- | --- | --- | --- |
| -H | Phytol | 0 | No |
| -C(=O)-(CH$_2$)$_2$-C(=O)-O$^-$H$^+$ | Phytol succinate | 0 | Yes |
FIG.20B

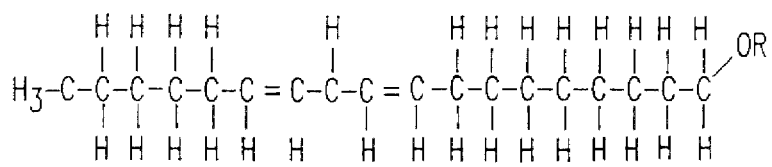
FIG.21A
| R | ANALOG | CYTOPROTECTION | IONIZABLE ESTER (R Group) |
|---|---|---|---|
| – H | Linoleyl alcohol | – (potential toxicity) | No |
| $-\overset{O}{\underset{}{C}}-(CH_2)_2-\overset{O}{\underset{}{C}}-O^-H^+$ | Linoleyl succinate | + | Yes |
FIG.21B
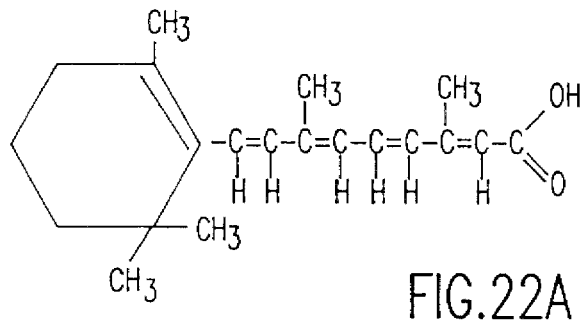
FIG.22A
RETINOIC ACID
| ANALOG | CYTOPROTECTION | IONIZABLE ESTER (R Group) |
|---|---|---|
| Retinoic acid | – (potential toxicity) | Yes |
FIG.22B

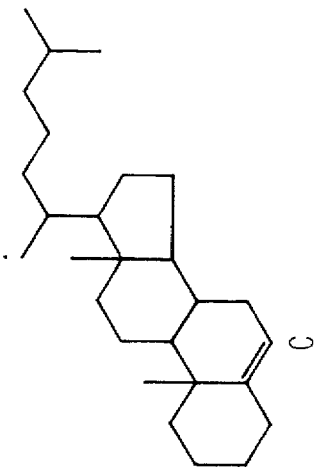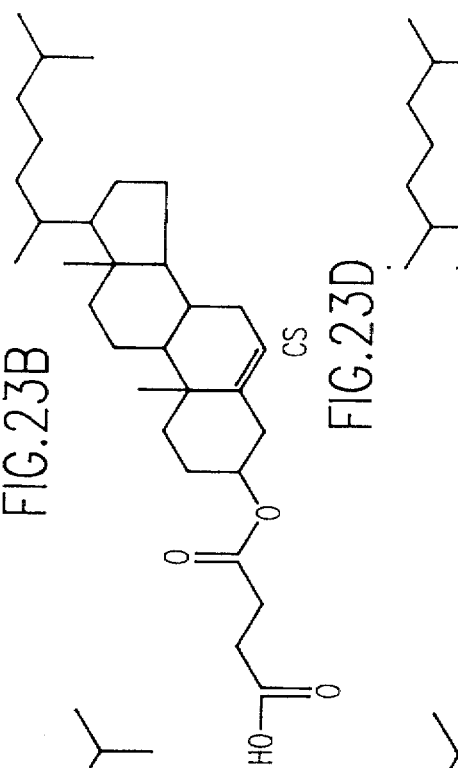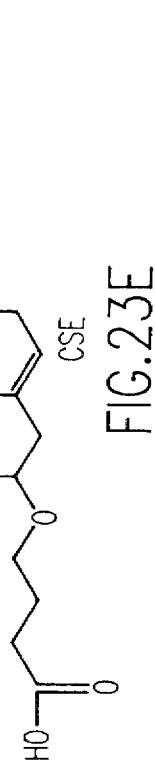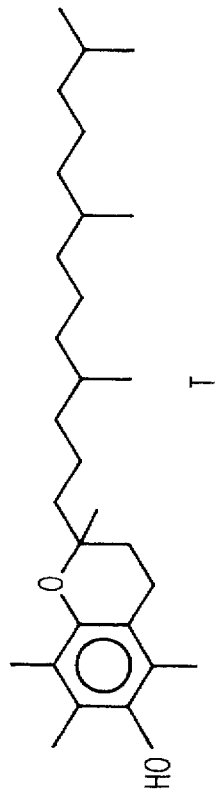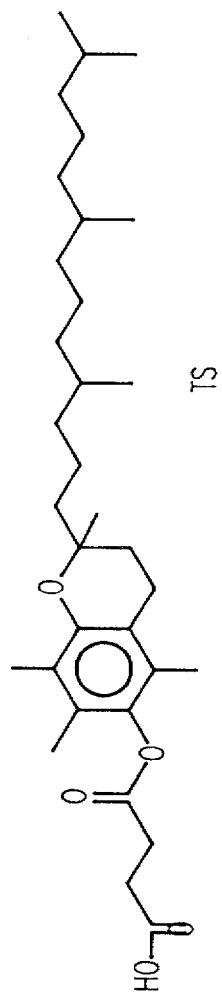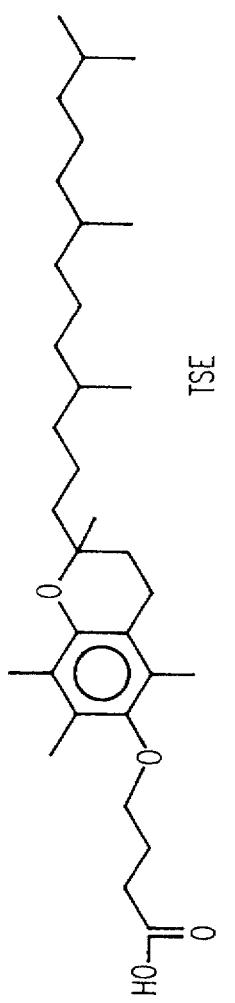
FIG.23A T
FIG.23B C
FIG.23C TS
FIG.23D CS
FIG.23E TSE
FIG.23E CSE

IONIZABLE CONGENERS OF AROMATIC AND ALIPHATIC ALCOHOLS AS ANTI-LEUKEMIA AGENTS

CROSS-REFERENCE TO RELATED APPLICATIONS

This application is a continuation-in-part (CIP) of the patent application having Ser. No. 08/028,831, filed Mar. 10, 1993, which will issue as U.S. Pat. No. 5,336,485 on Aug. 9, 1994, which itself is a continuation application of Ser. No. 07/678,110, filed Apr. 1, 1991, which issued as U.S. Pat. No. 5,198,432, and that patent is a CIP of U.S. Ser. No. 07/316,789, filed Feb. 28, 1989, now abandoned, and that application was a CIP of U.S. Ser. No. 07/149,762, filed Jan. 29, 1988, now abandoned. The complete contents of each of the patents and patent applications is herein incorporated by reference.

DESCRIPTION

BACKGROUND OF THE INVENTION

1. Field of the Invention

The subject invention generally relates to preventing cell injury and death and, more particularly, to administering ionizable congeners of aromatic and aliphatic alcohols to animals for therapeutic and prophylactic purposes including preventing carcinogenesis.

2. Description of the Prior Art

In general terms, cell injury is characterized by changes in cellular metabolic performance and alterations in cellular structure. Cell injury is assumed to be reversible upon termination of the insult or by the addition of a cytoprotective agent during the early stages; however, if the insult continues unchecked, the cell becomes non-functional and unrecoverable. Irreversible cell injury equates to cell death.

The pathological and physiological consequences of cell injury affect the functional and structural integrity of tissue and organ systems as well as the organism itself. Both endogenous and exogenous "insults" can cause cell injury. Endogenous insults are cellular factors, and they include the formation of reactive intermediates (i.e., oxygen free radicals generated during cellular electron transport processes), reduction in oxygen tension (i.e., in ischemia), and stimulation of inflammatory and immune processes. Exogenous insults are environmental factors, and they include exposure to drugs or chemicals, physical stimuli (i.e., radiation), or biological hazards (i.e., viruses).

Recent studies suggest that endogenous and exogenous insults cause cellular injury predominantly by generating reactive intermediates such as free radicals. The majority of reactive intermediates formed during cell or tissue injury are oxygen free radicals such as superoxide anion, hydroxyl free radical, or singlet oxygen and reactive oxygen containing compounds such as hydrogen peroxide. Once formed, both chemical and oxygen derived free radicals can react with a variety of cellular constituents including proteins, nucleic acids, and membrane lipids.

Cells contain endogenous protective systems to ensure viability and promote metabolic performance. For example, alpha-tocopherol is a free radical scavenger present in cellular membranes which binds free radicals in the cell. Alpha-tocopherol, which is often referred to as Vitamin E, is believed to protect against a variety of pathological processes including carcinogenesis, aging, chemical-induced toxicity, radiation-induced toxicity, ischemia-induced damage, and atherosclerosis. Alpha-tocopherol is not synthesized in mammalian cells, but rather, is derived from exogenous sources. Because unesterfied alpha-tocopherol is readily degraded when exposed to oxygen in the air, an ester derivative of alpha-tocopherol (alpha-tocopheryl acetate), is commonly used to provide a stable dosage form of alpha-tocopherol. Cellular esterases release the alpha-tocopherol in the cell by degrading the ester linkage.

The administration of succinate in high concentrations can protect cells from a variety of toxic insults. Providing the cell with additional quantities of succinate, a substrate in the tricarboxylic acid cycle, can result in energy production from oxidative phosphorylation and glycolysis which produce adenosine triphosphate (ATP) and result in glucose production from gluconeogenesis. Kondrashova et al., *Biochem. Biophys. Res. Comm.* 109:376 (1982), reported that the addition of 6 mM succinate to isolated rat liver mitochondria increased the $Ca^{2+}$ capacity and $Ca^{2+}$ retention of mitochondria five to seven fold. Cellular absorption and accumulation of succinate is limited by the polarity of the succinate molecule except in the kidney where a transport system exists. Rognstad, *Arch. Biochem. Biophys.* 230:605, (1984), has shown the cellular uptake of succinate can be advanced by administering a more lipophilic form of succinate (i.e., methyl ester of succinate). Cellular esterases will release the succinate moiety by degrading the ester linkage. Millimolar concentrations of succinate or methyl ester succinate are required to stimulate gluconeogenesis or ATP production to provide cytoprotection (See, Rognstad, *Arch. Biochem. Biophys.* 230:605 (1984) and Sanders, *Proc. Soc. Exp. Biol. Med.* 130:1021, (1969)).

SUMMARY OF THE INVENTION

It is an object of this invention to provide a method for protecting cells from cell injury and death wherein patients are provided with a therapeutic dose of ionizable congeners of aromatic and aliphatic alcohols.

It is another object of this invention to provide a method for wound healing and promoting cell recovery wherein patients are provided with a therapeutic dose of ionizable congeners of aromatic and aliphatic alcohols.

It is another object of this invention to prevent carcinogenesis wherein patients are provided with a therapeutic dose of ionizable congeners of aromatic and aliphatic alcohols.

It is another object of this invention provide methods for protecting against ischemia/reperfusion injury, aging, radiation injury, and head injury by providing a patient with ionizable congeners of aromatic and aliphatic alcohols.

It is another object of this invention to provide a method of protecting individuals against the adverse effects of a variety of drugs and toxic compounds (e.g., adetaminophen, chloroform, etc.).

It is another object of this invention to provide a method of using ionizable congeners of aromatic and aliphatic alcohols to counter inflammatory activity and cholinesterase activity (possible pesticide activity) by administering to a patient a therapuetic antiinflammatory or anticholinesterase dose of the ionizable congeners of aromatic and aliphatic alcohols.

It is another object of this invention to provide a method for using ionizable congeners of aromatic and aliphatic alcohols to prevent cell injury and death in vitro and in vivo.

It is another object of this invention to provide increased efficacy for ionizable congeners of aromatic and aliphatic alcohols by providing tris salt and PEG derivatives.

It is another object of this invention to use dihydrocholesterol succinate, dihydrocholesterol sulfate, cholesteryl sulfate, ergosterol succinate, and ergosterol sulfate as cytoprotective agents.

It is another object of this invention to provide a method for using ionizable tocopheryl congeners for preventing cell injury and death.

It is another object of this invention to provide a method for using alpha tocopherol succinate to prevent cell injury and death.

It is another object of this invention to provide a method for using cholesteryl succinate to prevent cell injury and death.

It is another object of this invention to provide a method for preventing lipid peroxidation.

It is yet another object of this invention to convert certain toxic drug compounds to non-toxic, protective drugs by converting alcohol moieties to ionizable congeners.

It is yet another object of this invention to provide a method of using ionizable congeners of aromatic and aliphatic alcohols of increased water solubility, and particularly the polyethylene glycol ester of tocopherol succinate, for increased cytoprotective, anticancer, antiinflammatory, etc., activity.

According to the invention, experiments have been performed in vitro and in vivo which show that ionizable congeners of aromatic and aliphatic alcohols are effective cytoprotective agents. The term "ionizable congener" refers to ionizable ester and ionizable ether derivatives (including alpha, beta, delta and gamma derivatives of tocopherol and their isomers) which have an ionizable side chain or a side chain that is ionizable upon cellular accumulation. Examples of suitable ionizable congeners of aromatic and aliphatic alcohols include tocopheryl succinate (TS) and cholesteryl succinate. Unesterfied tocopherol and tocopheryl acetate (TA) are not ionizable congeners. The compounds have particular utility as anti-cancer agents, as protective agents against toxic substances, as antiinflammatory agents, in the treatment of ageing, in preventing damage from radiation, ischemia/reperfusion, head injuries, and a variety of other insults to cellular integrity.

BRIEF DESCRIPTION OF THE DRAWINGS

The foregoing and other objects, aspects and advantages of the invention will be better understood from the following detailed description of the preferred embodiments of the invention with reference to the accompanying drawings, in which:

FIGS. 4a–4b are diagrams showing the chemical formulas of tocopherol congeners and contrasting the structure versus activity relationships observed in vitro;

FIGS. 5a–5b are diagrams showing the chemical formulas of tocopherol congeners and contrasting the structure versus activity relationships observed in vivo;

FIGS. 12a–b to 22a–b are chemical structures and tables showing the cytoprotective properties of various substituents of the chemical structures, respectively;

FIGS. 23a–f are chemical structures for tocopherol, cholesterol, tocopherol-succinate, cholesterol-succinate, tocopheryloxybutyric acid, and cholesteryloxybutyric acid, respectively;

DETAILED DESCRIPTION OF THE TABLES

Figure 1A:
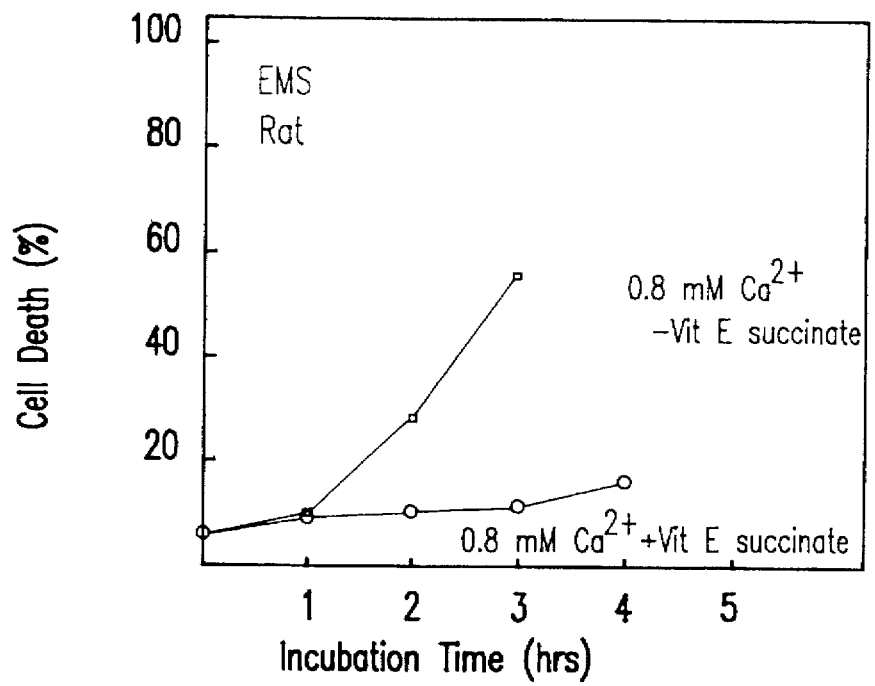
FIGS. 1a–1d are graphs showing the protective effect of alpha-TS on drug-induced liver cell death under physiological conditions.

Table 1 shows free and total calcium content of rat serum and cell culture medium from rat hepatocyte suspensions;

Table 2 shows the protective effect of tocopherol analogs on chemical induced toxicity and lipid peroxidation in rat liver hepatocyte suspensions;

Table 3 shows the protective effect of tocopherol analogs on carbon tetrachloride ($CCl_4$) induced lethality in rats;

Table 4 shows liver specific enzyme levels in rat plasma 48 hours after $CCl_4$ administration;

Table 5 shows the concentrations of alpha-tocopherol and alpha-tocopherol ester in rat liver 24 hours after tocopherol analog administration in vivo;

Table 6 shows tissue distribution of alpha-tocopherol succinate 24 hours after a 100 mg/kg dose of alpha tocopherol succinate;

Table 7 shows the protective effect of tocopherol and succinated analogs on $CCl_4$ induced lethality in rats;

Table 8 shows the protective effect of d-alpha-tocopherol succinate on rat hepatocytes exposed to a variety of toxic insults;

Table 9 shows liver specific enzyme levels in rat plasma 24 hours after acetaminophen administration;

Table 10 shows the protective effect of dl-alpha-tocopherol phosphate on chemical induced toxicity and lipid peroxidation in cultured rat hepatocytes;

Table 11 shows the effect of tocopherol analog dose on the concentration of alpha-T and alpha-TS and on cytoprotection in rat hepatocytes exposed to EMS for 3 hours;

Table 12 shows the protective effect of tocopherol and succinate analogs on EMS-induced toxicity in rat hepatocytes;

Table 13 shows the effect of esterase inhibitors on alpha-TS in hepatocyte suspensions exposed to EMS;

Table 14 shows the effect of tocopherol analogs and succinate on the ATP content of hepatocytes during a 6 hour incubation;

Table 15 shows the effect of succinate derivatives on EMS induced toxicity in rat hepatocyte suspensions;

Table 16 shows the effect of alpha-tocopherol succinate (+) or vehicle (−) administration on the energy status of rat tissue;

Table 17 shows the protective effect of tocopherol and succinate analogs on $CCl_4$ induced lethality in rats;

Table 18 shows the in vivo results of $CCl_4$ induced lethality and hepatotoxicity in rats pretreated with various tocopherol and succinate analogs;

Table 19 shows in vivo survival times of CDF1 mice following an injection of 106 L1210 leukemia cells where certain groups of mice were treated with alpha-TS tris salt or cholesteryl succinate tris salt;

Table 20 shows alpha-TS tris salt and cholesterol succinate tris salt protection in vivo against $CCl_4$ induced hepatotoxicity;

Table 21 shows the in vivo protective effect of cholesterol succinate against damage from total ischemia;

Table 22 shows the in vivo protective effect of cholesterol succinate against damage from partial ischemia;

Table 23 shows the in vivo protective effect of cholesterol succinate against acetaminophen induced hepatotoxicity;

Table 24 shows the in vivo effects of pretreatment with cholesterol succinate on tremors, salivation, and survival when animals are subjected to a THA challenge;

Table 25 shows the effects of cholesterol succinate pretreatment on the pentobarbitone sleeping time in vivo;

Tables 26 and 27 show in vivo the protective capacity of cholesterol succinate in the free acid and tris salt forms and alpha tocopherol succinate in the free acid and tris salt forms, respectively, against $CCl_4$ induced hepatotocity;

Table 28 shows in vivo the protective capactiy of varying concentrations of cholesterol succinate against $CCl_4$ induced hepatotoxicity;

Table 29 shows in vivo the effect of pretreatment time on cholesterol succinated tris salt mediated protection against $CCl_4$ hepatotoxicity;

Table 30 shows in vivo the effects of various ionizable congeners of aromatic and aliphatic alcohols on $CCl_4$ hepatotoxicity;

Table 31 shows in vivo the effects of cholesterol anaolgs on $CCl_4$ hepatotoxicity;

Table 32 shows in vivo the effects of alpha-TS and cholesterol succinate tris salt on $CCl_4$ hepatotoxicity when administered using polyethylene glycol (PEG) as the vehicle;

Table 33 shows in vivo the effects of tris succinate, cholesteryl 3-sulfate, palmityl succinate, palmityl alcohol, and hydrocortisone 21-succinate on $CCl_4$ hepatotoxicity;

Table 34 shows in vivo the effects of cholesterol succinate tris salt, estrone sulfate potassium salt, dehydroepiandrosterone 3-sulfate sodium salt, cholesterol hydrogen phthalate, and dehydrocholesterol sulfate on $CCl_4$ hepatotoxicity;

Table 35 shows in vivo the effect of dehydrocholesterol sulfate sodium salt, dehydrocholesterol plus sodium sulfate, linoleyl succinate, and linoleyl alcohol on $CCl_4$ hepatotoxicity;

Table 36 shows in vivo the effect of dehydrocholesterol succinate on $CCl_4$ hepatotoxicity;

Table 37 shows in vivo the effects of cholesterol succinate tris salt, dehydrocholesterol succinate tris salt, phytol succinate, and phytol on $CCl_4$ hepatotoxicity;

Table 38 show in vivo the effect of ergosterol, ergosterol sulfate potassium salt, and ergosterol succinate tris salt on $CCl_4$ hepatotoxicity;

Table 39 shows in vivo the effect of dehydroepiandrosterone 3-succinate, linoleyl succinate, and ergosterol on $CCl_4$ hepatoxiticity;

Table 40 shows in vivo the effect of estrone 3-succinate and lauryl sulfate sodium salt on $CCl_4$ hepatotoxicity;

Table 41 shows in vivo the effect of retinoic acid on retinol acetate on $CCl_4$ hepatotoxicity;

Table 42 shows in vivo the effect of estrone, estrone acetate and estrone succinate on $CCl_4$ hepatotoxicity.

DETAILED DESCRIPTION OF THE PREFERRED EMBODIMENTS OF THE INVENTION

Experiments have been performed in vitro and in vivo which show that under physiological conditions, ionizable congeners of aromatic and aliphatic alcohols protect mammalian cells from cell injury and death.

Previous studies by the inventor, Fariss, *Science* 227:751, (1985) and Pascoe, *Arch. Biochem. Biophys.* 256:159, (1987) demonstrated that rat hepatocytes could be protected from the toxic effects of drugs by incubating these cells in a $Ca^{2+}$ free medium with d-alpha-tocopheryl succinate (alpha-TS). The addition of 3.5 mM $Ca^{2+}$ to the medium, however, eliminated the cytoprotective effect of alpha-TS. The physiological relevance of results obtained from in vitro studies using abnormally low (0 mM) or abnormally high (3.5 mM) extracellular $Ca^{2+}$ concentrations is unclear. The extracellular calcium concentrations (0 and 3.5 mM) were selected to test a hypothesis proposed by Farber, *Life Sci.* 29:1289, (1981) on the importance of extracellular $Ca^{2+}$ in toxic cell injury (See, Fariss, *Toxicol. Appl. Pharmacol.* 79: 296, (1985)), and not for the purpose of simulating or predicting cytoprotection in vivo.

To determine the $Ca^{2+}$ concentration in cell culture medium needed to simulate physiological conditions, the $Ca^{2+}$ content of serum, the in vivo cell perfusate, was examined. Table 1 shows the measured free and total calcium content of rat serum and cell culture medium from rat hepatocyte suspension.

TABLE 1

Free and Total Calcium Content of Rat Serum and Cell Culture Medium from Rat Hepatocyte Suspensions

| Specimen | Calcium Concentration | |
|---|---|---|
| | Total[b] | Free[c] |
| 1. Rat Serum | 5.2 ± 0.1 | 1.2 ± 0.1 |
| 2. Cell Culture Medium[d] From Hepatocyte Suspensions | | |
| a) No Additions ($Ca^{2+}$ Free) | <0.1 | <0.1 |
| b) + 0.8 mM $CaCl_2$ | 0.9 ± 0 | 0.8 ± 0.2 |
| c) + 3.5 mM $CaCl_2$ | 3.5 ± 0.1 | 3.0 ± 0.2 | a) Results are expressed as X ± SE of 3 to 5 separate specimens.
b) As measured with atomic absorption spectroscopy.
c) As measured with a calcium electrode.
d) $Ca^{2+}$ free Waymouth 751/2 medium The total $Ca^{2+}$ content of rat serum is approximately 5 mM which comprises approximately 1 mM free $Ca^{2+}$ and 4 mM plasma protein bound $Ca^{2+}$. Thus, mammalian cells in vivo are maintained in an environment (serum) in which approximately only 1 mM $Ca^{2+}$ is available for exchange with cells while the remainder is bound and unavailable. Because of calcium's regulatory role in the cell, the concentration of free $Ca^{2+}$ in serum is tightly controlled to prevent fluctuations. In vitro model systems should therefore have a concentration of free $Ca^{2+}$ of approximately 1 mM to simulate physiological conditions. All in vitro studies performed by the inventor were performed under physiological conditions.

Figure 1B:
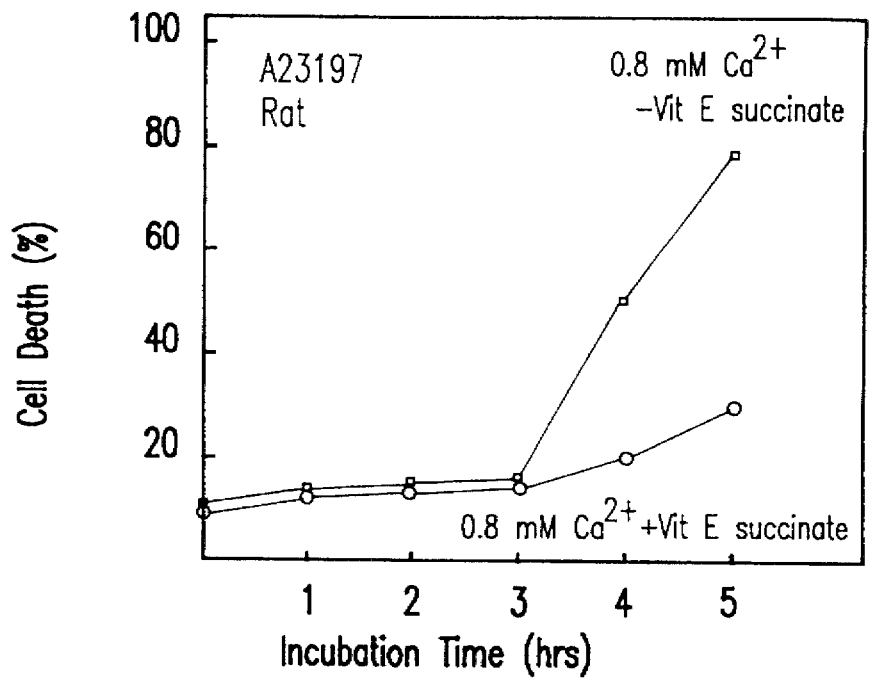
Figure 1C:
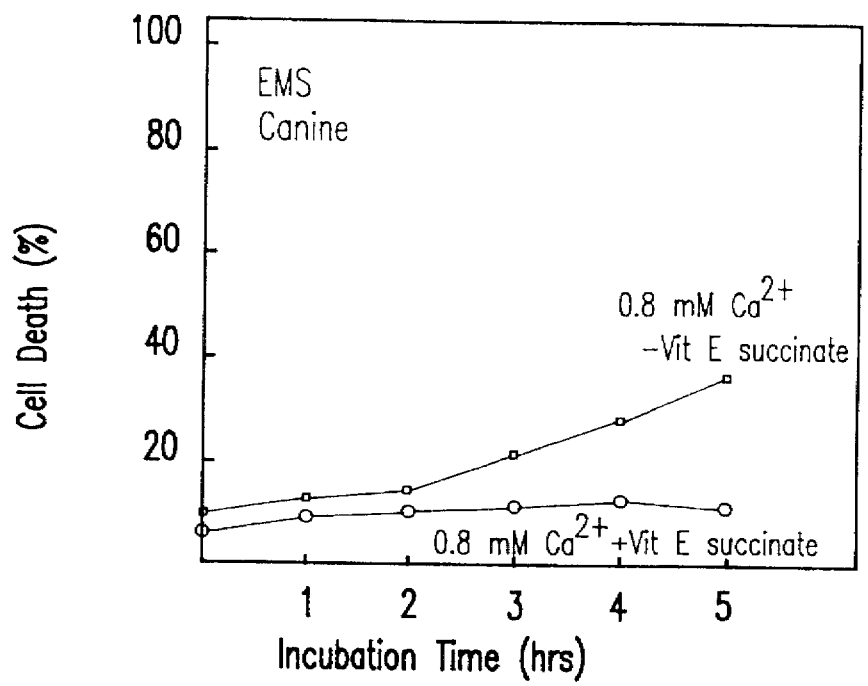
Figure 1D:
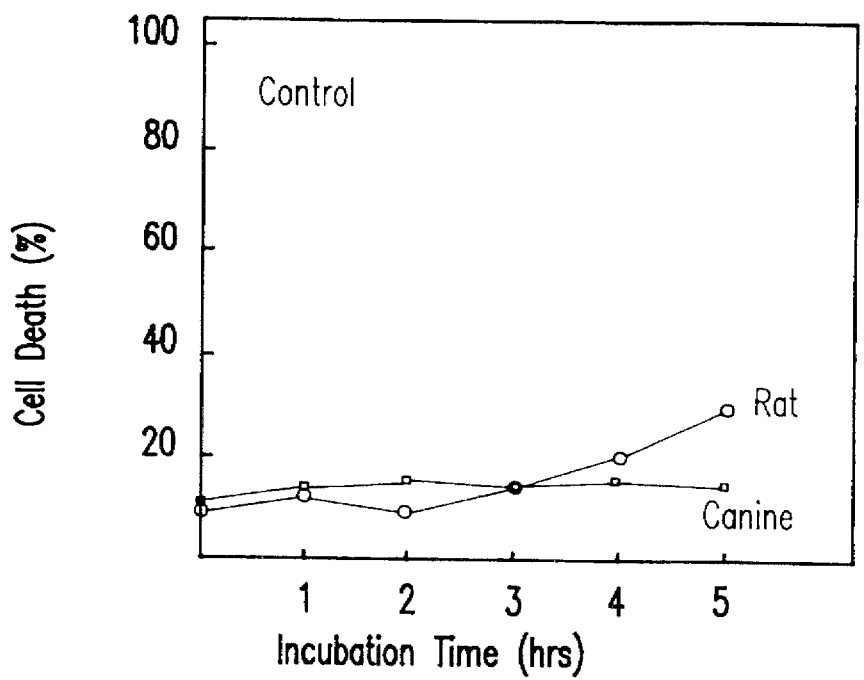

To determine if alpha-TS is a cytoprotective agent under physiological conditions, liver cells were incubated with Waymouth's medium containing approximately 1 mM extracellular $Ca^{2+}$ in the presence and absence of alpha-TS. FIGS. 1a and 1b show that 25 μM alpha-TS protected both rat and canine hepatocytes from the lethal effects of 50 mM of the alkylating agent ethylmethanesulfonate (EMS). FIG. 1c shows that 25 μM alpha-TS protected rat hepatocytes from the lethal effects of 5 μM of the ionophore A23187. FIG. 1d shows the response of control hepatocytes over the same period of time. The response curves shown in FIGS. 1a through 1c demonstrate alpha-TS is cytoprotective under physiological conditions and its anticytotoxic properties are not limited to a particular animal species. The protective effect of alpha-TS is retained in the water soluble polyethylene glycol (PEG) polymer of alpha-TS. When 25 μM of d-alpha-tocopheryl polyethylene glycol 1,000 succinate, available from Eastman Chemical Products, Inc. of Tennessee, was administered to rat hepatocytes, protection was observed against EMS-induced toxicity.

Figure 2A:
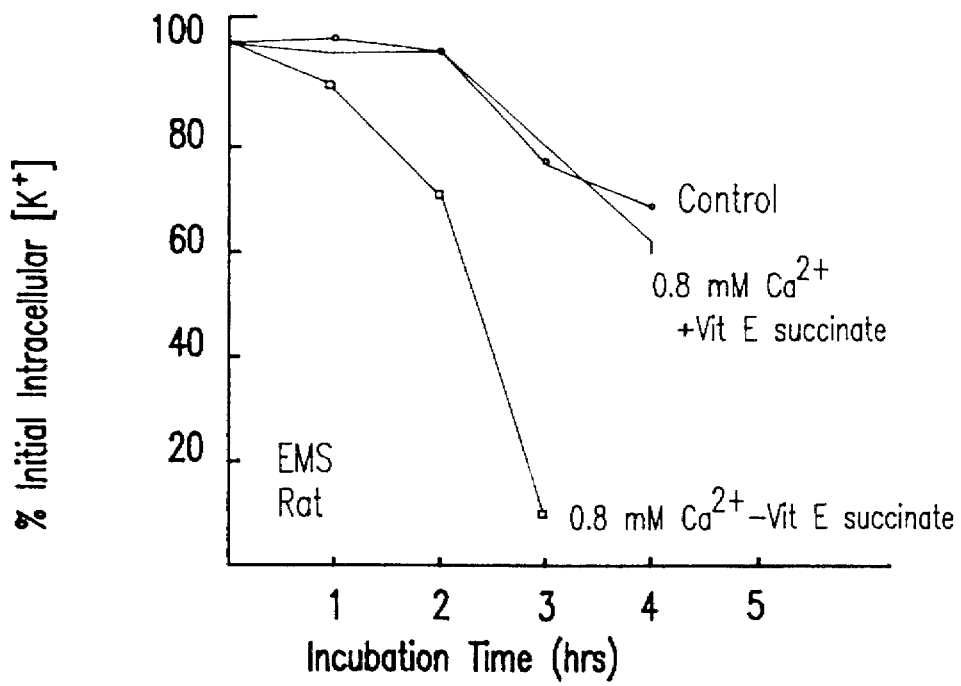
FIGS. 2a–2b are graphs showing the protective effect of alpha-TS on liver cell metabolic performance during a toxic insult.
Figure 2B:
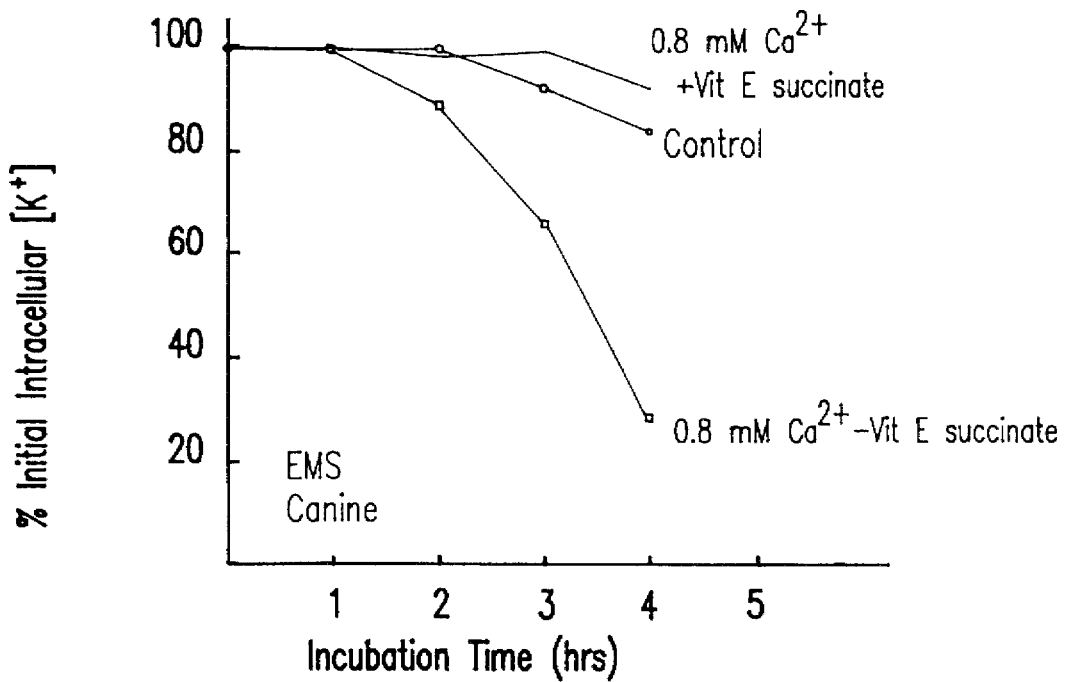

Medzhradsky, Biochem. Med. 13:164 (1975), has noted that the cell's ability to maintain its intracellular concentration of potassium ($K^+$) is an excellent indicator of the metabolic integrity of the cell. A concentration gradient exists for $K^+$ with greater concentrations found intracellularly. To maintain this gradient, the cell is dependent on the action of the $Na^+$-$K^+$ ATPase pump and an adequate supply of ATP. As cellular ATP levels decline, the ATPase pump is unable to maintain the gradient resulting in the loss of intracellular $K^+$ by equilibration with the extracellular space. Because the maintenance of cellular metabolic processes is essential to the continual repair and survival of cells, organ systems, and organisms, the effect of alpha-TS on the metabolic integrity of rat liver cells during a toxic insult was investigated by measuring intracellular K+ levels. FIGS. 2a–2b show the response of rat and canine hepatocytes, respectively, exposed to 50 mM EMS. The cellular $K^+$ concentration in untreated rat and canine hepatocytes declines rapidly, suggesting drug-induced injury and loss of metabolic performance. In contrast, rat and canine hepatocytes treated with 25μM alpha-TS during the toxic insult showed no loss of intracellular K+ as compared with control. The response curves shown in FIGS. 2a and 2b indicate that alpha-TS under physiological conditions can maintain the metabolic integrity of animal hepatocytes during a toxic insult.

Experiments were conducted in vitro to compare the protective effect of d-alpha-tocopherol (alpha-T), d-alpha-tocopherol acetate (alpha-TA), and alpha-TS on cells treated with a lethal dose of EMS. Table 2 shows the results of the experiments where rat liver hepatocytes were treated with 50 mM EMS.

TABLE 2

Protective Effect of Tocopherol Analogs on Chemical Induced Toxicity and Lipid Peroxidation in Rat Liver Hepatocyte Suspensions

| | Control | alpha-T | alpha-TA | alpha-TS |
| --- | --- | --- | --- | --- |
| 1) % Protection | 0% | 19% | 12% | 100% |
| 2) % Inhibition of Lipid Peroxidation | 0% | 9% | 14% | 100% |
| 4) Cellular alpha-T(nmoles/ $10^6$ cells) | 0.1 | 2.6 | 0.3 | 0.7 |

TABLE 2-continued

Protective Effect of Tocopherol Analogs on Chemical Induced Toxicity and Lipid Peroxidation in Rat Liver Hepatocyte Suspensions

| | Control | alpha-T | alpha-TA | alpha-TS |
| --- | --- | --- | --- | --- |
| 5) Cellular Tocopherol ester (nmoles/$10^6$ cells) | N.D. | N.D. | 1.7 | 2.6 |

Freshly isolated hepatocyte suspensions were prepared in medium with Waymouths medium and incubated with vitamin E (25 μM, alpha-TS, alpha-T or alpha-TA) for approximately fifteen minutes. Suspensions were then treated with a toxic chemical (EMS, 50 mM; or ionphore A-23187, 5 μM) or a vehicle control and monitored hourly for loss of viability and cellular alpha-T, alpha-TS and alpha-TA content. At each time-point, rapid separation of viable from non-viable hepatocytes and medium was accomplished by the dibutyl phthalate centrifugation method. Cell viability was monitored hourly by measuring LDH leakage with a Cobas Analyzer and intracellular [$K^+$] with a flame photometer. LDH was routinely measured in the medium while intracellular $K^+$ was measured in the 10% perchloric acid lysate of viable cells. Lipid peroxidation was determined by measuring TBA reactants in the medium. The measurement of alpha-T levels were obtained by adding 1 nmol of the internal standard delta-tocopherol, to samples of viable hepatocytes. The samples were diluted with 0.3 ml 1% ascorbate in 0.1M SDS, 0.4 ml ethanol, sonicated and extracted once with 0.8 ml hexane. Next, the hexane extract was evaporated to dryness with $N_2$, the residue dissolved in 2.5% ascorbate in methanol (1 ml) and analyzed (100 μl) by high-performance liquid chromatograph (HPLC). Measurements of alpha-T were made on a Hewlett Packard 1084B chromatograph equipped with a McPherson 749 fluorescence detector (excitation, 210 nm; emission filter, 320 nm) and a Spherisorb ODS II column (250×4.6 mm, 5 micron; Alltech, Avondale, Pa.). The mobile phase, 95% MeOH was run isocratically and the HPLC retention times for delta and alpha-tocopherol were approximately eleven and sixteen minutes, respectively. Cellular concentrations of the tocopherol esters, alpha-TS and alpha-TA, were determined by measuring the amount of alpha-T in cellular extracts before and after base hydrolysis. Cellular extracts (MeOH) described in the previous paragraph were divided into two portions with one analyzed for alpha-T (as described above) and the second (0.5 ml) treated with 0.2 ml of 4M KOH overnight. Following the addition of 0.2 ml 4M HCl, the neutralized KOH-MeOH extracted with 0.8 ml hexane. The hexane extract was evaporated with $N_2$, reconstituted in 2.5% ascorbate in MeOH and analyzed for alpha-T with HPLC as described above. The release of alpha-T by base hydrolysis using the above method was directly proportional to the alpha-TA or alpha-TS concentration (over the concentration range of 0.1–10 nmol). A standard curve for each tocopherol congener was run with every assay. The oxidation of alpha-T during the hydrolysis and analysis was prevented by the addition of 2.5% ascorbate to the MeOH. The limit of detection for alpha-T and alpha-T esters in the methods described above are 0.05 and 0.1 nmol/$10^6$ cells, respectively. Only viable cells were monitored in the laboratory procedures. Neither alpha-T nor alpha-TA protected cells from EMS; however, alpha-TS completely protected hepatocytes from EMS toxicity.

In Prasad, Cancer Res. 42:550 (1982), the unique effect of alpha-TS on the growth and morphology of cultured tumor cells incubated under physiological conditions was attributed to the accumulation of cellular alpha-T from alpha-TS.

However, the experimental results shown in Table 2 indicate that cellular protection does not correlate with the accumulation of alpha-T, but instead is dependent on the presence of cellular alpha-TS. For example, hepatocytes with markedly elevated levels of cellular alpha-T (2.6 nmol/$10^6$ cells, alpha-T treated) and cellular alpha-TA (1.7 nmol/$10^6$ cells, alpha-TA treated) were susceptible to chemical induced toxicity and lipid peroxidation. In contrast, liver cells that accumulated alpha-TS (2.6 nmol/$10^6$ cells) and a modest amount of alpha-T (0.7 nmol/$10^6$ cells) were completely protected from chemical toxicity. In addition to its cytoprotective property, alpha-TS exhibits a membrane stabilization property by preventing EMS induced lipid peroxidation. Neither alpha-T nor alpha-TA demonstrated this property. Phospholipids are the major structural building blocks of cell membrane. Cell injury caused by chemical or radiation treatment is generally accompanied by activation of phospholipases which break down the cell barriers. The results shown in Table 2 correspond to observations by Toivanen, *Prost. Leuk. Med.* 26:265 (1987), which suggested alpha-TS inhibits platelet phospholipase $A_2$ activity. The ionizable tocopheryl congener (alpha-TS) may stabilize membranes by interacting with the charged portion of the phospholipid molecule or by chelating free intracellular $Ca^{2+}$.

The in vivo effect of alpha-TS was tested by administering a lethal oral dose of carbon tetrachloride ($CCl_4$) to male Sprague-Dawley rats. Table 3 shows in vivo results for $CCl_4$ challenges to rat viability.

TABLE 3

Protective Effect of Tocopherol Analogs on Carbon Tetrachloride ($CCl_4$) Induced Lethality in Rats

| Tocopherol Analog Administered | Days Survived After $CCl_4$ Treatment (g$CCl_4$/kg) | | | | |
|---|---|---|---|---|---|
| | 5.0 | 3.8 | 2.9 | 2.2 | $LD_{50}$ |
| Control (Vehicle Only) | 2 | 2 | 3 | >7 | 2.5 |
| d-alpha-T (100 mg/kg, ip) | 2 | 2 | 2 | 3 | 1.5 |
| d-alpha-TA (100 mg/kg, ip) | 2 | 2 | 3 | >7 | 2.5 |
| d-alpha-TS (100 mg/kg, ip) | 2 | >7 | >7 | N.D. | 4.4 |
| d-alpha-TS (100 mg/kg, oral) | 2 | 2 | 3 | >7 | 2.5 |

$LD_{50}$-Dose is the $CCl_4$ required for 50% lethality.
$LD_{50}$ estimation performed according to Bruce, Tox. Appl. Pharm., Vol. 15, pg 151 (1985).
N.D. — Not Determined In addition to the data shown in Table 3, the alpha-T group was also exposed to 1.7 g $CCl_4$/kg body weight and 1.3 g $CCl_4$/kg body weight. At 1.7 g $CCl_4$/kg, the rats survived three days. At 1.3 g $CCl_4$/kg, the rats survived greater than seven days. In the experiment described in Table 3, a single dose of alpha-TS dissolved in peanut oil:ethanol (3:2) was given to male Sprague-Dawley rats. The dose was given 24 hours prior to an orally administered $CCl_4$ challenge dissolved in peanut oil. Two to nine animals were tested per treatment. The control group comprised rats pretreated with the vehicle only. Survival was monitored for at least 7 days after the toxic insult. Rats treated with the vehicle alone died within two days of a 2.9 g/kg $CCl_4$ or greater challenge. Alpha-TS treated rats survived more than 7 days after a 3.8 g/kg $CCl_4$ or less challenge. These results demonstrate that alpha-TS treatment in vivo protects rats from the lethal effects of $CCl_4$. Table 3 shows that an intraperitoneal dose of alpha-TS is far more protective than alpha-T or alpha-TA. The estimated lethal dose, $LD_{50}$, from $CCl_4$ was increased from less than 2.5 to 4.4 g/kg body weight with the administration of 100mg/kg alpha-TS (ip). Histopathology was performed on rats treated with $CCl_4$ and it was determined that the liver was the only organ affected by a $CCl_4$ challenge (e.g., the other tissues appeared normal). Cytoprotection against $CCl_4$ lethality was not observed after an oral dose of alpha-TS (100 mg/kg), which is the only form alpha-TS is currently commercially available in for therapeutic and prophylactic use.

In vivo experiments were performed to determine if alpha-TS administration protects the liver from chemical toxicity. The liver is the target organ for $CCl_4$. $CCl_4$ is a hepatotoxic agent that induces centrilobular liver necrosis through its metabolism to free radicals. Male Sprague-Dawley rats were given an intraperitoneal dose (100 mg/kg) of a tocopherol analog 24 hours prior to a $CCl_4$ challenge (2.9 g/kg given by oral gavage). Forty eight hours after the challenge, the rats were sacrificed and the levels of aspartate aminotransferase (AST) and alanine aminotransferase (ALT) were measured. Table 4 shows the AST and ALT levels which were measured.

TABLE 4

Liver Specific Enzyme Levels in Rat Plasma 48 Hours After $CCl_4$ Administration

| Treatment | AST | ALT |
|---|---|---|
| Negative Control (no $CCl_4$) | 69 ± 5 | 34 ± 3 |
| Positive Control ($CCl_4$) | 15,601 ± 5114 | 2,819 ± 1654 |
| d-alpha-T + $CCl_4$ | 17,330 ± 7220 | 4,678 ± 290 |
| d-alpha-TA + $CCl_4$ | 20,233 ± 3525 | 6,108 ± 417 |
| d-alpha-TS + $CCl_4$ | 3,430 ± 1500* | 631 ± 17* |

AST and ALT levels are listed in Units/L and expressed as X ± S.E. (n = 3–4).
*p < .05, as compared to other $CCl_4$ treatments.

AST is the same enzyme as Serum Glutamic Oxalacetic Transaminase (SGOT) and ALT is the same enzyme as Serum Glutamic Pyruvate Transaminase (SGPT). AST and ALT levels are commonly used experimentally and clinically as indicators of liver cell injury or death. Alpha-TS pretreated rats had much lower AST and ALT levels than the alpha-T and alpha-TA pretreated rats. Liver histopathology from the experiment revealed that alpha-TS significantly reduced $CCl_4$ induced centrilobular necrosis. In fact, seven to nine days following a 2.9 g/kg $CCl_4$ challenge the livers from rats pretreated with alpha-TS showed no histological signs of cell injury or cell death. These data indicate that the cellular accumulation of alpha-TS limits $CCl_4$ destruction of the liver as well as promoting hepatic repair.

In vivo experiments were performed to determine the accumulation of alpha-T and esters of alpha-T in the liver. 100 mg/kg body weight of a tocopherol analog was administered to Sprague-Dawley rats using a peanut oil:ethanol vehicle (3:2). Twenty four hours later the rats were sacrificed and the accumulation of the tocopherol analog in the liver was determined. Table 5 contrasts the accumulation of alpha-T, alpha-TA, and alpha-TS (ip and oral).

TABLE 5

Concentration of Alpha-Tocopherol and Alpha-Tocopherol Ester in Rat Liver 24 Hours after Tocopherol Analog Administration in vivo

| Tocopherol Analog | Liver Concentration | | Protection from $CCl_4$ |
|---|---|---|---|
| | Alpha-T | Ester | |
| Control (vehicle) | 28 ± 3 | N.D. | — |
| Alpha-T (ip) | 128 ± 10 | N.D. | No |
| Alpha-TA (ip) | 56 ± 10 | 92 ± 6 (alpha-TA) | No |

TABLE 5-continued

Concentration of Alpha-Tocopherol and Alpha-
Tocopherol Ester in Rat Liver 24 Hours after
Tocopherol Analog Administration in vivo

| Tocopherol | Liver Concentration | | Protection |
|---|---|---|---|
| Analog | Alpha-T | Ester | from $CCl_4$ |
| Alpha-TS (ip) | 51 ± 5 | 119 ± 16 (alpha-TS) | Yes |
| Alpha-TS (oral) | 66 ± 12 | N.D. | No |

Alpha-T and Ester are in nmoles/g.
N.D. Not Determined

The results of the experiment show alpha-TS cytoprotection is dependent on the cellular accumulation of the alpha-TS molecule, not on the accumulation of alpha-T. The most striking example of this dependency is the elimination of both the accumulation of hepatic alpha-TS and protection against $CCl_4$ lethality when alpha-TS is administered orally. Presumably hydrolysis of the alpha-TS molecule occurred by duodenal esterases from biliary and pancreatic secretions.

In a one month study with three human males aging from 35 to 62 years 400 units of alphatocopheryl succinate were taken per day. Subsequent blood samples were taken from each individual and analyzed for alpha-T and alpha-TS content. Substantial amounts of alpha-TS in plasma and erythrocytes were observed for only one individual. Interpreting these results with the rat data shown in Table 5, it can be said that in the majority of the population, oral administration of alpha-TS will not result in the accumulation of tissue alpha-TS. However, in select individuals, as determined possibly by ethnic origin or diet, tissue alpha-TS accumulation can occur with oral dosing. The absence of alpha-TS hydrolysis in the gut of the one individual in the study who had substantial amounts of alpha-TS in plasma may be attributed to the absence of duodenal secretions after oral alpha-TS administration (lack of dietary fats to stimulate duodenal secretions at the time of alpha-TS administration).

A similar in vivo experiment to that discussed in conjunction with Table 5 was performed to determine if other tissues accumulate alpha-TS. Male Sprague-Dawley rats were given a 100 mg/kg dose of alpha-TS using a variety of chemical forms and vehicles. A variety of techniques were used to administer the alpha-TS. Twenty four hours later the rats were sacrificed and the tissues were tested for alpha-TS accumulation. Table 6 shows the accumulation of alpha-TS in each of the tissues tested during the experiment.

TABLE 6

Tissue Distribution of Alpha-Tocopherol and Alpha-
Tocopherol Succinate 24 Hours After a 100 mg/kg Dose
of Alpha-Tocopherol Succinate (a) Vehicle control (No Alpha-TS) (1 dose)
(b) Alpha-TS (ip)   (Alpha-TS dissolved in peanut oil and ETOH) (1 dose)
(c) Alpha-TS (ip)   (K+ salt of Alpha-TS dissolved in saline) (1 dose)
(d) Alpha-TS (iv)   (K+ salt of Alpha-TS dissolved in saline) (1 dose)
(e) Alpha-TS (iv)   (Alpha-TS incorporated in liposomes) (1 dose)
(f) Alpha-TS (ip)   (Alpha-TS in olive oil) (7 doses administered 1 per day for 7 days)

TABLE 6-continued

| | | nmoles/gm of Tissue | | | | | | |
|---|---|---|---|---|---|---|---|---|
| | | Liver | Brain | Kidney | Heart | Lung | Blood | Plasma |
| (a) | A-T | 28 | 27 | 29 | 27 | 47 | 10 | 13 |
| | A-TS | ND | ND | ND | ND | ND | ND | ND |
| (b) | A-T | 51 | 34 | 37 | 31 | 42 | 13 | 14 |
| | A-TS | 119 | ND | 31 | 47 | 90 | 7 | 8 |
| (c) | A-T | 260 | 37 | 45 | 48 | 93 | 21 | 22 |
| | A-TS | 518 | ND | 15 | 18 | 60 | 19 | 24 |
| (d) | A-T | 380 | 40 | 60 | 51 | 102 | 24 | 34 |
| | A-TS | 445 | ND | 27 | 24 | 385 | 18 | 30 |
| (e) | A-T | 105 | 47 | 52 | 68 | 112 | 22 | 26 |
| | A-TS | 322 | ND | ND | 10 | 4843 | 6 | 5 |
| (f) | A-T | 121 | 30 | 48 | 41 | 89 | 21 | — |
| | A-TS | 161 | 6 | 44 | 34 | 128 | 15 | — |

N.D. — Not Detected (Detection limit for Alpha-TS was 5–10 nmol/gm of Tissue)

The lung, kidney, heart, erythrocytes and plasma accumulate significant amounts of alpha-TS when administered intraperitonealy (ip) or intravenously (iv). By changing the chemical form ($K^+$ salt) or vehicles (liposomes), the accumulation of alpha-TS can be targeted towards specific tissues. Repeated administration, (f) in table 6, resulted in accumulation of alpha-TS in the central nervous system. Note that the results in Table 6 were determined twenty four hours after a single dose of alpha-TS. Additional tests revealed that alpha-TS could not be detected forty eight hours after a single dose administration of alpha-TS.

The data in Table 6 suggest that protection following alpha-TS administration would not be specific to one organ or tissue type. An in vivo experiment with Sprague-Dawley rats confirmed this assumption. Rats received a 100 mg/kg (ip) dose of alpha-TS twenty four hours prior to a 40 mg/kg (ip) insult of paraquat which is a lung specific toxic agent. The rats also received a 100 mg/kg (ip) dose of alpha-TS each day after the paraquat insult. Protection with alpha-TS administration was observed by its ability to extend the survival time of the paraquat exposed rats from 4 days to 6 days. In addition to the paraquat results, rats pretreated with alpha-TS prior to a toxic dose of $CCl_4$ recover from the acute central nervous system toxic manifestations of $CCl_4$, which include CNS depression resulting in narcosis, several days before rats which are not treated with alpha-TS. Hence, alpha-TS protects rats from neurotoxic as well as hepatotoxic effects of $CCl_4$.

In vivo experiments were performed to determine if the time the ionizable tocopherol analog (alpha-TS) is administered affects the cytoprotective functions. Male Sprague-Dawley rats were given a 100 mg/kg intraperitoneal dose of a tocopherol or succinate analog and were given a lethal dose of $CCl_4$ (2.9 g/kg by oral gavage). Table 7 contrasts the times of administration of the tocopherol or succinate analog and the times of administration of the lethal dose of $CCl_4$ with the survival of the rats in the study (3 to 6 rats per protective treatment).

TABLE 7

Protective effect of Tocopherol and Succinate
Analogs on $CCl_4$ Induced Lethality in Rats

| Tocopherol Analog Administered | Days Survived after $CCl_4$ |
|---|---|
| 1. Vehicle Control | 2 |
| 2. Alpha-TS (100 mg/kg, single dose | >7* |

TABLE 7-continued

Protective effect of Tocopherol and Succinate
Analogs on CCl$_4$ Induced Lethality in Rats

| Tocopherol Analog Administered | Days Survived after CCl$_4$ |
|---|---|
| 24 hours prior to CCl$_4$) | |
| 3. Alpha-TS (100 mg/kg, single dose 12, 10, 8, 6, 4, 2, or 1 hour prior to CCl$_4$) | 2 to 4 |
| 4. Alpha-TS (100 mg/kg, dosed 1 hour prior to CCl$_4$ and daily thereafter) | >7* |
| 5. Alpha-TS (100 mg/kg, dosed 1 hour after CCl$_4$ and daily thereafter) | 2 |
| 6. Succinic Acid, Na Salt (1 g/kg, dosed 24 hours or 1 hour prior to CCl$_4$ and daily thereafter) | 2 |
| 7. Monomethyl Succinate (1 g/kg, dosed 24 hours and 1 hour prior to CCl$_4$) | 2 |
| 8. Dimethyl Succinate (1 g/kg, dosed 24 and 1 hour prior to CCl$_4$) | 2 |

*p < .05, as compared to vehicle control

Table 7 shows that greater than 12 hours of incubation time are required for cytoprotection if a single dose of alpha-TS is used. However, the incubation time required after alpha-TS administration can be reduced to one hour if daily injections of alpha-TS are given after the CCl$_4$ insult. Based on the fact that a single dose of alpha-TS leaves the system after forty eight hours, the optimal dosing would be periodic (daily). The results suggest that optimal cytoprotection results from daily or multiple dosing of alpha-TS. The finding that alpha-TS did not protect cells after a CCl$_4$ challenge may suggest that alpha-TS should be given in advance, i.e., take alpha-TS before an X-ray examination, or heart surgery. Alpha-TS treatment after the toxic challenge may still be effective if milder challenges are applied. Table 7 shows that succinic acid, monomethyl succinate and dimethyl succinate are not cytoprotective.

In vitro experiments were performed to determine if alpha-TS could protect cells from different toxic insults. Under physiological conditions, rat hepatocytes were incubated with medium containing 25 μM alpha-TS. The hepatocytes were exposed to EMS, a potent mutagen and alkylating agent; the ionophore A23187, a membrane active compound that permits the equilibration of divalent cations across cell membranes; cadmium, a heavy metal, environmental contaminant, and known carcinogen who's mechanism of toxicity remains unknown; 95% O$_2$, an excessive oxygen insult that produces an abundance of toxic oxygen free radicals and reactive oxygen intermediates in the cell; doxorubicin (adriamycin), a clinically important antitumor agent with cytotoxic effects proposed to result from its metabolic activation and the generation of reactive oxygen species; carbon tetrachloride (CCl$_4$); and hypoxia (an absence of oxygen followed by reoxygenation). Table 8 shows the results of the experiments.

TABLE 8

Protective Effect of d-Alpha-Tocopherol Succinate on
Rat Hepatocytes Exposed to a Variety of Toxic
Insults.

| | % Cell Death | |
|---|---|---|
| Toxic Insults | No Alpha-TS | Alpha-TS |
| Control (Vehicle only) | 21 | 21 |
| EMS (50 mM) | 68 | 25 |

TABLE 8-continued

Protective Effect of d-Alpha-Tocopherol Succinate on
Rat Hepatocytes Exposed to a Variety of Toxic
Insults.

| | % Cell Death | |
|---|---|---|
| Toxic Insults | No Alpha-TS | Alpha-TS |
| Ionophore A23187 (5 μM) | 73 | 24 |
| Cadmium (0.1 mM) | 70 | 24 |
| 95% Oxygen | 57 | 23 |
| Doxorubicin (100 μM) | 62 | 28 |
| CCl$_4$ (2.5 mM) | 63 | 38 |
| Hypoxia (accomplished by 4 hrs under N$_2$ and 2 hrs under O$_2$) | 70 | 49 |

Table 8 shows that 25 μM alpha-TS protects (note control) rat hepatocytes from lethal doses of EMS, Ionophore A23187, Cadmium, Oxygen, Doxorubicin, CCl$_4$, and hypoxia.

In vivo experiments were performed to determine if alpha-TS administration protects the liver from the hepatotoxic effects of acetaminophen. Acetaminophen is a commonly used analgesic that is metabolized to a reactive intermediate. One group of male Sprague-Dawley rats were given an intraperitoneal dose (100 mg/kg) of alpha-TS 24 hours prior to an acetaminophen challenge (2.5 g/kg body weight given by oral gavage). The other group of male Sprague-Dawley rats received only the acetaminophen challenge. Forty eight hours after the challenge the rats were sacrificed and the levels of aspartate aminotransferase (AST) and alanine aminotransferase (ALT) were measured. Table 9 shows the AST and ALT levels which were measured.

TABLE 9

Liver Specific Enzyme Levels in Rat Plasma 24 hours
After Acetaminophen Administration

| Treatment | AST (Units/L) | ALT (Units/L) |
|---|---|---|
| Vehicle Only (20% Tween 80) | 67 ± 8 | 49 ± 6 |
| Acetaminophen (ACT) | 6,968 ± 3546 | 2,137 ± 442 |
| (ACT) + alpha-TS | 1,659 ± 607 | 432 ± 188* |

*P < .05, as compared to other ACT treatments

Table 9 shows that pretreating rats with alpha-TS greatly suppresses the damage associated with free radical production by acetaminophen.

Figure 3:
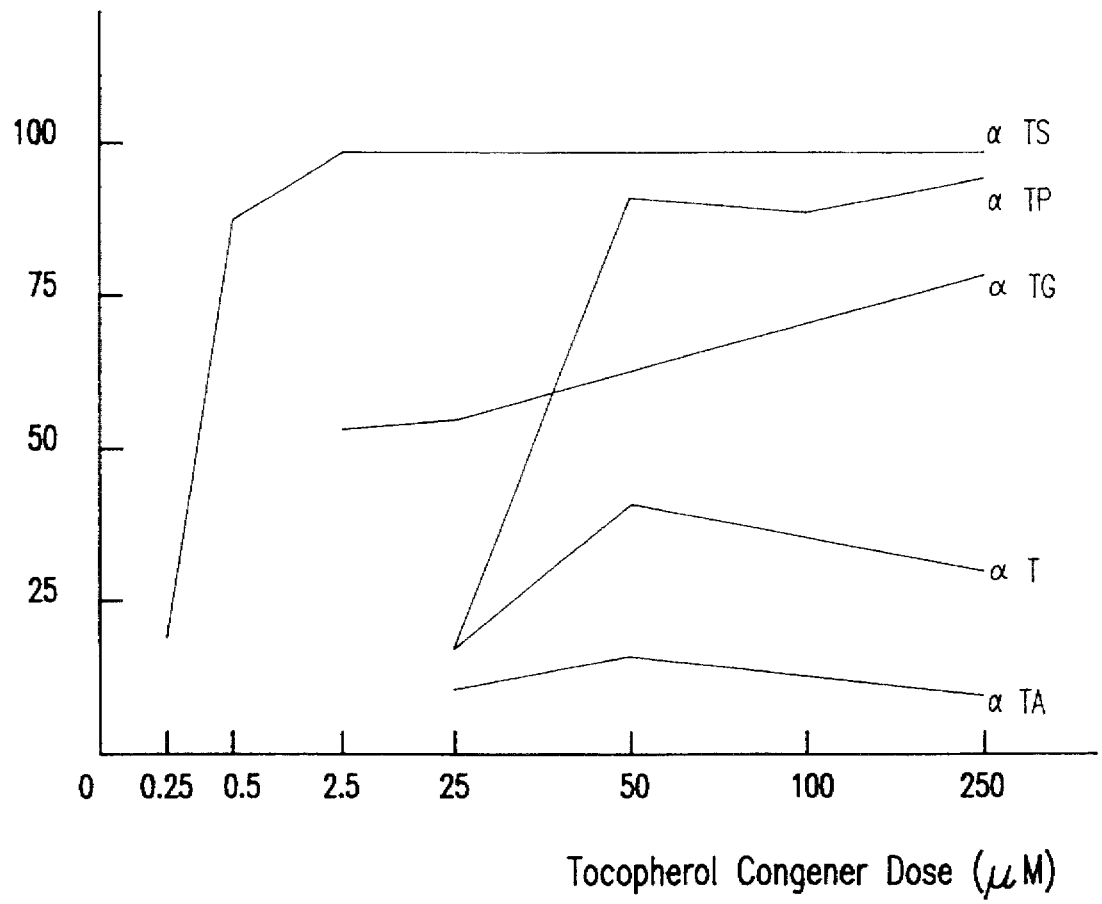
FIG. 3 is a graph showing the dose response of tocopherol congeners for protection of hepatocytes from EMS toxicity.

To determine the relative cytoprotective potency of various tocopherol derivatives, the effect of varying doses of a tocopherol analog on the protection against EMS-induced toxicity was examined in vitro on rat hepatocyte suspensions. Specifically, the following ionizable tocopherol congeners were tested: alpha-TS, alpha tocopheryl glutarate (alpha-TG), and alpha tocopheryl phosphate (alpha-TP). FIG. 3 shows a graphical representation of the percentage cytoprotection achieved with varying doses of the tocopherol derivatives. The response of varying quantities of alpha-T and alpha-TA are also represented on FIG. 3. Alpha-TS has the greatest potency With 100% protection against the loss of viability and metabolic performance observed at concentrations as low as 2 μM. At 2 μM, the cellular alpha-TS content was approximately 0.1 nmoles/10$^6$ cells or 10 nmoles/gram of tissue. With 0.5 μM alpha-TS, substantial (85%) protection against loss of viability was observed. At 0.5 μM, the cellular alpha-TS content is approximately 0.025 nmoles/10$^6$ cells. 0.1 nmoles is the lower detection limit. Since there are approximately 10$^8$ cells per gram of tissue, cytoprotection can be afforded by administering an appropriate amount of alpha-TS to a patient to achieve a 2.5 nmoles/gram concentration. Protection was not afforded hepatocytes incubated with alpha-T or alpha-TA at concentrations up to 250 μM. Significant protection against EMS toxicity was observed at alpha-TP medium concentrations of 50 μM and above. Possible explanations for the difference in potency observed between alpha-TS and alpha-TP are that the latter derivative was administered as water soluble salts in saline.

To confirm the cytoprotective properties of alpha-TP under physiological conditions in vitro tests using primary cultures of adult rat hepatocytes were conducted (another in vitro model system). Unlike the hepatocyte suspensions used for the in vitro modeling discussed above, cultured hepatocytes retain their in vivo cuboidal shape as a result of attachment to a collagen matrix, and their lifespan in vitro is 5 to 7 days, instead of 8–12 hours (as with suspensions). Table 10 shows the percentage cell death observed and the lipid peroxidation as measured by malondialdehyde (MDA) production observed with varying concentrations of the disodium salt of alpha-TP.

TABLE 10

Protective Effect of dl-Alpha-Tocopheryl Phosphate on Chemical Induced Toxicity and Lipid Peroxidation in Cultured Rat Hepatocytes.

| Incubation Conditions (6 hrs.) | | Cell Death (%) | Lipid Peroxidation |
|---|---|---|---|
| Negative Control (Vehicle Only) | | 10 ± 1 | 2.3 ± 0.3 |
| Positive Control (50 mM EMS Only) | | 61 ± 8 | 9.4 ± 1.1 |
| EMS + dl-alpha-TP | 25 μM | 16 ± 3 | 2.5 ± 0.9 |
| | 100 μM | 15 ± 3 | 2.3 ± 0.1 |
| | 250 μM | 20 ± 3 | 1.7 ± 0.1 |

Lipid peroxidation reported as μmoles MDA/$10^6$ cells

Table 10 shows that cultured hepatocytes are completely protected from the toxic effects of EMS by alpha-TP (≧25 M). Furthermore, alpha-TP treatment also prevented EMS-induced lipid peroxidation. These results are similar to those observed in hepatocyte suspensions for both alpha-TS and alpha-TP, and indicate that alpha-TP, like alpha-TS is indeed a potent cytoprotective agent with unique anticytotoxic properties. Interestingly, like alpha-TS, alpha-TP mediated cytoprotection is eliminated by increasing the extracellular $Ca^{2+}$ concentration to 3.5 mM from the physiological conditions of approximately 1 mM.

Alpha-TS has been found to be beneficial for tissue injury repair in human beings. In one case, the middle knuckle of the left hand of a 42 year old woman was injured by the removal of a small wart with liquid nitrogen. Two months following the liquid nitrogen insult, the injured area (approximately 1 cm in diameter) was characterized by scar tissue raised several millimeters above the surrounding normal skin. At this time, the lesion was treated by wetting the injured area with alpha-TS dissolved in dimethyl sulfoxide (100 mg/ml), daily for a period of two weeks. This treatment resulted in the rapid healing of the injured area with the elimination of scar tissue. One year following the last alpha-TS treatment, the once injured area remains indistinguishable from the surrounding normal tissue. In another case, a 42 year old woman's lip was severely sunburned. Topical lip cremes and antibiotic cremes were used for several weeks following the ultraviolet insult with minimal therapeutic benefit. At this time, the lesion was treated by wetting the injured area with alpha-TS dissolved in dimethyl sulfoxide (100 mg/ml) daily for a period of 1 week. This treatment resulted in the rapid healing of the lip without scar formation. In another case, the arch of the left foot of a 42 year old woman was inflamed and blistered from contact dermatitis or stress dermatitis. Six months after unsuccessful treatment on this lesion with betamethasone, the injured area was treated by wetting the injured area with alpha-TS dissolved in dimethyl sulfoxide (100 mg/ml) twice daily for a period of 1 week. This treatment resulted in the rapid healing of the foot lesion with the dissolution of both inflammation and blisters. Since dimethyl sulfoxide does not affect wound healing (See Goldblum, *Proc. Soc. Exper. Biol. Med.*, 172:301, (1983)) the cases described above suggest that alpha-TS applied topically is beneficial in repairing dermal injuries from a variety of insults. It is also evident from these cases that alpha-TS is the active component that promotes wound healing and prevents scar formation.

The above studies prove an intact ionizable tocopheryl congener (such as alpha-TS or alpha-TP) is required for cytoprotection. Protecting the ionizable tocopheryl congener from hydrolysis and esterase activity may be a critical concern during administration. The experimental results show that intravenous, intraperitoneal and dermal routes allow cellular accumulation of the intact ionizable tocopheryl congener. Other routes that would be effective for the cellular delivery of an ionizable tocopheryl congener would include subcutaneous injection, intramuscular injection, intrathecal injection, ocular administration (eye drops), sublingual administration, nasal spray administration, transdermal administration (with transdermal patches), and rectal administration (suppository). Coating the cytoprotective molecule with an impermeable polymer membrane that is not susceptible to the action of digestive enzymes (duodenal esterases) or is biodegraded very slowly should allow the ionizable tocopheryl congener to be taken orally (See, Safran et al., *Science* 233:1081 (1986) and Damage et al., *Diabetes* 37:246 (1988) for a discussion of protective coatings). In addition, amino acid polymers such as polylysine could be used. Impermeable polymer films would be degraded by microflora found in the colon. Thus, the ionizable tocopheryl congener contained therein would be released in a part of the intestine devoid of secreted digestive enzymes.

The acute administration of alpha-TS results in cytoprotection, in contrast to cells treated with alpha-T. Varying concentrations of alpha-T and alpha-TS were used to pretreat rat hepatocytes. The hepatocytes were subsequently exposed to 50 mM EMS for three hours. Table 11 presents the concentrations of alpha-T and alpha-TA as well as the protection from toxic injury observed.

TABLE 11

Effect of Tocopherol Analog Dose on the Concentration of Alpha-T and Alpha-TS and on Cytoprotection in Rat Hepatocytes Exposed to EMS for 3 Hours

| Treatment | | Hepatocyte Concentration[a] in nmol/$10^6$ cells | | Protection From Toxic Injury |
|---|---|---|---|---|
| | | Alpha-T | Alpha-TS | |
| Control | | 0.2 ± 0.1 | N.D. | No |
| Alpha-T | 25 μM | 2.1 ± 0.7 | N.D. | No |
| | 50 μM | 6.1 ± 0.7 | N.D. | No |
| | 250 μM | 23.7 ± 2.4 | N.D. | No |
| Alpha-TS | .5 μM | 0.2 ± 0.1 | N.D. | Yes |
| | 2.0 μM | 0.4 ± 0.1 | 0.2 ± 0.1 | Yes |

TABLE 11-continued

Effect of Tocopherol Analog Dose on the
Concentration of Alpha-T and Alpha-TS and on
Cytoprotection in Rat Hepatocytes Exposed to EMS for
3 Hours

| Treatment | | Hepatocyte Concentration[a] in nmol/10[6] cells | | Protection From Toxic Injury |
|---|---|---|---|---|
| | | Alpha-T | Alpha-TS | |
| | 10 µM | 0.8 ± 0.1 | 0.7 ± 0.1 | Yes |
| | 25 µM | 0.9 ± 0.1 | 2.5 ± 0.1 | Yes |
| | 250 µM | 0.9 ± 0.1 | 7.6 ± 1.7 | Yes |

[a]Expressed as X ± SEM, N = 3
N.D. Not Detected. Limits of detection are 0.05 nmol/10[6] cells for alpha-T and 0.1 nmol/10[6] cells for alpha-TS The exposure of rat hepatocytes to high concentrations of alpha-tocopherol (250 µM) results in a greater than 100 fold increase in cellular alpha-tocopherol levels (23.7 nmol/10[6] cells); however, the cells are not protected against the EMS toxic insult. Cytoprotective concentrations of alpha-TS resulted in only a slight increase in the cellular alpha-tocopherol content. Therefore, it can be concluded that acute administration of alpha-T is not cytoprotective. This lack of protection may be related to the lipophobic nature of alpha-T and to its inability to distribute to intracellular membranes. Thus, it appears that alpha-TS can rapidly distribute to intracellular membranes while alpha-T can not.

In vitro experiments were conducted with a variety of different tocopherol and succinate analogs to determine which were protective against EMS induced toxicity. After five hours of incubation with 50 mM EMS and 25 µM of a tocopherol or succinate analog, cytoprotection was determined by comparing the percentage of LDH leakage from control hepatocytes (vehicle only, assumed 100% protection) with the EMS only treated cells (assumed 0% protection). The results shown in Table 12 are obtained from three to eight separate hepatocyte preparations.

TABLE 12

Protective Effect of Tocopherol and Succinate
Analogs on EMS-Induced Toxicity in Rat Hepatocytes

| Administered Tocopherol or Succinate Analog (25 µM) | Percent Cytoprotection |
|---|---|
| Vehicle Control | 100 ± 9 |
| EMS Only | 0 ± 17 |
| Alpha-Tocopherol | 8 ± 10 |
| Alpha-Tocopherol + Succinic Acid | 26 ± 3 |
| Succinic Acid | 0 ± 23 |
| Alpha-Tocopherol Succinate | 92 ± 3* |
| Alpha-Tocopherol Succinate, K[+] Salt | 97 ± 3* |
| Alpha-Tocopherol Succinate Polyethylene Glycol (PEG) Ester | 80 ± 15* |
| Alpha-Tocopherol 3-Methyl Succinate | 70 ± 9* |
| Alpha-Tocopherol Succinate Methyl Ester | 22 ± 15 |
| Alpha-Tocopherol Succinamide | 0 ± 11 |
| Alpha-Tocopherol Glutarate | 55 ± 15* |
| Delta-Tocopherol Succinate | 70 ± 24* |
| Delta-Tocopherol | 0 ± 11 |
| Cholesteryl Succinate | 30 ± 22 |
| Cholesterol | 30 ± 16 |

*P < .05, as compared to EMS only treatment group

Table 12 shows that 25 µM of an ionizable tocopheryl congener (alpha-TS, K[+] salt of alpha-TS, alpha-TG, PEG ester of alpha-TS, and delta-TS) were protective against 50 mM EMS-induced toxicity in vitro. If the ionic nature of the congener is altered (i.e., methyl ester of alpha-TS or alpha-tocopheryl succinamide) the cytoprotective properties are diminished or eliminated. Alpha-tocopherol monoglutarate was prepared by the following synthesis. To 2.3 g (5.3 nM) of alpha-tocopherol was added 1.4 g (12.4 nM) of glutaric anhydride and 0.123 g (0.89 nM) of anhydrous potassium carbonate. The mixture was stirred and heated at 150°–160° for four hours. The mixture was cooled, dissolved in chloroform and passed through a silica column for purification. Of the twenty fractions which were collected, fractions ten through sixteen contained 3.0 g of the desired alpha-tocopherol mono glutarate. The presence of alpha-tocopherol monoglutarate was confirmed by TLC, NMR, and HPLC. TLC showed Rf=0.47 (chloroform-methanol 9:1) (By comparison with alpha-tocopherol mono succinate which has and Rf=0.33 in chloroform-methanol 9:1). NMR showed no aromatic protons, the protons of the carboxylic acid showed a broad peak at 4.5–5.8, the three —CH$_2$— (alkyl) groups of the glutaric acid showed multiplets and triplets at 2.4 and 2.9, the remaining peaks of the NMR are similar to those shown by alpha-tocopherol itself. HPLC showed base hydrolysis liberating greater than 95% of the expected concentration of alpha-tocopherol. Alpha tocopherol-3-methyl succinate was prepared by using the same molar quantities of reactants and catalysts as used in the alpha-tocopherol monoglutarate preparation except methylsuccinic anhydride was used in place of the glutaric anhydride. Heating temperatures and times as well as purification were similar. The presence of alpha-tocopherol 3-methyl-succinate was confirmed by TLC, NMR, and HPLC. TLC showed Rf=0.33 in chloroform-methanol 9:1. NMR showed no aromatic protons, the proton of the carboxylic acid group showed a very broad peak between 5 and 7, the remaining peaks are very similar to alpha-tocopherol monosuccinate with major peaks as follows: a doublet at 0.85, a multiplet at 1.0–2.6, a triplet at 1.6–1.9, a multiplet at 1.9–2.2, and a multiplet at 2.2–3.5. HPLC base hydrolysis liberated greater than 95% of the expected concentration of alpha-tocopherol. Delta-tocopherol mono succinate was prepared by using the same molar quantities of reactants and catalysts as used in the alpha-tocopherol mono glutarate preparation except delta tocopherol was used in place of alpha tocopherol and succinic anhydride was used in place of glutaric anhydride. Heating temperatures and times as well as purification were similar. The presence of delta-tocopherol mono succinate was confirmed by TLC, NMR, and HPLC. TLC showed Rf=0.37 in chloroform:methanol 9:1. NMR showed two aromatic protons at 6.65 and at 7.35. The proton of the carboxylic acid group spread widely. The main peaks are a doublet at 0.85, a multipier at 1.0–2.0, a singlet at 1.15, and a multipier at 2.5–3.0. HPLC base hydrolysis liberated greater than 95% of the expected concentration of delta-tocopherol.

FIGS. 4a and 4b show the structure versus activity correlation between the chemical nature of a tocopheryl congener and its cytoprotective potency (as derived from the in vitro results indicated in Table 12). From FIGS. 4a and 4b it can be concluded that cytoprotection may be related to the ionic nature of the ester congener. Optimal cytoprotection is observed when the ionic nature of the ester functional group (i.e. succinate) is maintained following attachment to tocopherol. By eliminating the ester (e.g., alpha-T) or the ionic nature of this functional group after esterification with tocopherol (e.g., alpha-TA, methyl ester of alpha-TS, or alpha-T succinamide) cytoprotective properties of the compound are dramatically reduced. Ionizable functional groups include the following anions: hydroxyls, carboxylic acids, sulfates, phosphates, thiols and selenic acids, and the following cations: amines.

An in vitro experiment with rat hepatocyte suspensions was performed to determine the effect of esterase inhibitors on alpha-TS. Table 13 shows the percentage of cell death resulting from treating the hepatocytes with 50 mM EMS and with two potent esterase inhibitors, diethyl-p-nitrophenyl phosphate (DENP) and Bis-(p-nitrophenyl) phosphate (BNPP).

TABLE 13

Effect of Esterase Inhibitors on Alpha-TS Mediated Protection in Hepatocyte Suspensions Exposed to EMS (1) 50 mM EMS (2) 25 µM alpha-TS
(3) 100 µM Diethyl p-nitrophenyl phosphate
(4) 100 µM Bis-(p-nitrophenyl) phosphate

| Incubation conditions | Cell Death (%) | % Initial Intra- cellular [K+] | nmoles/10⁶ cells Cellular alpha-T | nmoles/10⁶ cells Cellular alpha-TS |
|---|---|---|---|---|
| Control | 26 ± 4 | 93 ± 9 | .26 ± .05 | N.D. |
| (1) | 61 ± 5 | 27 ± 13 | .18 ± .05 | N.D. |
| (1) + (2) | 30 ± 7* | 93 ± 11* | .81 ± .05* | 2.73 ± .67 |
| (1) + (2) + (3) | 58 ± 8 | 26 ± 2 | .19 ± .05 | 2.56 ± .24 |
| (1) + (2) + (4) | 52 ± 3 | 14 ± 6 | .20 ± .05 | 2.61 ± .61 |

N.D. — not detected.
*$P \leq 0.01$, n = 3; as compared to EMS treatment.

As expected from the earlier experiments, alpha-TS administration protected hepatocytes against EMS-induced cell injury and death. However, when cells were pretreated with an esterase inhibitor prior to alpha-TS administration and EMS exposure, the protective effect of alpha-TS and the release of alpha-tocopherol were abolished. These data suggest that by preventing the release of alpha-tocopherol and succinate from alpha-TS, the cytoprotective properties of alpha-TS can be reduced. Because previous experiments demonstrated that cellular alpha-T accumulation is not cytoprotective, these data indicate that the cellular release of succinate from alpha-TS may be partially responsible for alpha-TS mediated cytoprotection.

It is well known that the succinate molecule is utilized by the cell to produce ATP energy. In the tricarboxylic acid cycle, succinate is oxidized by succinate dehydrogenase to produce ATP. Oxidation occurs in the mitochondria and the mitochondria can utilize both succinate formed in the mitochondria or succinate transported to the mitochondria. Increasing ATP production may enhance cellular repair processes as well as normal metabolic processes. For example, the cell's ability to remove free intracellular $Ca^{2+}$ during a toxic insult is related to ATP production. Succinate administration stimulates gluconeogenesis to form glucose 6-phosphate which is used for producing energy anaerobically (ATP formation through glycolysis) and for producing reducing equivalents (NADPH formation through the hexose monophosphate shunt needed for lipid and nucleotide biosynthesis and other biosynthetic reductions and enzymatic reactions, e.g., glutathione reductase). An in vitro experiment was conducted to determine the relationship between the release of succinate from alpha-TS and the cellular ATP level. The experiment was performed by incubating a tocopherol analog in a rat hepatocyte suspension and measuring the ATP level at the beginning and end of the test. Table 14 shows the ATP levels measured for a six hour incubation.

TABLE 14

Effect of Tocopherol Analogs and Succinate on the ATP Content of Hepatocyte Suspensions During a 6 Hour Incubation

| Incubation Conditions | Cellular ATP (nmoles/10⁶ cells) 0 Hr | Cellular ATP (nmoles/10⁶ cells) 6 Hr | Rate of ATP Depletion in (nmoles/10⁶ cell/hr) |
|---|---|---|---|
| Vehicle Control | 14.9 ± 1.6 | 5.0 ± 0.4 | 1.6 ± 0.2 |
| Alpha-TS 25 µM | 20.1 ± .5 | 14.2 ± 0.8* | 1.0 ± 0.1* |
| 250 µM | 15.2 ± 1.6 | 11.7 ± 2.0* | 0.6 ± 0.3* |
| Alpha-T 25 µM | 15.2 ± 1.6 | 6.3 ± 0.8 | 1.5 ± 0.2 |
| Alpha-TP 25 µM | 15.2 ± 1.6 | 6.3 ± 0.8 | 1.5 ± 0.2 |
| Succinate 50 µM | 19.4 ± 1.6 | 7.3 ± 0.2 | 2.0 ± 0.2 |
| 25 µM | 15.7 ± 1.3 | 4.9 ± 0.6 | 1.8 ± 0.2 |

*$P \leq 0.05$, n = 3; as compared to control

Control hepatocytes, which did not experience a toxic insult, lose approximately 65% of their endogenous ATP stores during a 6 hour incubation. Alpha-TS administration prevented rapid depletion of intracellular ATP. Succinate and alpha-tocopherol administration did not slow the depletion of intracellular ATP. Contrasting this data with that of Table 12, alpha-TS is cytoprotective and succinate and alpha-T are not. However, alpha-TP, which is cytoprotective, did not slow the depletion of intracellular ATP.

In vitro experiments have been conducted to determine the cytoprotective activity of succinate derivatives on EMS induced toxicity. Rat hepatocyte suspensions were subjected to 50 mM EMS and the percentage of cell death, the percentage of intracellular K+ (a metabolic parameter as discussed above), the depletion of ATP and the effect on lipid peroxidation were monitored. Table 15 shows the results obtained for rat hepatocyte suspensions pretreated with different succinate derivatives.

TABLE 15

Effect of Succinate Derivatives on EMS induced Toxicity in Rat Hepatocyte Suspensions (1) 50 µM EMS (2) 25 µM alpha-TS
(3) 50 µM methyl ester of alpha-TS
(4) 100 µM Cholesteryl Succinate
(5) 250 µM Monomethyl Succinate
(6) 250 µM Dimethyl Succinate

| Incubation Conditions (5 Hrs) | Cell Death (%) | % Initial Intracellular [K+] | % Initial Intracellular [ATP] | Lipid Peroxidation nmolMDA/ 10⁶ cells |
|---|---|---|---|---|
| Vehicle only | 24 ± 1 | 94 ± 2 | 64 ± 7 | 0.9 |
| (1) | 59 ± 1 | N.D. | N.D. | 14.4 |
| (1) + (2) | 27 ± 1** | 86 ± 6** | 45 ± 2** | 0.9 |
| (1) + (3) | 30 ± 1** | 67 ± 4** | — | — |
| (1) + (4) | 48 ± 4* | N.D. | — | 11.3 ± 4.2 |
| (1) + (5) | 61 ± 5 | N.D. | — | 12.8 ± 1.0 |
| (1) + (6) | 60 ± 1 | N.D. | — | 12.6 ± 0.2 |

N.D. — Not Detected
**$P \leq 0.01$, n = 3; as compared to EMS treatment alone.
*$P \leq 0.05$, n = 3; as compared to EMS treatment alone.

Treating hepatocytes with methyl esters of succinate did not provide the hepatocyte suspensions with protection from EMS induced injury, membrane lipid oxidation, or cell death. Concentrations as small as 25 μM of alpha-TS provides cytoprotection while concentrations as high as 250 μM of monomethyl succinate and dimethyl succinate were ineffective. Cytoprotection of the methyl ester of alpha-TS and cholestryl succinate appear to be dosage dependent (i.e., Table 15 shows the methyl ester of alpha-TS and cholesteryl succinate are cytoprotective at 50 μM and 100 μM, respectively, but Table 12 shows they are not cytoprotective at 25 μM). The methyl ester of alpha-TS is also capable of the cellular release of alpha-tocopherol and succinate. The methyl ester of alpha-TS and alpha-tocopheryl succinamide have increased lipophilicity and may prove useful in promoting the accumulation of alpha-TS and cytoprotection in the central nervous system.

Alpha-TS may provide a transport system and cellular reservoir for succinate. Alpha-T is a lipophilic, membrane-bound cellular protective component. It is sequestered in virtually all cells and tissues and is membrane bound in virtually every subcellular organelle. The largest accumulation of alpha-T is found in the mitochondria, endoplasmic reticulum and nucleus. Simon et al., *Fed. Proc.* 16:249 (1957), reported that alpha-TS administration in vivo results in alpha-TS accumulation in the membranes of the endoplasmic reticulum and mitochondria. The inventors results in Table 6 show that alpha-TS accumulation is detectable in the liver, kidney, brain, heart, lung, blood and plasma. Alpha-T could transport the succinate ester into the cell, whereupon esterases hydrolyze the ester to separate alpha-T and succinate. The diminished protection observed in vitro for cholesteryl succinate administration, reported in Table 15, probably is a result of the insoluble nature of cholesteryl succinate in its free acid form, thereby resulting in a reduced bioavailability of cholesteryl succinate (as also observed in vivo as best shown in Tables 26 and 27)

An in vivo experiment was performed to determine the effect of alpha-TS on the energy status of rat tissues. Male Sprague-Dawley rats were administered alpha-TS (100 mg/kg, single ip dose) or olive oil (vehicle only, 0.2 ml, single ip dose). Three rats were used per treatment. The rats fasted for 24 hours after ip dosage prior to sacrifice and analysis of tissues. Table 16 shows the effect of the administering alpha-TS on the energy status of rat tissue.

TABLE 16

Effect of alpha-tocopherol succinate (+) or Vehicle (−) Administration on the Energy Status of Rat Tissue

| Tissue | ATP (nmol/g) (−) Alpha-TS (+) | | Glucose (μmol/g) (−) Alpha-TS (+) | |
|---|---|---|---|---|
| Liver | 428 ± 127 | 458 ± 57 | 23.2 ± 10.8 | 21.7 ± 9.7 |
| Kidney | 390 ± 95 | 515 ± 44¹ | 4.1 ± 0.7 | 3.4 ± 1.1 |
| Heart | 2015 ± 483 | 2782 ± 868 | 8.7 ± 1.4 | 10.1 ± 1.7 |
| Lung | 247 ± 27 | 418 ± 18* | 4.2 ± 1.3 | 4.1 ± 0.5 |
| Brain | 112 ± 42 | 293 ± 86* | N.D. | N.D. |
| Blood | 224 ± 42 | 647 ± 29* | 6.0 ± 1.1 | 4.8 ± 0.3 |

| Tissue | Lactate (μmol/g) (−) Alpha-TS (+) | | Glycogen (μmol/g) (−) Alpha-TS (+) | |
|---|---|---|---|---|
| Liver | 3.07 ± .58 | 3.36 ± .20 | 179 ± 26 | 778 ± 98* |
| Kidney | 4.77 ± .66 | 3.10 ± .21* | 122 ± 50 | 211 ± 44¹ |
| Heart | 16.69 ± 1.56 | 10.84 ± 2.67* | 428 ± 49 | 4321 ± 946* |
| Lung | 2.06 ± .92 | 2.24 ± .29 | 168 ± 15 | 634 ± 133* |

TABLE 16-continued

Effect of alpha-tocopherol succinate (+) or Vehicle (−) Administration on the Energy Status of Rat Tissue

| Brain | 11.61 ± .60 | 7.82 ± .20* | 1425 ± 224 | 1396 ± 372 |
| Blood | 1.05 ± .34 | 1.68 ± .06* | 25 ± 1 | 117 ± 26* |

Results are expressed as X ± SE (n = 3), with tissue from each rat analyzed in triplicate. Three rats per treatment.
*p < .05, as compared to vehicle control
¹p < .1 as compared with vehicle control All of the organs tested were greatly affected by the administration of alpha-TS. Dramatic increases in ATP or glycogen levels were observed for all tissues and a dramatic decrease in tissue lactate levels were found in the kidney, heart and brain. Increases in tissue lactate levels have been suggested to promote tissue injury during toxic insults. The in vivo results may suggest that the potentiation of cellular energy status is responsible for the cytoprotective properties. The in vivo study confirms that all tissues and organ systems will benefit from ionizable tocopheryl administration.

In vivo experiments have been conducted with male Sprague-Dawley rats to determine particular tocopherol and succinate analogs which are cytoprotective. Several tocopherol and succinate analogs were tested for $CCl_4$ induced lethality. A single dose of the tocopherol or succinate analog was administered twenty four hours prior to orally administering 2.9 g $CCl_4$/kg body weight. Three to six animals were analyzed per treatment. The rats were monitored for seven days. Table 17 shows the days survived after treatment with $CCl_4$.

TABLE 17

Protective Effect of Tocopherol and Succinate Analogs on Carbon Tetrachloride Induced Lethality in Rats

| Tocopherol or Succinate Analog Administered | Days Survived After $CCl_4$ Treatment |
|---|---|
| Vehicle Control (Olive Oil) | 2 |
| Alpha-Tocopherol (100 mg/kg) | 3 |
| Succinic Acid (100 mg/kg) | 2 |
| Succinic Acid, Na Salt (1 g/kg) | 2 |
| Monomethyl Succinate (1 g/kg) | 2 |
| Dimethyl Succinate (1 g/kg) | 2 |
| Alpha-Tocopheryl Succinate (50 or 100 mg/Kg) | >7* |
| Alpha-Tocopheryl Succinate (25 mg/kg) | >7*[a] |
| Alpha-Tocopheryl Succinate, K⁺ Salt (100 mg/kg) | >7* |
| Alpha-Tocopheryl Succinate Methyl Ester (100 mg/kg) | >7*[a] |
| Alpha-Tocopheryl Succinate Polyethylene Glycol Ester (100 or 200 mg/Kg) | >7* |
| Alpha-Tocopheryl Succinate Polyethylene Glycol Ester (200 mg/Kg, iv) | >7* |
| Alpha-Tocopheryl Succinate Polyethylene Glycol Ester (200 mg/kg, oral) | 2[a] |
| Alpha-Tocopheryl 3-Methyl Succinate (100 mg/kg) | 2[a] |
| Alpha-Tocopheryl Glutarate (100 mg/kg) | 2 |
| dl, alpha-Tocopheryl Phosphate, Na Salt (100 mg/kg) | 3 |
| Cholesterol (100 mg/kg) | 2 |
| Cholesteryl Succinate (100 mg/kg) | >7* |

Figure 5A:
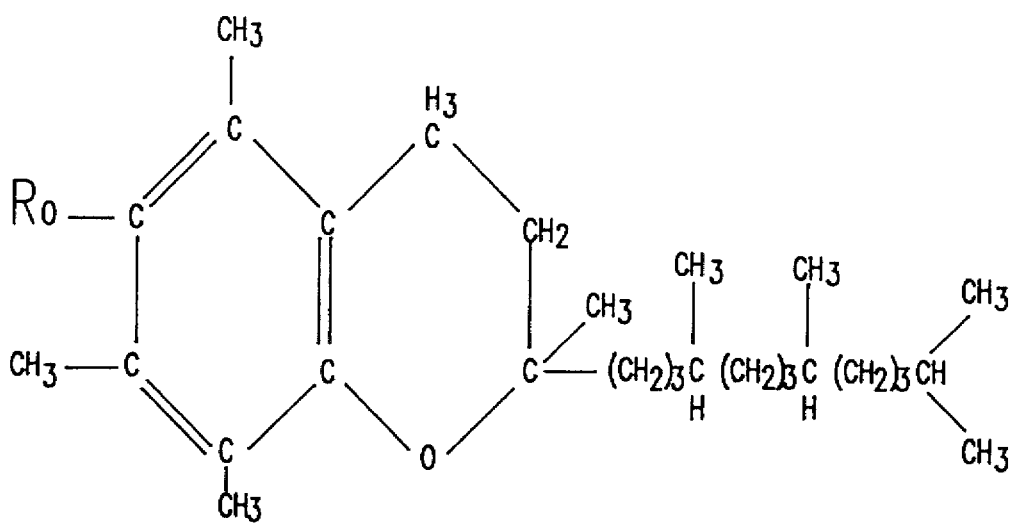

[a]two to three animals in group survived.
*P < .05, as compared to vehicle control Most of the analogs were administered intraperitoneally; however, PEG analogs dissolved in saline were administered intravenously or orally as well. Rats pretreated with cholesterol or the vehicle alone (olive oil) died within two days. In contrast, rats which received succinate esters of tocopherol and cholesterol were protected against the lethal effects of $CCl_4$. FIGS. 5a and 5b show the structure versus the activity for the analogs reported in table 17.

Table 18 shows the results of in vivo experiments where rats were orally given a 2.9 g $CCl_4$ g/kg body weight dose after fasting for twenty four hours. The survival of the rats in each category was monitored and an $LD_{50}$ value was calculated (greater than three rats in each category of treatment were used). Providing rats with a 100 mg/kg body weight i.p. dose of either alpha-TS or cholesteryl succinate twenty four hours prior to the $CCl_4$ dose protected the rats from death and the calculated $LD_{50}$ values for rats in both groups was 4.4 g $CCl_4$/kg. Table 18 also shows the SGOT levels (AST levels) for rats which were pretreated with some of the tocopherol and succinate analogs and were sacrificed 48 hours after receiving a 1.0 g/kg body weight oral dose of $CCl_4$. As discussed above, SGOT levels provide a clinical assessment of hepatotoxicity (liver damage). Contrasting the group of control rats which received vehicle alone (no $CCl_4$) with rats which received an i.p. dose of cholesteryl succinate, it can be seen that the cholesteryl succinate protected the rats from the hepatotoxic effects of $CCl_4$. This protection has been confirmed by histopathology.

Ionizable congeners of aromatic and aliphatic alcohols can be used for a variety of purposes which capitalize on their cytoprotective function such as the suppression and/or prevention of cancer, protection against the deficits induced by ischemic challenge (i.e., heart disease, stroke, and organ transplantation), protection against Alzheimer's and Parkinson's disease, protection against tissue-damaging effect of environmental pollutants, preservation of tissues, wound healing, suppression of the aging process, and protection against toxic therapeutic drugs. Normal tissue can be protected from damage induced by cancer therapeutic agents such as adriamycin, radiation, and the like, using ionizable congeners of aromatic and aliphatic alcohols. Ionizable congeners of aromatic and aliphatic alcohols also inhibit tumor cell growth and prevent the inducement of neoplasia in normal tissue. Ionizable congeners of aromatic and aliphatic alcohols can be used to preserve organs and blood that are stored for transplantation, facilitate the process of wound healing and lessen the likelihood of scarring, protect against premature aging of the skin induced by environmental factors such as the sun and wind, and protect body tissues against the "normal" process of degradation with age. Except for use in conjunction with wound healing and ischemic challenge, the ionizable congeners of aromatic and aliphatic alcohols are optimally administered prior to the toxic or degradative challenge (prophylactically).

Prasad and others have reported that alpha-TS administration (10 μM) inhibits tumor cell growth (mouse melanoma cells B-16; mouse neuroblastoma cells NBP2; human neuroblastoma cells; and human prostate cells in culture). In addition, it has been reported that alpha-TS has the ability to induce morphological differentiation in mouse melanoma cells so that the resultant new cells resemble normal melanocytes (a reversion from carcinogenic to normal tissue). Shklar and others have reported a dramatic regression in chemically-induced tumors (epidermoid carcinomas) of the hamster cheek pouch by local administration of alpha-TS. In all of the reported studies, it has been assumed that the antitumor effect of alpha-TS stems from the release of alpha-T from alpha-TS.

Figure 6:
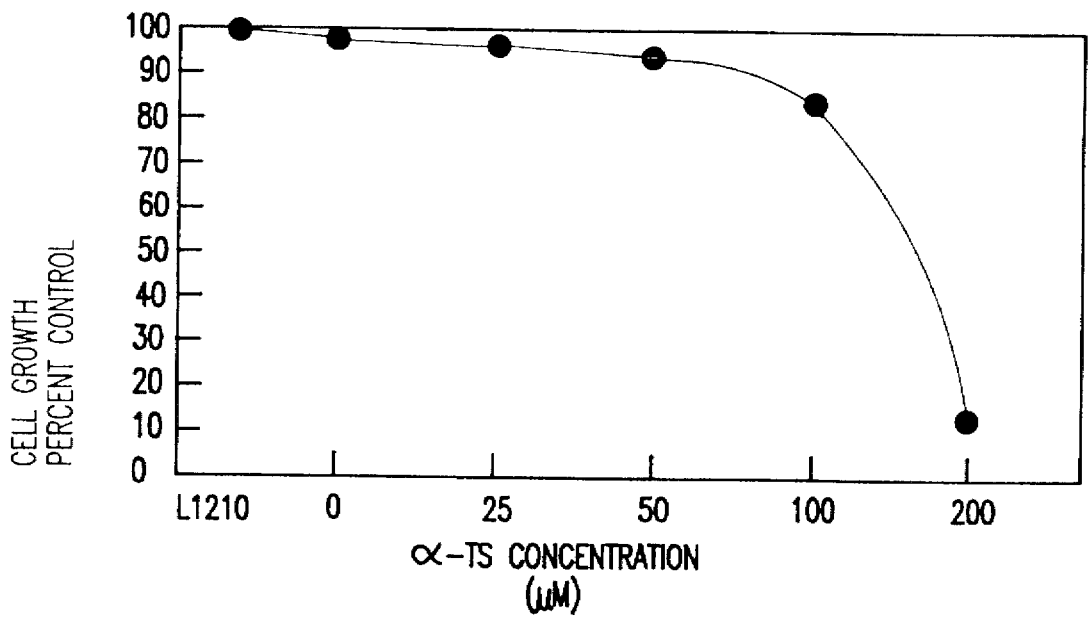
FIG. 6 is a graph showing the inhibition of L1210 murine leukemia cell growth in vitro with increasing concentrations of alpha-TS.
Figure 7:
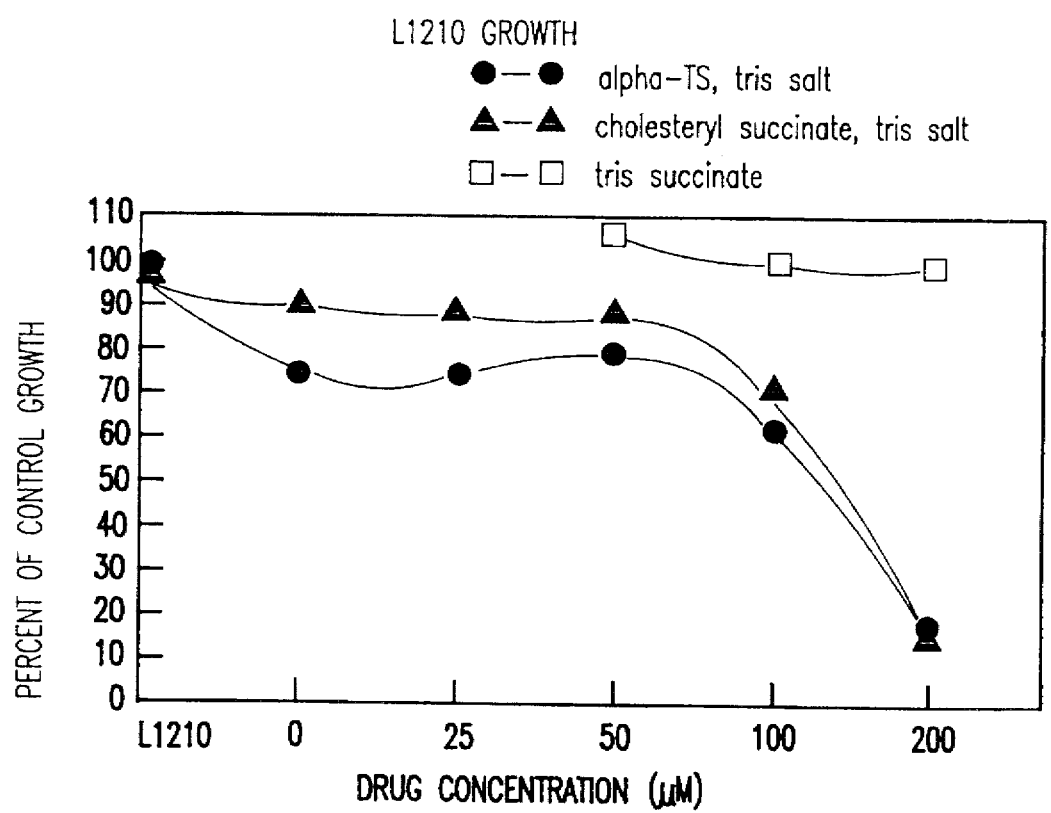
FIG. 7 is a graph showing the inhibition of L1210 murine leukemia cell growth cytotoxicity in vitro with increasing concentrations of alpha-TS tris salt and cholesteryl succinate tris salt and the lack of anticytotoxic activity of tris succinate, and the absence of an effect on tumor cell growth by tris succinate.

Experiments have been conducted in vitro and in vivo to examine the effect of alpha-TS on the growth of murine L1210 leukemia cells and these studies confirm the previous reports that alpha-TS administration inhibits tumor cell growth. These studies also show that cholesteryl succinate inhibits tumor cell growth and that the use of the tris salt of cholesteryl succinate and alpha-TS is advantageous over the free acid forms. FIG. 6 shows the dose response of alpha-TS on the growth of murine L1210 leukemia cells in suspension cultures where the L1210 cells were incubated in RPMI-1640 medium with 10% fetal bovine serum at a density of $0.5*10^5$ cells/ml and were treated with varying amounts of alpha-TS free acid or vehicle (ethyl alcohol) and were incubated for 72 hours followed by a cell number determination. It can be seen that alpha-TS (free acid) administration at concentration greater than 100 μM significantly suppresses the growth rate of L1210 cells. Similar in vitro experiments were conducted with cholesteryl succinate tris salt and alpha-TS tris salt. FIG. 7 shows that cholesteryl succinate tris salt and alpha-TS tris salt both significantly suppress the growth rate of L1210 cells, while tris succinate alone had no effect on the growth rate of these tumor cells. Table 19 shows that the administration of both alpha-TS tris salt and cholesteryl succinate tris salt (100 mg/kg body weight, i.p., single dose) in vivo results in a small, but significant, growth arrest of implanted murine L1210 leukemia cells in CDF1 mice as measured by enhanced survival time. In addition, the administration of alpha-TS tris salt and cholesteryl succinate tris salt did not damage normal tissue. Hence, the cytoprotective effect of alpha-TS is not related to the release of alpha-T, but do to the presence of the ionizable congener (cholesteryl succinate does not release alpha-T).

Dr. Borek and others have shown that alpha-TS protects a variety of cell types against the carcinogenic effects of radiation and cancer causing chemicals. These effects were attributed to the presence of tocopherol, despite the fact that other analogues of alpha-tocopherol, such as alpha-TA were ineffective in the same studies. Table 20 demonstrates that both alpha-TS and cholesteryl succinate protect in vivo tissues from the damage normally produced by the potent cancer-causing chemical $CCl_4$. Succinate analogs were administered to male Sprague-Dawley rats 20 hours prior to a 1 g $CCl_4$/kg body weight oral challenge and the AST and ALT serum enzyme levels were measured 48 hours after the challenge. Tris succinate did not provide protection against the $CCl_4$ challenge, nor did cholesteryl succinate tris salt when administered orally. Cholesteryl succinate tris salt and alpha-TS tris salt when administered by intraperitoneal injection provided protection against $CCl_4$ induced hepatotoxicity. The results also indicate that cholesteryl succinate is more cytoprotective than alpha-TS, a result which has not been previously shown. Hence, the ionizable congener of the aromatic and aliphatic alcohol is responsible for the cytoprotection, as opposed to the release of alpha-T.

Figure 8A:
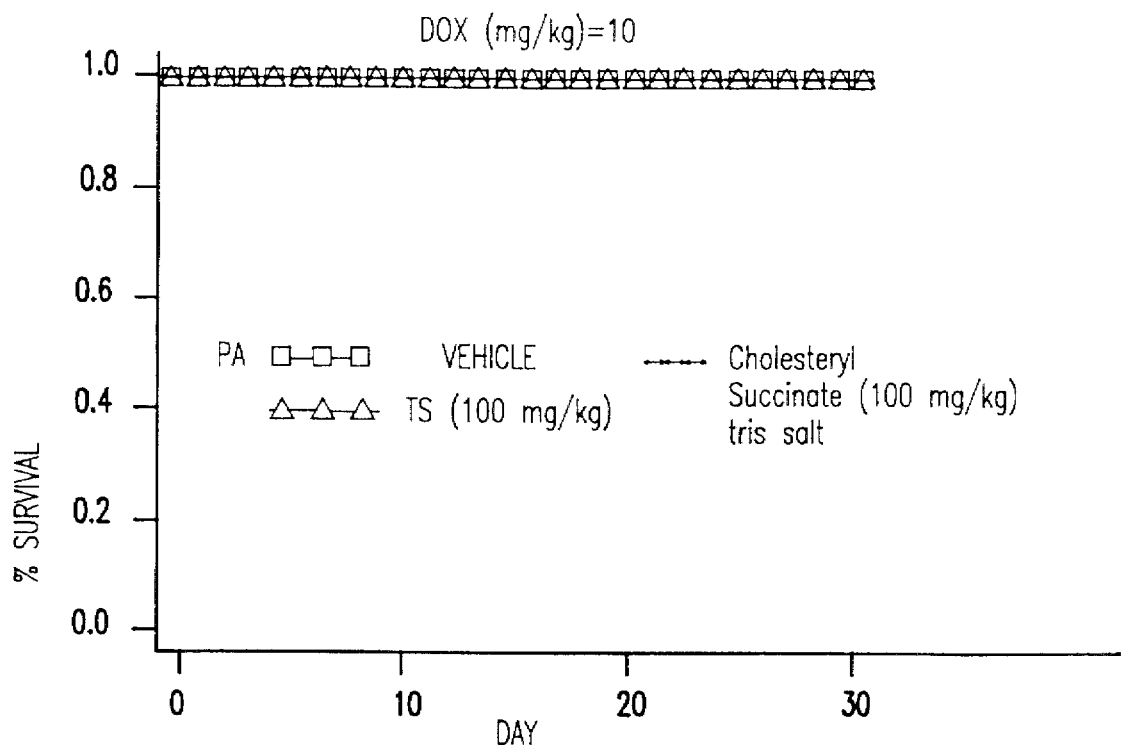
FIGS. 8a–d are graphs showing the in vivo protective effects of cholesteryl succinate and alpha-TS against doxorubicin for normal tissue.
Figure 8B:
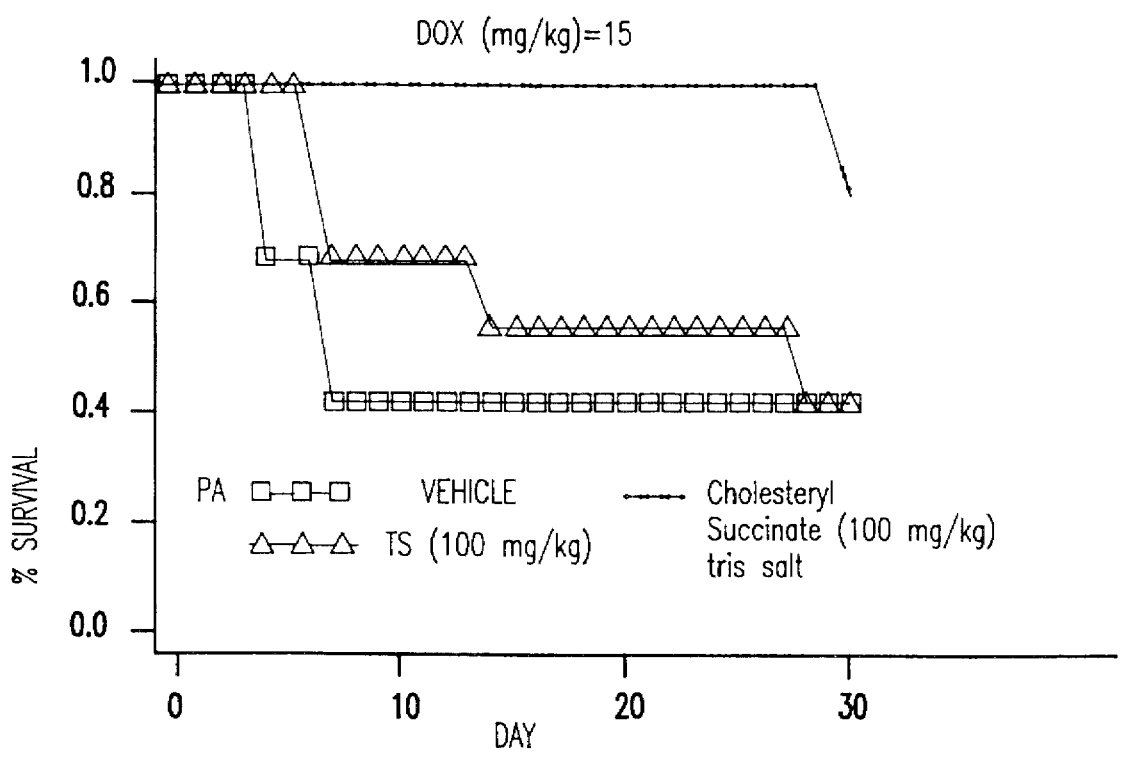
Figure 8C:
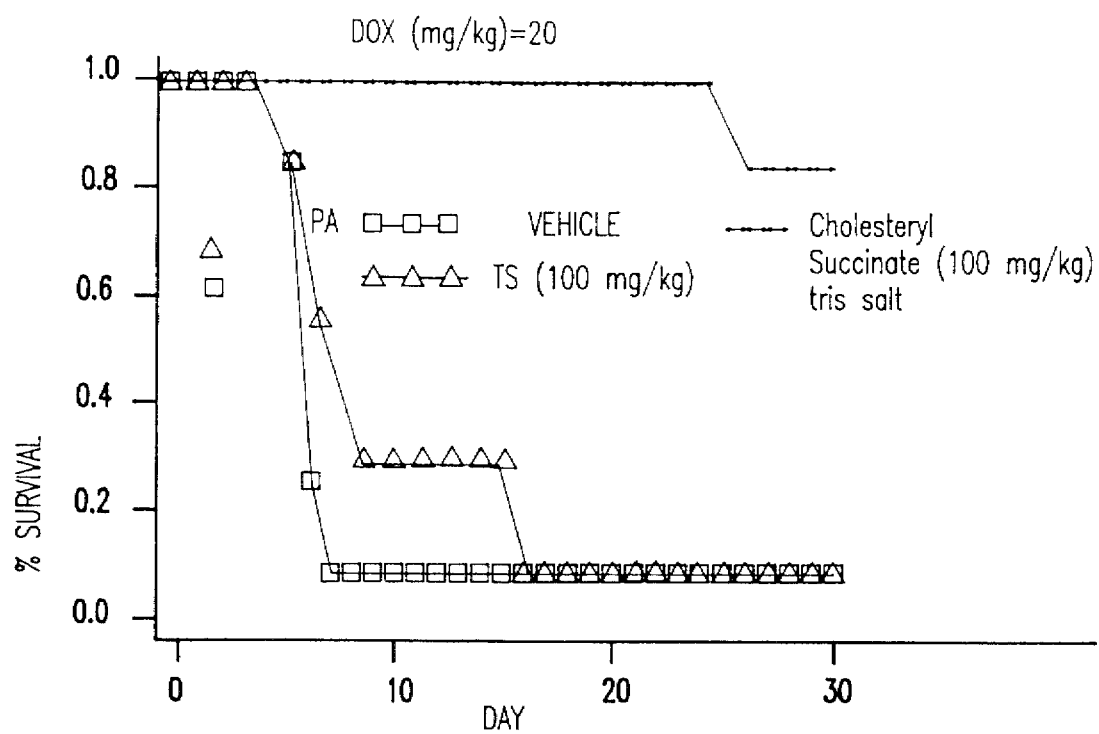
Figure 8D:
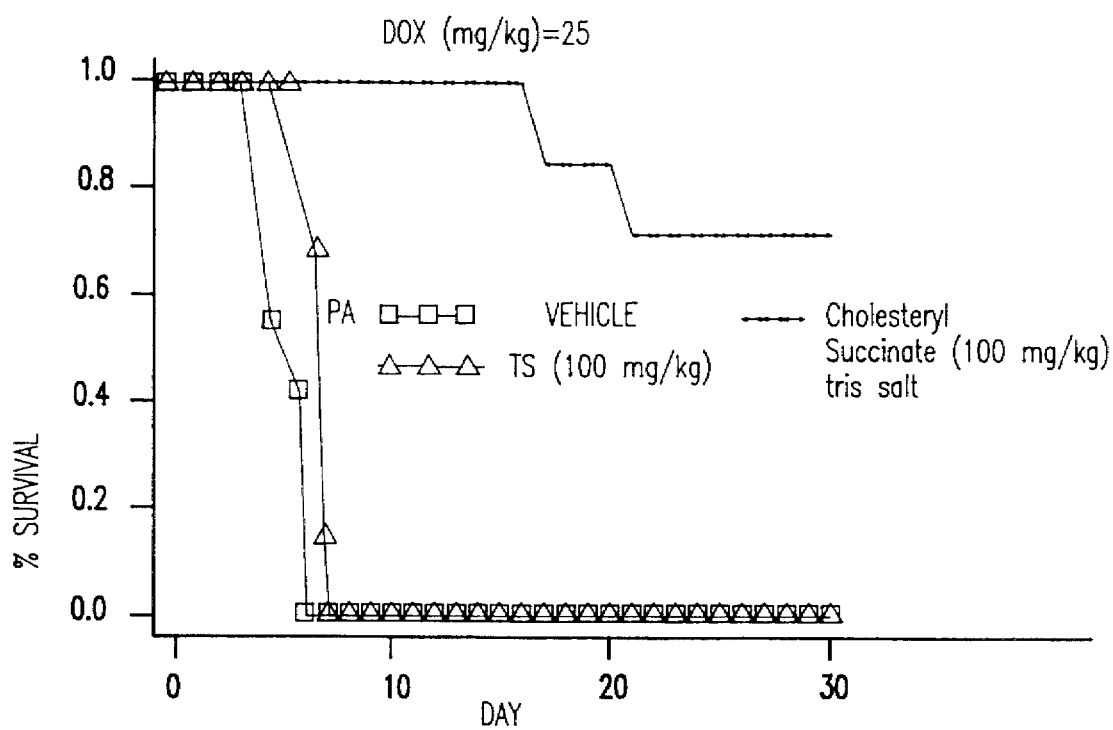
Figure 9A:
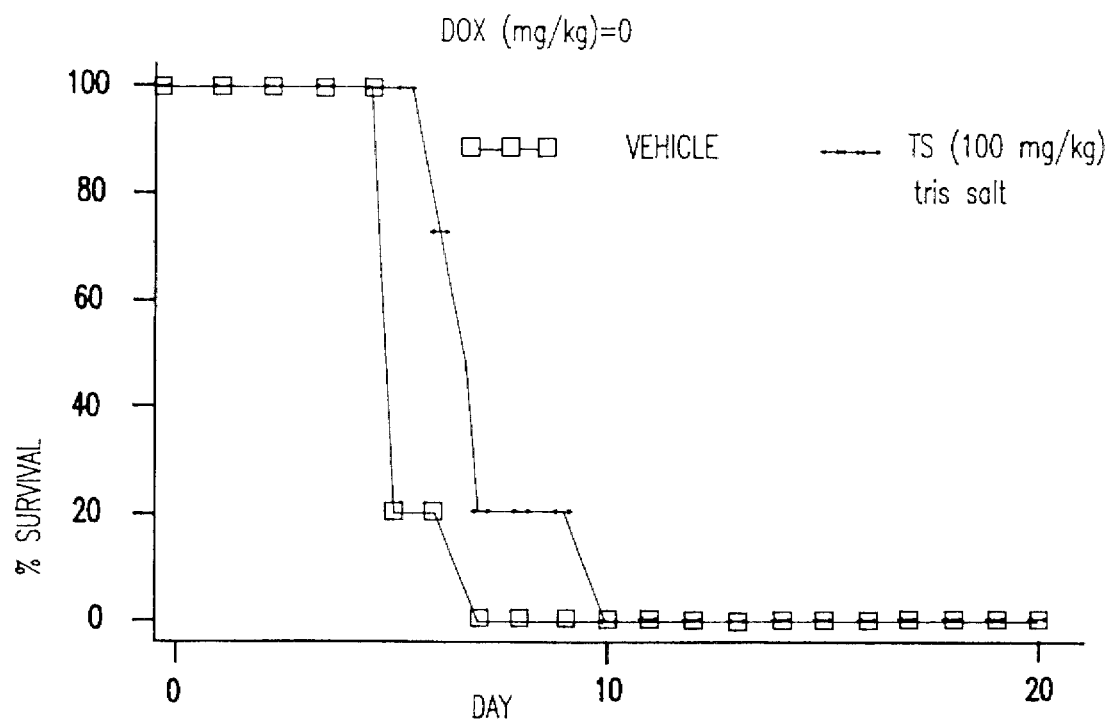
FIGS. 9a–d are graphs showing the in vivo effects of alpha-TS tris salt against doxorubicin for neoplastic tissue.
Figure 9B:
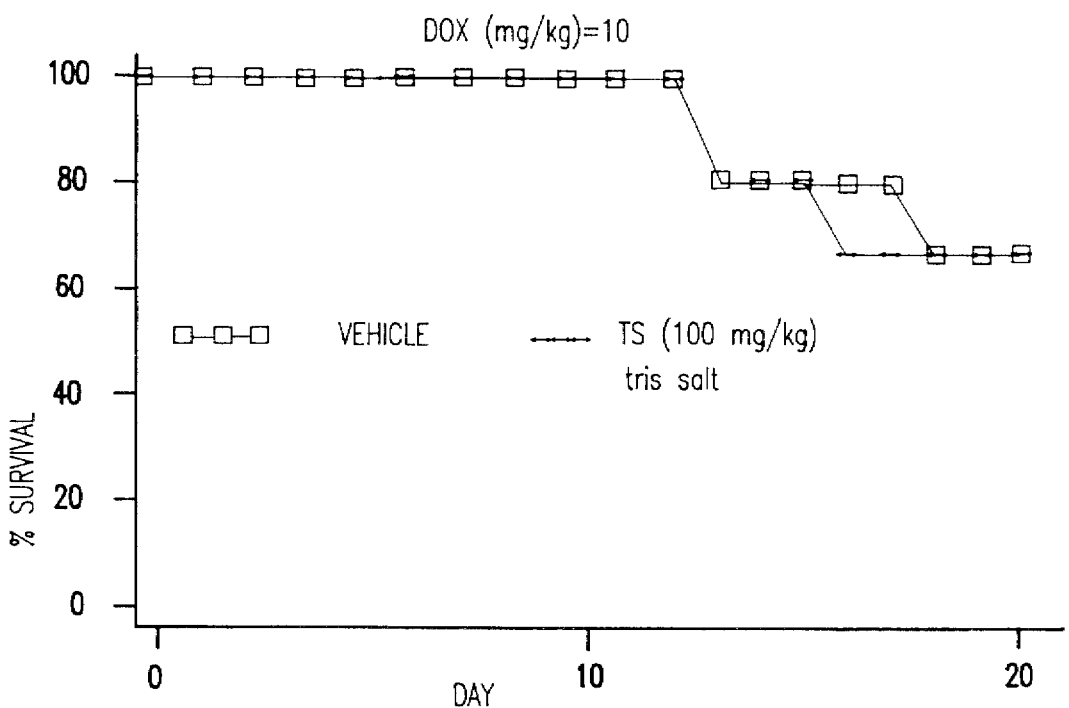
Figure 9C:
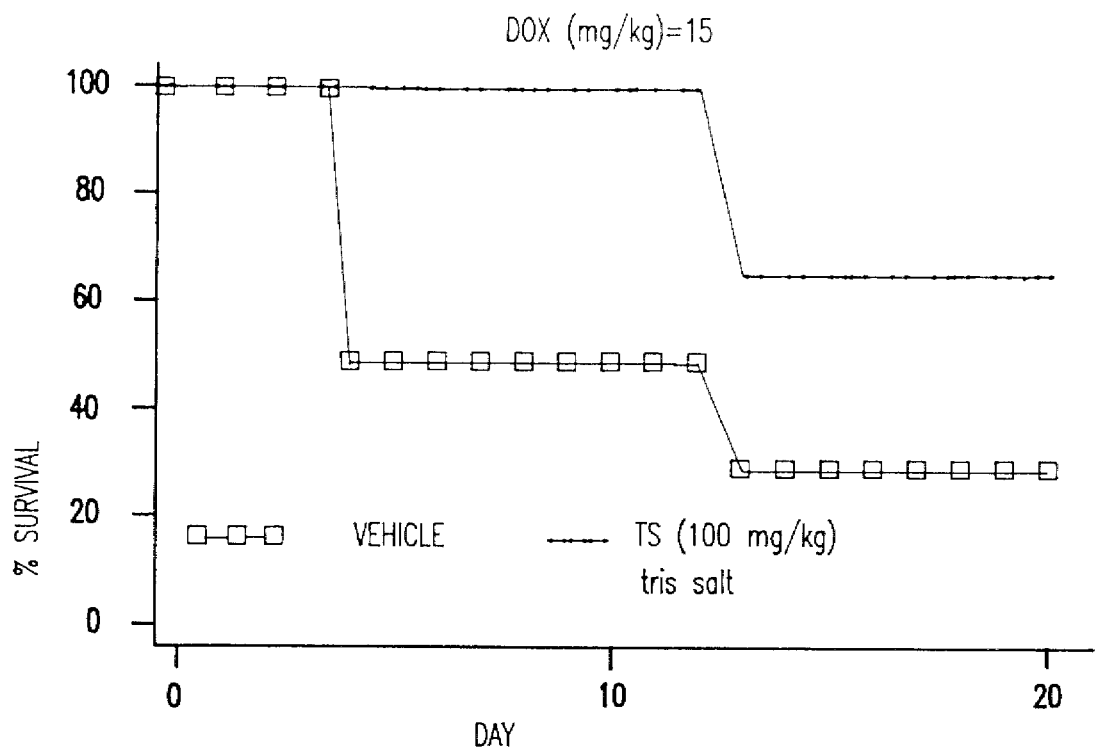
Figure 9D:
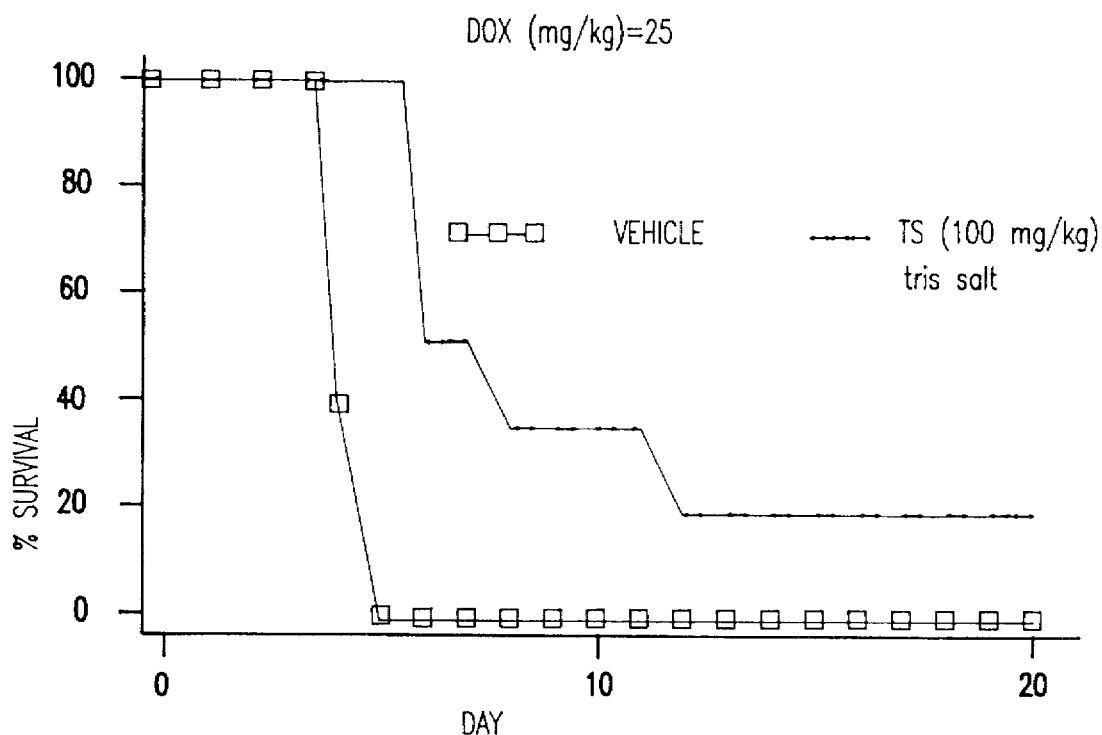
Figures 12A, 12B:
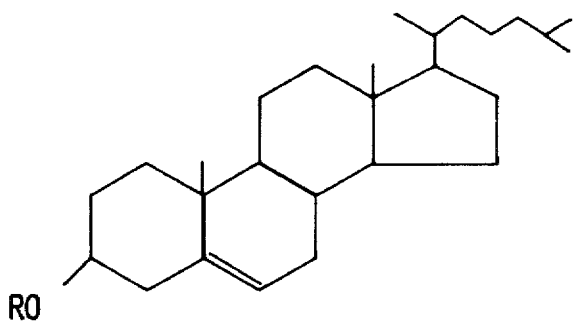
Figures 13A, 13B:
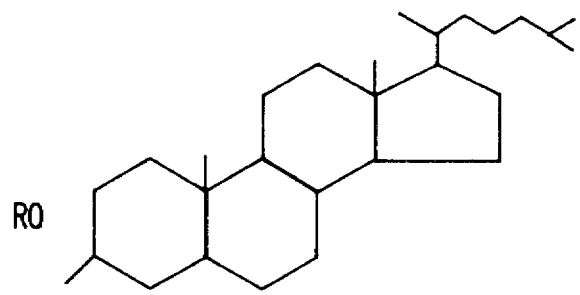

In vivo experiments have been conducted which show that both the alpha-TS and cholesteryl succinate tris salts protect normal tissues from doxorubicin (DOX, also called adriamycin which is an anti-tumor, anticarcinogenic agent). The experiments were conducted in accordance with NCI Protocol 1.100. FIGS. 8a–d show the experimental results obtained when male $CDF_1$ mice (n=6) received either vehicle only or 100 mg/kg body weight i.p. dose of either alpha-TS or cholesteryl succinate 20 hours prior to DOX administration. FIGS. 8a–d respectively show the results obtained when the mice received 10, 15, 20, and 25 mg DOX/kg body weight. The treated mice survived significantly longer than untreated mice or mice treated only with vehicle. Hence, it can be seen that alpha-TS and cholesteryl succinate protect normal tissues against the lethal effects of DOX and that cholesteryl succinate is more effective than alpha-TS. Further in vivo experiments have demonstrated that the protective activity of alpha-TS against the anticarcinogenic agent DOX does not occur in neoplastic tissues. FIGS. 9a–d show the experimental results obtained when male $CDF_1$ mice (n=1) were injected (j.p.) with $10^0$ murine L1210 leukemia cells followed immediately by an injection of alpha-TS tris salt (100 mg/kg, i.p.) or saline injection (vehicle), and twenty hours later (Day=0) each mouse in three of the groups was i.p. injected with 15, 20, or 25 mg DOX/kg body weight (FIGS. 8b–d, respectively). Survival was monitored for twenty days. FIG. 9a shows that tumor cells in the absence of DOX will kill both treated and untreated animals; however, reference back to Table 19 does show that combined administration of alpha-TS with tumor cells slightly, but significantly, increases the animals survival time (promotes the destruction of tumor cells). FIG. 9b shows that when the mice are given 10 mg/kg of the antitumor agent DOX, the survival of the tumor bearing mice is dramatically increased, however, the administration of alpha-TS appears to have no effect on the survival of DOX treated animals (indicating that alpha-TS does not protect tumor cells from the lethal effects of DOX). FIGS. 12c–d show that mice dosed with higher concentrations of DOX, e.g., 15 and 25 mg DOX/kg body weight, were provided with significant protection from DOX by the administration of alpha-TS (which supports the data presented in FIGS. 8b–d with normal tissues).

Additional experiments demonstrating that the compounds of the present invention are useful in the treatment and prevention of cancer. Three murine cell lines were used in this study: 1) L1210; a lymphocytic leukemia carried in vivo as a subcutaneous solid tumor in DBA female mice; 2) C1498; an acute myeloid leukemia, carried in vivo as an infected spleen of female C57BL/6 mice; 3) CFU-GM; normal bone marrow, collected from the tibia and femur bones of CDF1 male mice. In these experiments the effect of cholesterol succinate (CS), tocopherol succinate (TS), as well as their constitutive components tocopherol (T), cholesterol (C) and tris succinate, were evaluated with respect to the growth and viability of murine leukemia cells, C1498 and L1210 and normal bone marrow cells, CFU-GM. In addition, the nonhydrolyzable ethers, cholestreryloxybutyric acid (CSE) and tocopheryloxybutyric acid (TCE), were synthesized and examined for anti-tumor activity.

CSE and its tris salt were prepared according to the following procedures. 4-Hydroxybutanonitrile was prepared according to the modified method of Henry, "Uber die normalen cyanobutylalkohole", *Chemishes Zentralblatt*, 1:984, 1898, which is herein incorporated by reference, by heating at 130° for 4 hours, a mixture of 19 g (128 mM) 4 bromobutyronitrile with 15.6 g (159 mM) powdered anhydrous potassium acerated without a solvent. The 3-cyanopropyl acerated formed was extracted with chloroform and the chloroform was removed under reduced pressure to give 13.6 g (83%) of the crude acetate. This acetate was then treated with a mixture of 9.2 g (164 mM) pulverized KOH in 67 ml of methanol at 3°–5° C. for 24 hours. Concentrated HCl was then added dropwise until the mixture was acidic. The methanol and ome of the water was removed under reduced pressure and the remaining oily mixture was repeatedly extracted with chloroform. The extracts were combined and the chloroform was removed under reduced pressure. The remaining extract was dried by adding toluene and then distilling off the toluene/water azeotrope. The residue was distilled under reduce pressure to give 4-hydroxybutanonitrile, 6.1 g (67%), boiling point 132°–8° C./35 mm HG 9 Bp 140° C./30 mm Hg). The NMR and IR spectra of the product were consistent with the structure of 4-hydroxybutanonitrile.

In a round bottom flask, 1.3 g (15.3 mM) of 4-hydroxybutanonitrile, 6.34 g (11.7 mM) of cholesteryl p-toluene sulfonate and 10 ml of toluene were added. The mixture was stirred and heated at 120° C. for 5 hours. The solvent was removed under reduced pressure to give the crude nitrile as a thick, tan oil. This was hydrolyzed without further purification by adding 30 ml of isopropanol, 30 ml of 12% NaOH, and 2 g of solid NaOH. The mixture was warmed at 100° C. for 3 days to hydrolyze the nitrile. The solvents were removed under reduced pressure to give the crude sodium salt of the desired product and this was "washed" with 120 ml of ether, then with 20 ml of water. The salt was acidified with 25 ml of 10% HCl and the product extracted with six 20 ml portions of ether. The ether extracts were combined and the ether removed under reduced pressure to give 3.0 g (54%) of the crude product, a tan solid, mp 135°–140° C. Purification was accomplished with a silica gel column using chloroform as the mobile phase. Two recrystallations from acetone gave 1.77 g (32%) of CSE, cream colored crystals, mp 161°–163° C.

The NMR and IR spectra were consistent with the structure of CSE. In the $^1$H NMR ($CDCl_3$) spectrum, in addition to the usual peaks of the cholesterol molecule, there are three distinctive peaks which indicate the presence of butyric acid ether structure: δ2.47 (t, 2H, 2-H), 1.96 (m, 2H, 3-H), 3.53 (t, 2H, 4-H). In the IR (KBr) spectrum, an absorption at 1708 $cm^{-1}$ shows the presence of a COOH group, which was also confirmed by base titration. The purity (>95%) of CSE was demonstrated by obtaining a single spot (Rf value of 0.34) with silica gel thin layer chromatography (TLC) using a mobile phase of chloroform and methanol (18:1). An elemental analysis of the product was consistent with CSE; calculated for $C_{31}H_{52}O_3$: C, 78.76%, H, 11.09%; found: C, 78.51%; H,11.02%. A titration using a standardized NaOH solution and CSE showed the molecular weight to be 481, which is within the experimental error of the theoretical value of 473. Treatment of CSE standard solutions with cholesterol esterase did not release free cholesterol (unlike CS standards) as measured with a Cobas-Bio Clinical Analyzer, (Cholesterol Reagent Kit #4434, Roche Diagnostic Systems, Nutley, N.J.) confirming the presents of non-hydrolyzable ether linkages.

To prepare the tris salt of CSE, 0.29 g (2.43 mM) of TRIS and 50 ml of methanol were added to a solution of 1.15 g (2.43 mM) of CSE in 5 ml of chloroform. The solution was warmed and the solvents removed under reduced pressure to give a cream-colored solid. Gentle warming removed the last traces of solvent to give 1.3 g (95%) of CSE, tris salt as a cream-colored solid, mp 118°–120° C.

TSE and its tris salt were prepared according to the following procedures. In a round bottom flask, 3.3 g (7.66 mM) of d-α-tocopherol, 1.6 g (10.8 mM) of 4-bromobutyronitrile, 20 ml of acetone, and 3.6 g (90 mM) of NaOH pellets were added together. The flask was capped, cooled, and then stirred at room temperature for 5 days. The inorganic salts were filtered off and the filtrate was warmed and the acetone removed under reduced pressure. The resulting crude nitrile residue was placed in a flask with 20 ml of isopropanol and 20 ml of 12% NaOH solution, warmed and stirred at 90° C. for 4 days. The solvents were removed under reduced pressure to give the crude sodium salt. With cooling, about 15 ml of concentrated HCl was added to five the free acid and this was extracted repeatedly with ether (7*15ml). The extracts were combined, washed with water, then the ether was removed under reduced pressure to give the crude desired acid, 3.9 g (98%), mp 45°–51° C. This product was dissolved in 20 ml of chloroform and passed through a short silica gel column; the chloroform removed under reduced pressure, and the product (TSE) was recrystallized using 15 ml of hot methanol to give cream-colored crystals, 2.6 g (66%), mp 55°–57° C.

The NMR and IR spectra were consistent with the structure of TSE. In the $^1$H NMR (CDCl$_3$) spectrum, in addition to the usual peaks of the tocopherol molecule there are three distinctive peaks which indicate the presence of butyric acid ether structure: δ2.66 (t, 2H, 2-H), 1.78 (m, 2H, 3-H), 3.70 (t, 2H, 4-H). In the IR (film) spectrum, an absorption at 1715 cm$^{-1}$ shows the presence of a COOH group, which was also confirmed by base titration. The purity (>95%) of TSE was demonstrated by obtaining a single spot (Rf value of 0.43) with silica gel TLC using a mobile phase of chloroform and methanol (18:1). An elemental analysis of the product was consistent with TSE; calculated for C$_{33}$H$_{56}$O$_4$: C, 76.69%; H, 10.92%; found: C, 76.70%; H, 10.88%. A titration using a standardized NaOH solution and TSE showed the molecular weight to be 523, which is within the experimental error of the theoretical value of 517. Treatment of TSE standard solutions with 4M KOH did not release free tocopherol (unlike TS standards), as measured by HPLC, confirming the presence of a non-hydrolyzable ether linkage.

The tris salt of TSE was prepared as described above with CSE. The product was an off-white powder, mp 80°–82° C., 100% yield.

The clonogenic assay used for the experiments was conducted as follows. Subcutaneous L1210 tumors, C1498 infected spleens and the tibula and fibula were aseptically dissected from mice, following cervical separation, and single cell suspensions were prepared in alpha MOPS, available from Gibco Laboratories of Grand Island, N.Y., at 37° C. Cell suspensions were centrifuged at 800×g and the total number of viable cells were determined using trypan blue exclusion. Cells were prepared in 60×15 mm plastic tissue culture dishes by adding 3 ml of cell suspension resulting in a concentration of 1×10$^3$ cells/dish for L1210 cells, 1×10$^5$ for C1498 cells, or 1×10$^5$ for CFU-GM cells. Dishes for each cell type and experimental treatment were produced in triplicate. The plating mixtures for L1210 cells consisted of RPMI 1640 medium supplemented with 15% calf serum, 1% beta mercaptoethanol, and 10% of a 3.5% agar solution maintained at 50° C. For C1498 cells, similar plating conditions were used except 10% of a 3% agarose solution was used in place of agar. For CFU-GM cells, the plating mixture consisted of alpha MEM medium supplemented with 15% calf serum, 10% L-cell conditioned media, 1% beta-mercaptoethanol, and 10% of a 3.5% agar mixture maintained at 50° C. To each of these plating mixtures, a 10% of ethanol (ETOH) solution was added which contained one of the following: TS, tris salt; TSE, tris salt; CS, tris salt; CSE, tris salt; T and tris succinate or C and tris succinate. FIGS. 23a–f present the chemical structures of T, C, TS, CS, TSE, and CSE. These compounds were added at a final concentration of 50, 100, 150, and 200 µM for L1210 and CFU-GM cells and 10, 25, 50 and 100 µM for C1498 cells. After the agar solution hardened, plates were incubated for 7 days at 37° C. in an atmosphere of 5% CO$_2$ in air. The number of cell colonies formed during this incubation period were determined using a stereo-zoom microscope at 20X magnification.

In the doxorubicin induced cell death experiments, suspensions of L1210, C1498, and CFU-GM cells were prepared at 5×10$^5$ cells/ml in the same media described for the clonogenic assays, minus agar. Cell suspensions (7 ml) were added to 25 cm$^2$ tissue culture flasks, in triplicate, and the tris salts of TS or CS or 10% ETOH (vehicle, 120 µl) at a final concentration of 150 µM (L1210 and CFU-GM cells) and 50 µM (C1498 cells). The flasks were incubated for 90 minutes at 37° C. in an atmosphere of 5% CO$_2$ in air, then DOX dissolved in 10% ETOH, was added to each flask at a final concentration of 0.0.01, 0.1, or 1 µM. Following 24 hours of incubation, the cells from each flask were centrifuged, resuspended and viability counts were performed using trypan blue exclusion.

As detailed above the treatment of TSE and CSE with strong base (4M KOH) or cholesterol esterase were ineffective in liberating measurable amounts (>2%) of T or C respectively (as expected for an ether linkage). By contrast, these same treatments readily released T (100%) and C (42%) from TS and CS respectively (as expected for an ester linkage). Thus, it is reasonable to conclude that a biological effect following TSE or CSE treatment results from the action of the intact compound.

The clonogenic survival assay described above was used to test the effect of the compounds on the proliferation of murine leukemia cell lines, C1498 and L1210, and murine normal bone marrow cells, CFU-GM. The tris salt of each compound, except T and C, was used to provide a more water soluble formulation. The results of these studies demonstrated that leukemia and normal bone marrow cell colony formation were unaffected (not significantly different from vehicle treated cells) by exposure to T in combination with tris succinate or by exposure to C and tris succinate.

Figure 24A:
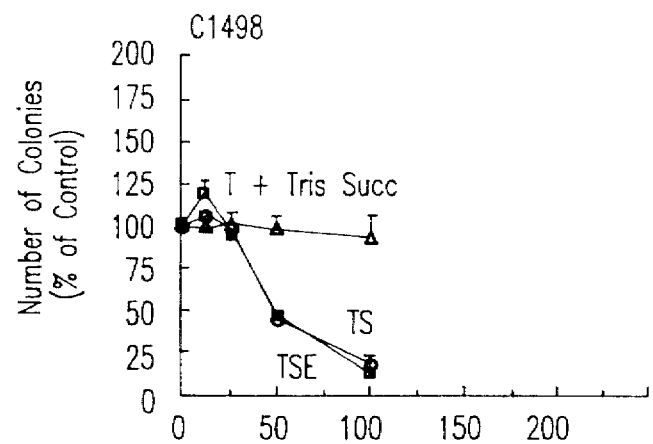
FIGS. 24a–c are graphs showing the effect of TS, TSE, and T and tris succinate on cell colony formation.
Figure 24B:
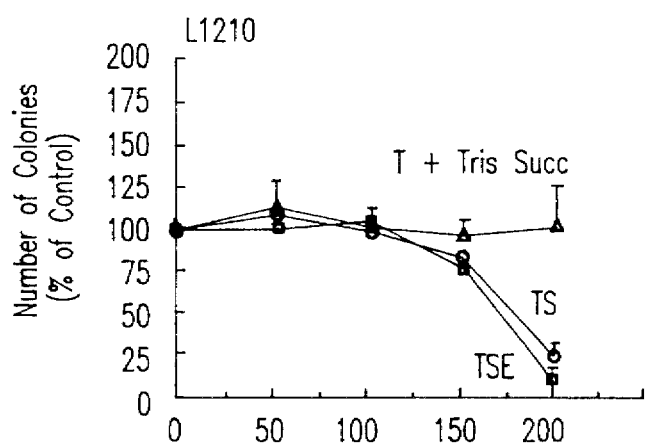
Figure 24C:
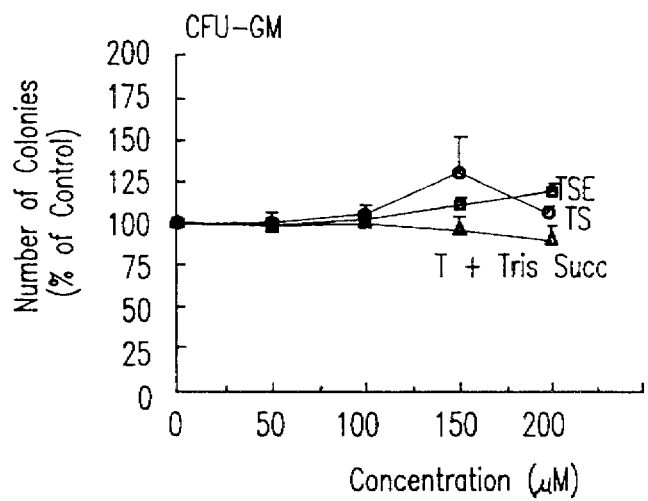

Specifically, FIGS. 24a–c shows the effect of TS, TSE and T and tris succinate on colony formation using C1498 leukemia, L1210 leukemia or CFU-GM normal bone marrow cells. Leukemia or normal bone marrow cells were suspended in medium containing TS, TSE or T and tris succinate and agar and were plated. Seven days later, the number of cell colonies formed in each plate were counted. The average number of cell colonies formed in each control plate was 157±15 for C1498 cells, 69±5 for L1210 cells and 182±14 for CFU-GM cells. Data are expressed as a % of the results obtained for control (vehicle) cells. Each data point represents the average of results obtained from 3 (±S.D.) separate cell preparation (*, p<0.05 vs T and tris succinate).

Figure 25A:
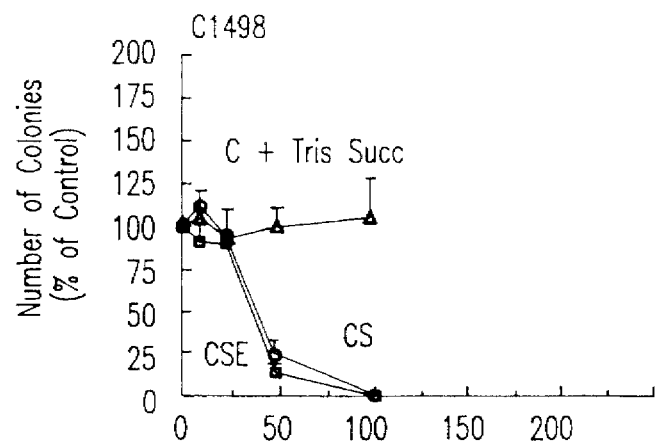
FIGS. 25a–c are graphs showing the effect of CS, CSE, and C and tris succinate on cell colony formation.
Figure 25B:
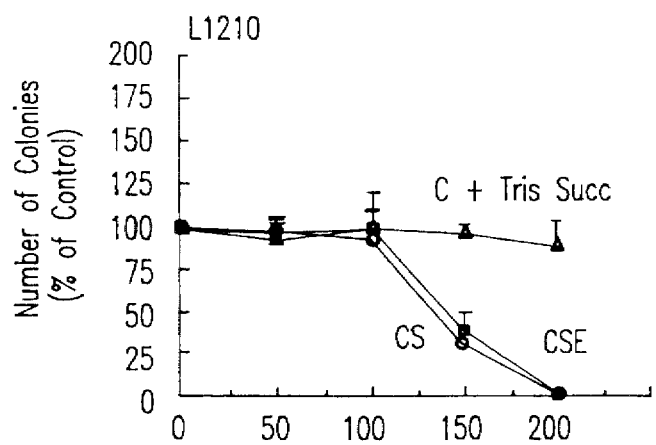
Figure 25C:
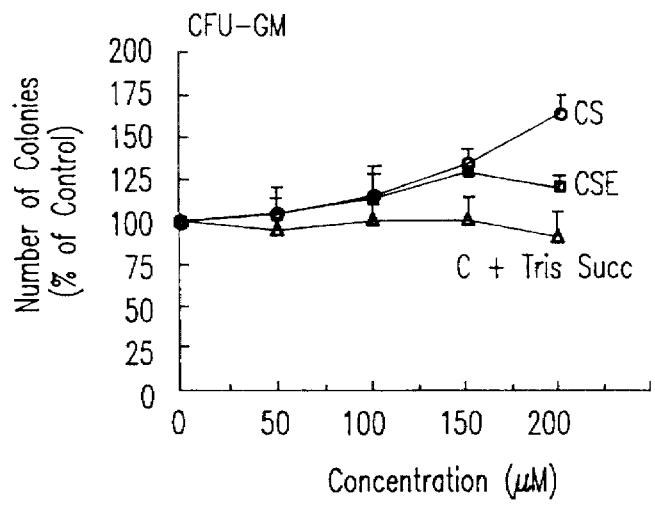

FIGS. 25a–c shows the effect of CS, CSE and C and tris succinate on colony formation using C1498 leukemia, L1210 leukemia or CFU-GM normal bone marrow cells. Leukemia or normal bone marrow cells were suspended in medium containing CS, CSE or C and tris succinate and agar and were plated. Seven days later, the number of cell colonies formed in each plate were counted. The average number of cell colonies formed in each control (vehicle) plate was 138±8 for C1498 cells, 57±4 for L1210 cells and 169±15 for CFU-GM cells. Data are expressed as a % of the results obtained for control (vehicle) cells. Each data point represents the average of results obtained from 3 (±S.D.) separate cell preparation (*, p<0.05 vs C and tris succinate).

In contrast to the T or C and tris succinate combination results, FIGS. 24a–c demonstrate a dose-dependent inhibition of leukemia cell colony proliferation with TS treatment. The myeloid derived C1498 cells were considerably more sensitive to the anti-proliferative effects of TS (IC$_{50}$ of 46±2 µM), as compared to lymphocytic derived L1210 cells (IC$_{50}$ of 175±15 µM). However, the ability of TS to inhibit cell growth was selective for tumor cells since inhibition of CFU-GM cell proliferation was not observed. In fact, at concentrations above 100 µM, TS appeared to stimulate NBM cell colony formation. These findings are in agreement with previous studies showing selective growth inhibition by TS, but not T, using a variety of tumor cell lines includeing human promyelocytic leukemia (HL-60) cells.

When murine leukemia and CFU-GM cells were treated with TSE, the effect of this ether on cell proliferation was identical to that observed for TS, regardless of the cell line, suggesting a similar mechanism of action for these two compounds. These data suggest that the observed inhibition of leukemia cell proliferation as well as the stimulation of NBM cell growth does not result from the action of T, but rather from the intact TS and TSE compounds.

FIGS. 25a–c show similar results for the effect of C and tris succinate, CS, and CSE treatment of leukemia and NBM cell proliferation to those observed in conjuction with FIGS. 24a–c. The only apparent difference between the actions of the tocopherol and cholesterol analogs was that the cholesterol analogs (CS and CSE) appear to have a slightly more potent antitumour effect than ther tocopherol counterparts. As observed with TS and TSE treatments, C1498 cells were considerably more sensitive to the cytotoxic effects of CS and CSE ($IC_{50}$ of 41±2 μM and 38±1 μM, respectively), as compared to L1210 cells ($IC_{50}$ of 136±6 μM and 142±10 μM, respectively). CS and CSE treatments were not cytotoxic to CFU-GM cells, but, instead, significantly stimulated cell proliveration at concrations above 100 μM (as was observed for TS and TSE).

Figure 26A:
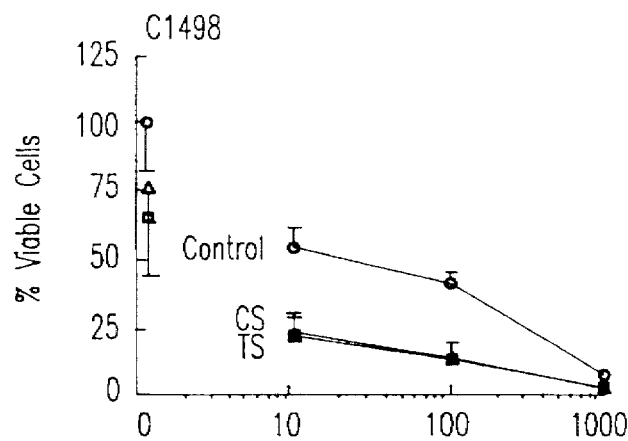
FIGS. 26a–c are graphs showing the effect of CS, TS and vehicle on DOX-induced cell death.
Figure 26B:
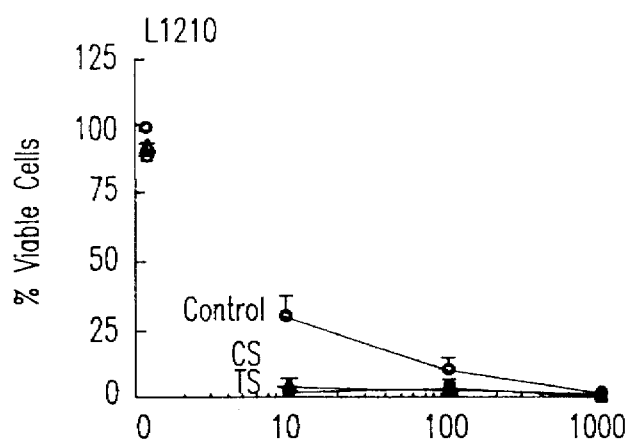
Figure 26C:
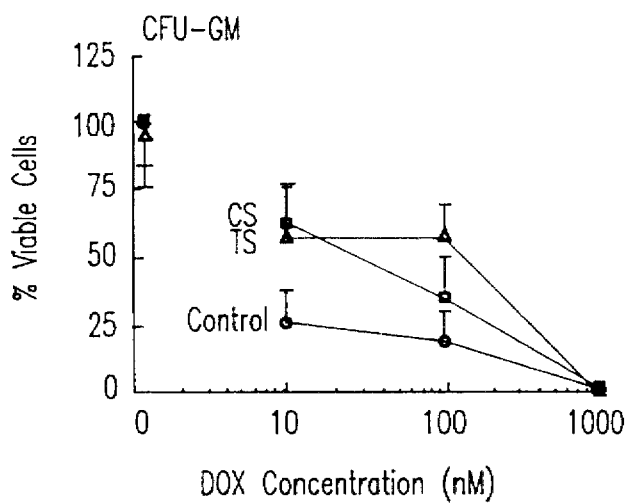

While TS and CS have a modest effect on tumor cell viability by themselves (after a 24 hr incubation), when they are used in combination with DOX (at 0.01 and 0.1 μM) they significantly enhanced DOX-induced cell death, as can be seen from FIGS. 26a–c. Specifically, FIGS. 26a–c show the effect of CS, TS and vehicle (control) pretreatment on DOX-induced cell death in C1498 leukemia, L1210 leukemia or CFU-GM normal bone marrow cells. Cell suspensions were incubated with TS, CS or vehicle, 150 μM (L1210 and CFU-GM cells) and 50 μM (C1498 cells) for 90 minutes, followed by exposure to 0, 0.01, 0.1, or 1 μM DOX for 24 hrs. Cell viability was then determined by trypan blue exclusion. Each data point represents the mean of results obtained from 3 (±S.D.) separate cell preparations. FIGS. 26a–c also show that the pretreatment of NBM cells with TS or CS did not potentiate the toxic effect of DOX, but, instead, protected CFU-GM cells from the lethal effects of DOX (at 0.01 and 0.1 μM). The data demonstrate that NBM and leukemia cells react quite differently in the presence of TS or CS. These findings agree with earlier studies which have demonstrated that TS treatment potentiates the cytotoxic effects of DOX and other agents in numerous tumor cell lines and also with the earlier studies that show TS protects hepatocytes in vitro and in vivo against a wide variety of toxic agents including DOX.

The striking similarities between the dose-dependent actions of CS, CSE, TS and TSE on three different cell lines, in the present and absence of DOX strongly suggest that these four compounds share a common mechanism of action, one most likely resulting from the intact compound. The results demonstrate that the expression of TS, TSE, CS and CSE activity in leukemia cells are markedly different from that observed in NBM cells. In the murine myeloid and lymphocytic derived leukemia cell lines, these compounds inhibited tumor cell proliferation and enhanced tumor cell kill by DOX. By contrast, these same anti-tumor compounds stimulated murine CFU-GM normal bone marrow cell growth and protected these cells from the lethal effects of DOX. Due to the remarkable similarities in actions of TS, CS, TSE, and CSE, in each of these cell lines, it is proposed that they share a common mechanism of action that is dependent on the intact compound. The data support the use of TS, CS, and the ether derivatives TSE and CSE, as therapeutic antitumor/cytoprotective agents alone or in conjunction with other cancer therapies such as DOX or radiation. Such combination therapy may improve the anti-tumor efficacy of currently approved cancer therapeutics while limiting their dose-limiting side effects in normal tissue (i.e., myelotoxicity). It is suggest that this combination therapy may prove extremely valuable in autologous bone marrow transplantation therapy for the treatment of cancer, where high levels of the intact TS, TSE, CS, or CSE can be maintained in vitro to selectively eradicate tumor cells while sparing or even promoting the proliferation of the patient's NBM cells prior to re-administration.

Based on the above data it is emphasized that any therapeutic or experimental use of TS, CS or a related analog, must insure that the intact compound (active) reaches the site of action (tumor cells). Thus, the oral administration of these liphophilic succinate esters is not likely to result in tissue accumulation of the intact compound, nor provide anti-tumor activity or cytoprotection. It is recommended that these esters be administered by a route that will not result in hydrolysis. The non-hydrolyzable compounds TSE and CSE might be active when orally administered, since they will remain intact. In addition, TSE and CSE have the potential of providing longer lasting anti-tumor activity.

Figure 27:
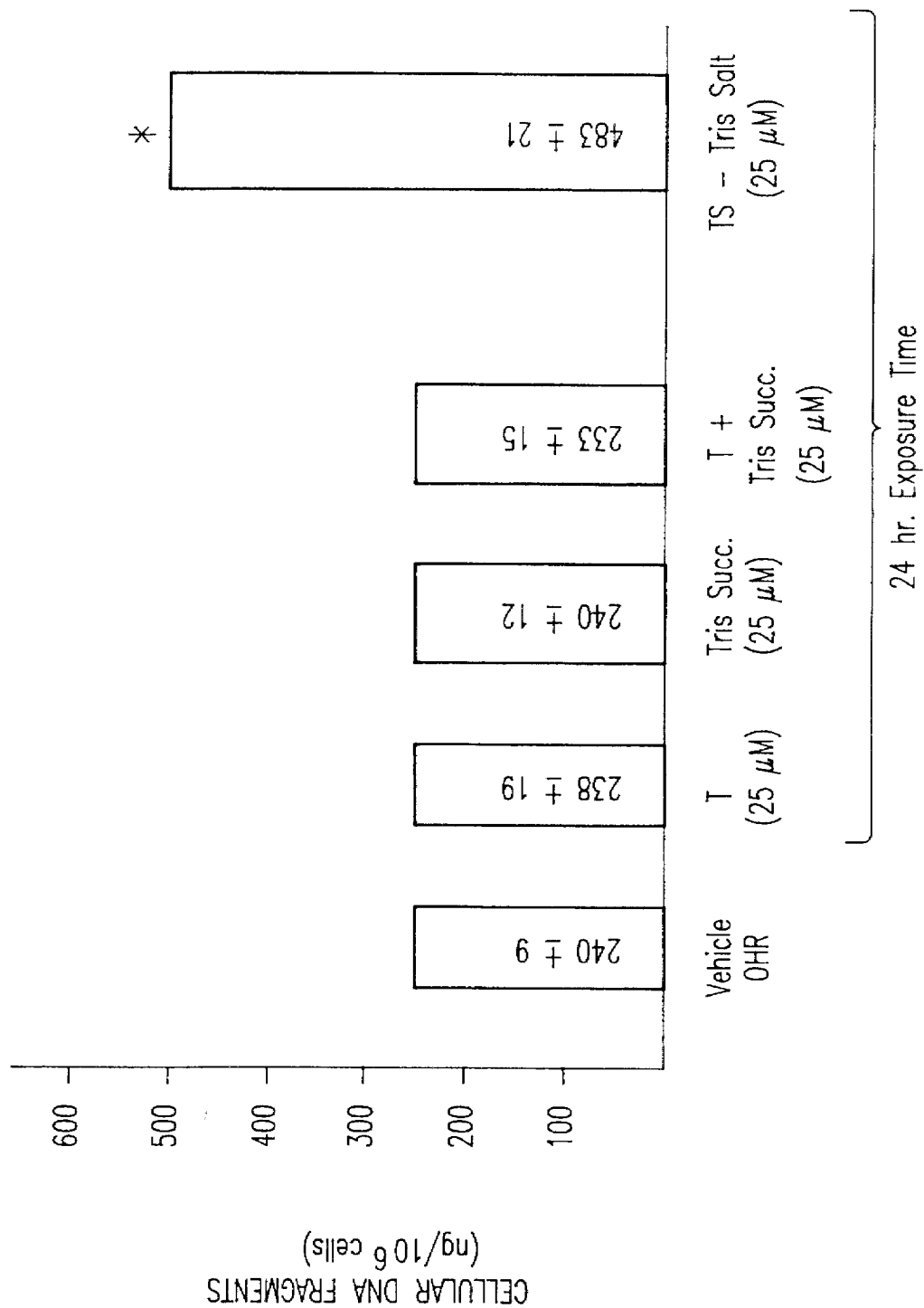
FIG. 27 is a bar graph showing DNA fragmentation in a human leukemia cell line (HL-60)

FIG. 27 shows TS-tris salt induced DNA fragmentation in human promyelocytic leukemia cell line HL-60. The values reflect the mean±SEM, n=4, (* $p<0.5$) compared to other treatments.

In this study, HL-60 cells were incubated with 25 μM of one of the following: d-alpha-tocopherol; tris succinate; d-alpha-tocopherol and tris succinate; or tocopherol succinate (TS), tris salt. After 24 hours of incubation, the cells were analyzed for DNA fragments using bisbenzimide spectrofluorophotometry, as was previously described by Jarvis et al. *Biochem. Pharmacol.* 47:839–852, 1994. It has been found that the degree of low moleculr weight DNA fragmentation detected by this method closely correlates with the incidence of apoptosis-induced cell death in HL-60 cells (Grant et al. *Cancer Res*, 52:6270–6278, 1992). Therefore, the results shown in this figure suggests that TS, tris salt (but not unesterified tocopherol or tris succinate) treatment kills human leukemia cells by inducing apoptosis.

Figures 14A, 14B:
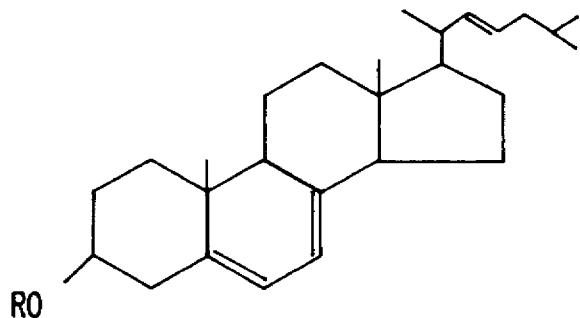
Figures 15A, 15B:
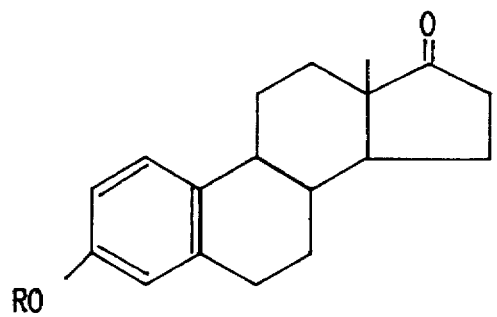
Figures 16A, 16B:
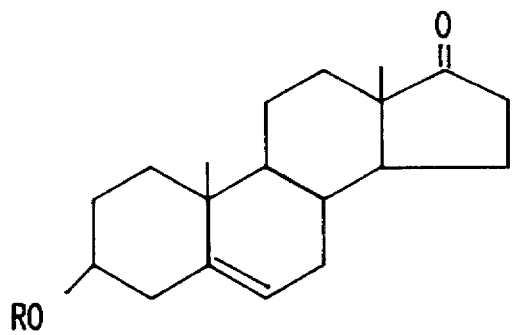

In vivo experiments have been conducted which demonstrate that cholesteryl succinate protects against liver ischemia/reperfusion-induced lethality or injury. Table 21 shows the results of a total ischemia study where male Sprague-Dawley rats were subjected to global occlusion of the hepatic artery and portal vein for 60 minutes followed by reperfusion for 24 hours. 20 hours prior to global occlusion, one group of 10 rats was provided with 64 mg cholesterol/kg body weight and 100 mg tris succinate/kg body weight by i.p. injection, and another group of 10 rats was provided with 100 mg cholesteryl succinate/kg body weight. A control group of rats was only partially occluded for the one hour period. Ninety percent of the rats pretreated with cholesteryl succinate tris salt survived while only 10% of those pretreated with the combination of cholesterol and tris succinate survived. Table 22 of a partial ischemia study where male Sprague-Dawley rats were subjected to occlusion of the blood supply to the left lateral and median lobes of the liver for 60 minutes followed by reperfusion for 24 hours. During this time, the normal blood supply to the other lobes of the liver was maintained. This treatment does not result in lethality (liver failure), but does produce significant liver damage. Serum was obtained for AST and ALT measurements. One group of rats was provided with an i.p. dose of saline (same volume as used for other treatments) and the other group of rats was provided with an i.p. dose of 100 mg cholesteryl succinate tris salt/kg body weight 20 hours prior to inducing partial ischemia. FIG. 14 demonstrates that cholesteryl succinate tris salt administration prior to or during the ischemic challenge significantly reduces ischemia-induced liver damage. Protection was observed for both fed and fasted rats. In addition, experiments have also been conducted which demonstrate that rats which were administered cholesterol plus tris succinate were not protected from the hepatotoxic effects of partial ischemia. Additional experiments were conducted which show that significant ($p<0.05$) protection against partial ischemia-induced liver damage occurs when rats are pretreated with a 25 mg cholesteryl succinate tris salt/kg body weight i.p. dose (ALT 358±38) as compared to vehicle alone (saline)(ALT 1027±235) and with dihydrocholesterol sulfate, sodium salt (ALT 1305±568) when compared to dihydrocholesterol plus sodium sulfate (ALT 3262±1850).

The data from these in vivo experiments demonstrate that ionizable congeners of aromatic and aliphatic alcohols, and particularly cholesteryl succinate and dihydrocholesterol sulfate, can be used to protect against ischemia induced injury. In addition, these compounds have been shown to be therapeutic whether used prophylactically or administered at the time of injury. Thus, these compounds can be used to protect against injuries caused by heart attacks, stroke, and injuries consequent with the blood supply to an area being compromised. It is expected that the ionizable congeners of aromatic and aliphatic alcohols will also have significant value in transplantation surgery.

Figure 10:
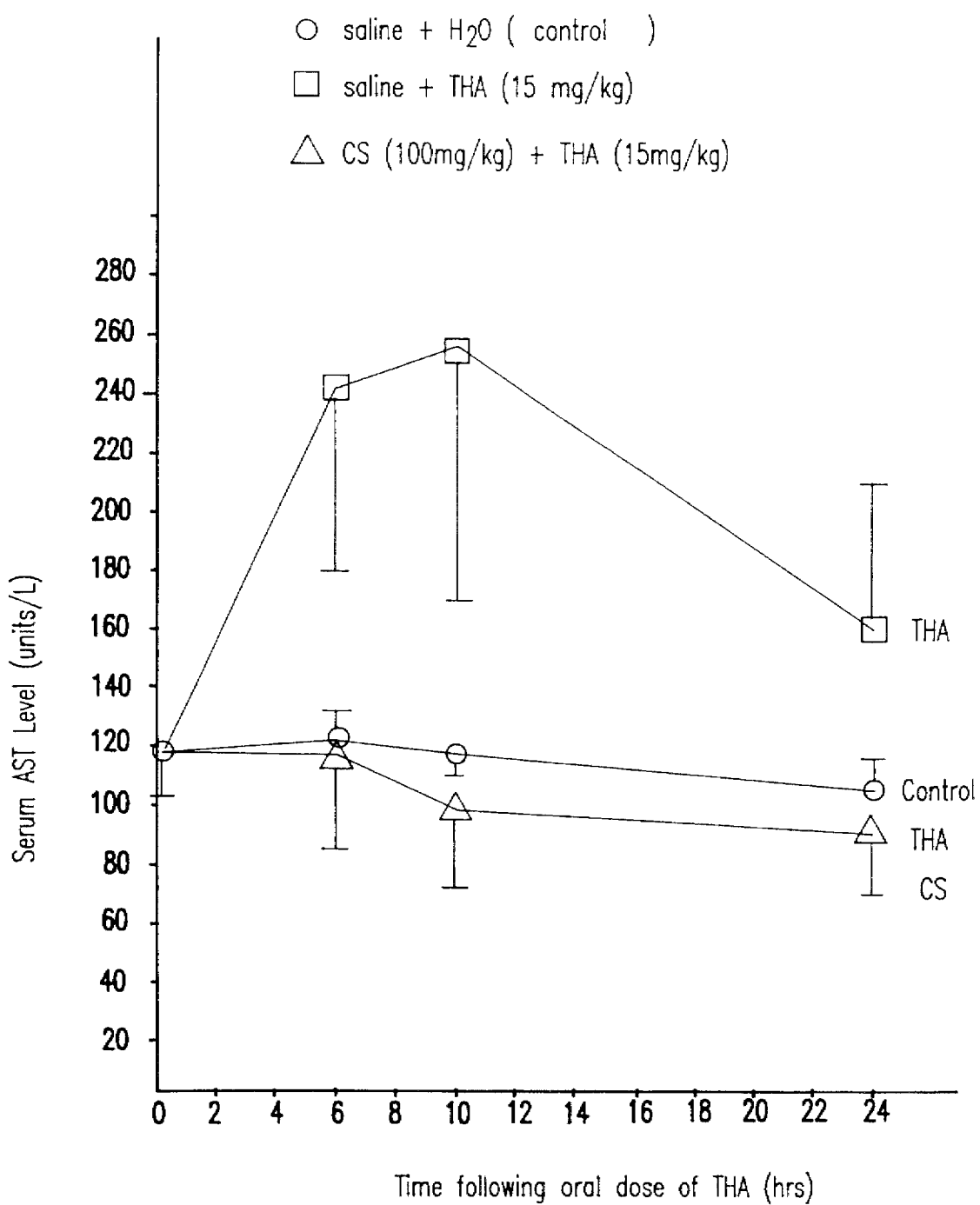
FIGS. 10 and 11 are graphs showing the in vivo protective effects of cholesteryl succinate against tetrahydroaminoacridine (THA)-induced hepatotoxicity.
Figure 11:
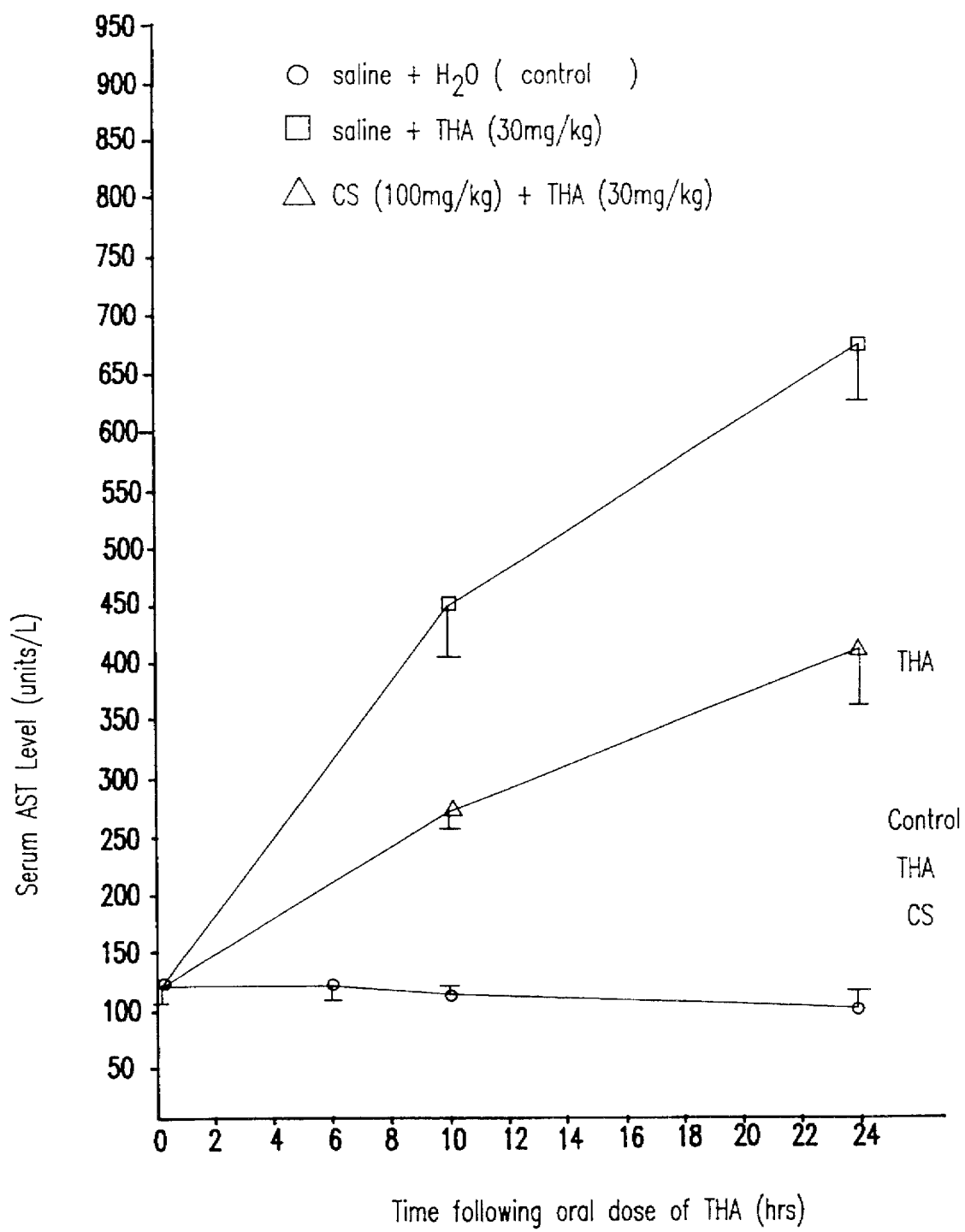

In vivo experiments have been conducted which demonstrate that cholesteryl succinate protects against the hepatotoxic effects of therapeutic drugs such as acetominophen (AP) and tetrahydroaminoacridine (THA). Table 23 shows the effects on AST and ALT serum levels for male Sprague-Dawley rats which are given a 2 g/kg body weight oral dose of acetaminophen. Providing the rats with a 100 mg/kg body weight i.p. dose of cholesteryl succinate tris salt 20 hrs prior to administration of the acetominophen challenge resulted in significant protection against the hepatotoxic effects of this drug as compared to control rats given an equal dose of tris succinate. FIGS. 10 and 11 show the results of in vivo experiments where male Sprague-Dawley rats were given an oral dose of 15 or 30 mg THA/kg body weight, respectively. In the experiments, one group of rats was provided with an i.p. dose of 100 mg cholesteryl succinate tris salt/kg body weight 20 hours prior to the THA challenge, another group of rats only received the THA challenge, and the last group of rats acted as a control and were not challenged. The serum AST levels were determined with respect to time after the THA challenge. In both FIGS. 10 and 11, it is demonstrated that prior treatment with cholesteryl succinate protects against the hepatotoxicity resulting from THA. Table 24 also shows that prior treatment with cholesteryl succinate resulted in an increase in the secretions generally associated with the effects of THA on acetylcholine release in the central nervous system. These secretory effects normally accompany the beneficial influences of THA on Alzheimer's disease; hence, cholesteryl succinate may facilitate the anti-Alzheimer's effects of THA as well as protect against THA-mediated hepatotoxicity.

The toxicity elicited by numerous therapeutic agents results from the metabolism of these compounds in the liver. In vivo experiments have been conducted with alpha-TS and cholesteryl succinate to determine their effect on metabolism via the pentobarbitone-induced sleeping time test. The duration of pentobarbitone-induced sleeping time is directly dependent on the metabolism of pentobarbitone in the liver. Table 25 shows that alpha-TS and cholesteryl succinate administered before the pentobarbitone-induced sleep may slightly increase sleeping time, but not significantly. In contrast, a drug known to interfere with drug metabolism in the liver (metyrapone 100 mg/kg body weight, i.p.) significantly increased (8 fold, $p<0.001$) the pentobarbitone induced sleeping time. These results indicate that alpha-TS and cholesteryl succinate induced protection do not result from their effect on drug metabolism.

Structure, dose, time of pretreatment, and route of administration of cholesteryl succinate can all have an effect on $CCl_4$-induced hepatotoxicity. Table 26 shows that both the tris salt and the free acid of cholesteryl succinate are cytoprotective agents; however, only cholesteryl succinate tris salt is significantly cytoprotective in vivo when compared to the vehicle control. The tris salt forms a fine micellular suspension that appears to have high bioavailability when injected intraperitoneally. In contrast, the free acid is insoluble in an aqueous medium and is, therefore, less available for uptake. This same effect was also demonstrated for alpha-TS. As shown in Table 27, the tris salt of alpha-TS is more protective than the free acid.

Table 28 shows cholesteryl succinate tris salt is protective over a wide range of dosages. There are significant ($p<0.001$) cytoprotective effects produced when 50, 100 and 200 mg cholesteryl succinate/kg body weight when administered by i.p. injection 20 hrs prior to an oral 1 g $CCl_4$/kg body weight challenge. Optimal doses are 100 mg/kg or greater. Table 29 shows cholesteryl succinate tris salt is protective when given 20 hrs prior to $CCl_4$ administration, but not effective when given at intervals 30 minutes or shorter prior to $CCl_4$ administration or after $CCl_4$ administration. The long pretreatment times to achieve cytoprotection may indicate that cholesteryl succinate operates by inducing endogenous cellular processes. As shown in Table 20, cytoprotection was coincident with i.p. injections of cholesteryl succinate, but was not induced when administered by oral gavage.

Table 30 shows the effect of in vivo administration of a wide variety of ionizable congeners of aromatic and aliphatic alcohols on $CCl_4$-induced hepatotoxicity. Similar to the experiments were described above, the ionizable congeners were administered to Sprague-Dawley rats by i.p. injection of a 100 mg ionizable congener/kg body weight dose 20 hours prior to oral administration of a 1 g/kg dose of $CCl_4$, and the AST and ALT levels were measured 48 hours after the $CCl_4$ challenge. Hepatoprotection was based on a comparison with the AST and ALT levels found in rats treated only with the vehicle control. Table 30 shows that alpha-TS tris salt, cholesteryl succinate tris salt, cholesteryl 3-sulfate sodium salt, cholesteryl hydrogen phthalate, dihydrocholesterol sulfate sodium salt, dihydrocholesterol succinate free acid and tris salt, and linoleyl succinate were all effective in protecting against hepatotoxicity. Table 30 also shows that some ionizable congeners were not effective.

Table 31 shows that the administration of cholesterol succinate tris salt 20 hours prior to the administration of 1 g/kg (oral gayage) of $CCl_4$, results in complete protection for Sprague-Dawley rats as measured by serum enzyme levels. In contrast, the administration of cholesterol and cholesterol acetate provided no protection. Table 32 shows that pretreatment with cholesterol plus succinic acid also provides no protection from a $CCl_4$ challenge. In addition, Table 32 shows that cholesteryl succinate tris salt and alpha-TS, when administered by i.p. dosage using PEG 400 as the vehicle, provide effective hepatotoxic properties, and that cholesteryl succinate tris salt is more effective than alpha-TS. Tables 33 and 34 show that cholesteryl 3-sulfate sodium salt and cholesteryl hydrogen phthalate proved to be potent cytoprotective agents in vivo. Tables 35–37 show that the administration of dihydrocholesteryl succinate free acid or tris salt or dihydrocholesteryl sulfate sodium salt (100 mg/kg i.p.) 20 hours prior to the oral administration of a 1 g $CCl_4$/kg body weight to male Sprague-Dawley rats resulted in complete protection against hepatotoxicity as measured by serum enzyme levels. In contrast, the administration of the sterol (dihydrocholesterol) plus sodium sulfate produced no significant cytoprotection. Hence, the results suggest that neither the succinate nor the cholesterol molecule is essential for cytoprotection; rather, it is the ionizable lipophilic molecule that is primarily responsible for cytoprotection.

Table 38 shows that the administration of either ergosterol succinate tris salt or ergosterol sulfate potassium salt (100 mg/kg i.p.) 20 hours prior to the administration of an oral (1 mg/kg) dose of $CCl_4$ to Male Sprague-Dawley rats resulted in protection against hepatotoxicity as measured by serum enzyme levels. Table 39 shows that the administration of ergosterol alone also results in cytoprotection from toxic $CCl_4$ insults. Table 39 also shows that dehydroepiandrosterone (DHEA) derivatives do not provide protection against hepatotoxicity, but that linoleyl succinate (free acid) does provide some cytoprotection. With reference back to Table 35, it can be seen that pretreatment of the Sprague-Dawley rats with linoleyl alcohol does not provide cytoprotection and, in fact, it potentiates $CCl_4$ toxicity. This is evidence of the anticytotoxic effect of ionizable congeners, wherein a toxic drug, such as linoleyl alcohol, is made non-toxic or cytoprotective by the addition of an ionizable congener. Table 41 shows that retinoic acid and retinol acetate also potentiated $CCl_4$ toxicity. Tables 33, 35, 37, and 40 show that the straight chain aliphatic alcohols and their derivatives, such as lauryl sulfate sodium salt, palmityl alcohol, palmityl succinate, phytol, and phytol succinate were generally not protective. Comparing Tables 34, 40, and 42 it can be seen that pretreatment of Sprague Dawley rats with estrone 3-succinate (free acid) or estrone sulfate potassium salt resulted in slight cytoprotection that was not greater than that observed for non-ionizable derivatives estrone and estrone acetate administration. Comparing the data for the estrone analogs with the DHEA data suggest that optimal cytoprotection may be induced with an ionizable congener of a sterol molecule. With reference back to Table 33, no cytoprotection was observed using hydrocortisone 21-succinate. Hence, it is suggested that the ionizable congener may need to be attached at position 3 of the sterol molecule for anticytotoxic activity. FIGS. 12a–b to 22a–b show the relationship between the chemical structure, the presence of an ionizable congener, and the cytoprotection provided by the compounds discussed above in conjunction with Tables 30–42.

The experimental results demonstrate that cytoprotection results from accumulating an intact ionizable congener of an aromatic or aliphatic alcohol in the cell. Cellular accumulation of alpha-TS, an ionizable congener of an aromatic alcohol, is continuous and gradual (1.65 nmol/$10^6$ cells/hr; 25 µM dose) with a slow cellular release of succinate (0.65 nmol/$10^6$ cells/hr., as measured by alpha-tocopherol release; 25 µM dose). Release of the succinate moiety occurs through the action of cellular esterases and the succinate molecule acts as a substrate for increased energy production. Ionizable congeners of aromatic and aliphatic alcohols include the succinic ester of tocopherol, the methyl ester of tocopheryl succinic acid, the PEG ester of tocopheryl succinic acid, the succinic acid ester of cholesterol, dihydrocholesteryl succinate or sulfate, estrone succinate or sulfate, ergosterol succinate or sulfate, linoleyl succinate or any other ionizable ester or ether derivative of aromatic and aliphatic alcohols and their pharmaceutically acceptable salts and tris salts. By altering the ionizable side chain of the aromatic or aliphatic alcohol, anticytotoxic compounds will be created. The distance between the ionizable group and the aromatic carbon ring or the aliphatic ring or chain may be varied by increasing or decreasing the carbon chain length. For example, instead of tocopheryl succinate (4 carbons) or cholesteryl succinate (4 carbons), esters of other dicarboxylic acids can be made; such as oxalic acid (2 carbons), malonic acid (3 carbons), adipic acid (6 carbons), and phtalic acid, et cetera. The number of carbon double bond carbons in the side chain between the ionizable group and the aromatic or aliphatic alcohol group can be varied. For example, aromatic and aliphatic esters of fumaric acid and maleic acid can be synthesized. The ionic strength of the ionizable side chain on the aromatic or aliphatic alcohol can be varied. For example, the number of ionizable groups on the side chain (citrate, hydroxy succinate; etc.) can be increased or the number of ionizable groups (diester of alpha-TP) can be reduced. The chemical nature of the ionizable side chain can be varied by synthesizing tocopherol esters, tocopheryl phosphate esters, tocopheryl glutarate esters, tocopheryl succinate esters, or other aromatic or aliphatic esters of cellular constituents such as amino acids (lysine, arginine, cysteine, aspartate, glutamate), proteins (glutathione) lipids (phosphatidylcholine, omega-3 fatty acids), nucleic acids (adenosine, AMP), carbohydrates (glucuronic acid, glucose, fructose), and taurine (thiol ester). The chemical nature of the ionizable side chain can be varied by synthesizing tocopherol esters, tocopheryl phosphate esters, tocopheryl glutarate esters, tocopheryl succinate esters, or other aromatic or aliphatic esters of compounds known to be cytoprotective such as retinyl phosphate (vitamin A analog), dithiotheitol, ascorbic acid (vitamin C) and reduced ubiquinone, metal chelators (EDTA), omega-3 fatty acids, calcium antagonists, and antagonists of excitatory amino acids (adenosine derivatives of alpha-amino adipate). The chemical nature of the ionizable side chain can be Varied by synthesizing tocopherol congeners or other aromatic or aliphatic congeners with an ether linkage between the side chain and the aromatic carbon ring of tocopherol or a sterol or with bulky side chains or aromatic groups situated in close proximity to the ester linkage (e.g., 2,2 dimethyl succinate). Diesters of alpha-T can be formulated with succinate (e.g., alpha-T-Succinate-T-alpha). These chemical alterations will retard or prevent the hydrolysis of the bond between the aromatic ring of tocopherol and the ionizable side chain. The chemical nature of the ionizable side chain can be varied by synthesizing tocopherol esters, tocopheryl phosphate esters, tocopheryl glutarate esters, tocopheryl succinate esters, or other aromatic or aliphatic esters of compounds known to be involved in essential cellular processes such as substrates for cellular energy production (e.g., gluceraldehyde 3-phosphate, 3-phosphoglyceryl phosphate, phosphoenol pyruvate, phosphocreatine, malate, oxalacetate and alpha-ketoglutarate, and glutarate). By altering the lipophilic aromatic or aliphatic alcohol, anticytotoxic, procytotoxic and therapeutic compounds can be produced. Phenolic or aromatic compounds can be used for the attachment of an ionizable side chain. Such phenolic compounds might include tocopherol, trolox (chromamol ring of tocopherol), butylated hydroxytoluene (BHT), butylated hydroxylanisole (BHA), tannins (polyphenols, e.g., ellagic acid or corilagin), phytol, bactoprenol, co-enzyme Q, butoxyphenol, anthracycline antibiotics, and heterocyclic alcohols (pyridines, pyramidines, purines, etc.). Aliphatic compounds containing hydroxyl groups can be used for the attachment of an ionizable side chain. Such aliphatic compounds might include cholesterol, glycol polymers (propylene glycol or polyoxyethylene glycol), glycerin related compounds (glycerin, glycerol phosphate, monoacylglycerol, diacylglycerol, phosphatidylglycerol, cardiolipin, phosphatidylinositol, or sphingosine), steroids and their derivatives (estradiol, estriol, testosterone, methandriol (anabolic steroid), methylprednisolone, prednisolone), vitamins and their derivatives (retinal, riboflavin, pyridoxal), prostaglandins and their derivatives (PGE2, PGI2, iloprost, PGBx, or long chain fatty acids), or heterocyclic alcohols (pyroles, furans, imadozoles). The chemical nature of the ionizable side chain can be varied by synthesizing tocopherol esters, tocopheryl phosphate esters, tocopheryl glutarate esters, tocopheryl succinate esters, or other aromatic or aliphatic esters of compounds known to be cytotoxic (including the inhibition of cellular energy production, e.g., malonate, 3-phosphoglyceryl arsenate or halogenated derivatives of tricarboxylic acid cycle substrates, e.g., succinate)(See Gershon et al., *J. Med. Chem,* 20:606 (1979)). The chemical nature of the ionizable side chain can be varied by synthesizing tocopherol esters, tocopheryl phosphate esters, tocopheryl glutarate esters, tocopheryl succinate esters, or other aromatic and aliphatic esters of therapeutic drugs. This formulation should promote the cellular uptake and cellular retention of drugs thus providing a cellular reservoir for the release of drugs at critical cellular sites. For example, the cellular uptake of genetically engineered peptides and other products could be facilitated by their chemical attachment to aromatic and aliphatic alcohols. For another example, a recently discovered antibacterial agent that specifically inhibits lipopolysaccharide synthesis, is limited by its inability to penetrate the bacterial membrane (See, Goldman et al., *Nature,* 329, 162 (1987) and Goldman et al, *Science News,* 132:180 (1987)). Peptides have been chemically attached to this antibacterial agent to promote bacterial uptake; however, these carriers are short lived in vivo and do not provide penetration into all bacterium. Combining alpha-T with the antibacterial agent [alpha-C(1, 5-anhydro-7-amino-2,7 -dideoxy-D-manno-heptopyranosyl)-carboxylate] through an ester linkage will produce an ionizable congener that will promote tocopheryl congener bacterium uptake and retention of the therapeutic agent (antibacterial) with its cellular release from tocopherol resulting from the action of bacterial esterases.

The data also demonstrate that the more water soluble derivatives of ionizable congeners are more effective as anti-tumor agents and as cytoprotective agents for normal tissue against antitumor agents such as DOX and cancer causing agents such as EMS, $CCl_4$, radiation. For example, PEG esters are more effective than tris salts, and tris salts are more effective than free acids, and free acids are more effective than non-ionic forms (e.g., TS-PEG>TS-tris>TS>T). Particularly good anti-tumor activity and cytoprotective activity can be obtained with TS-PEG and CS-PEG.

Figure 28:
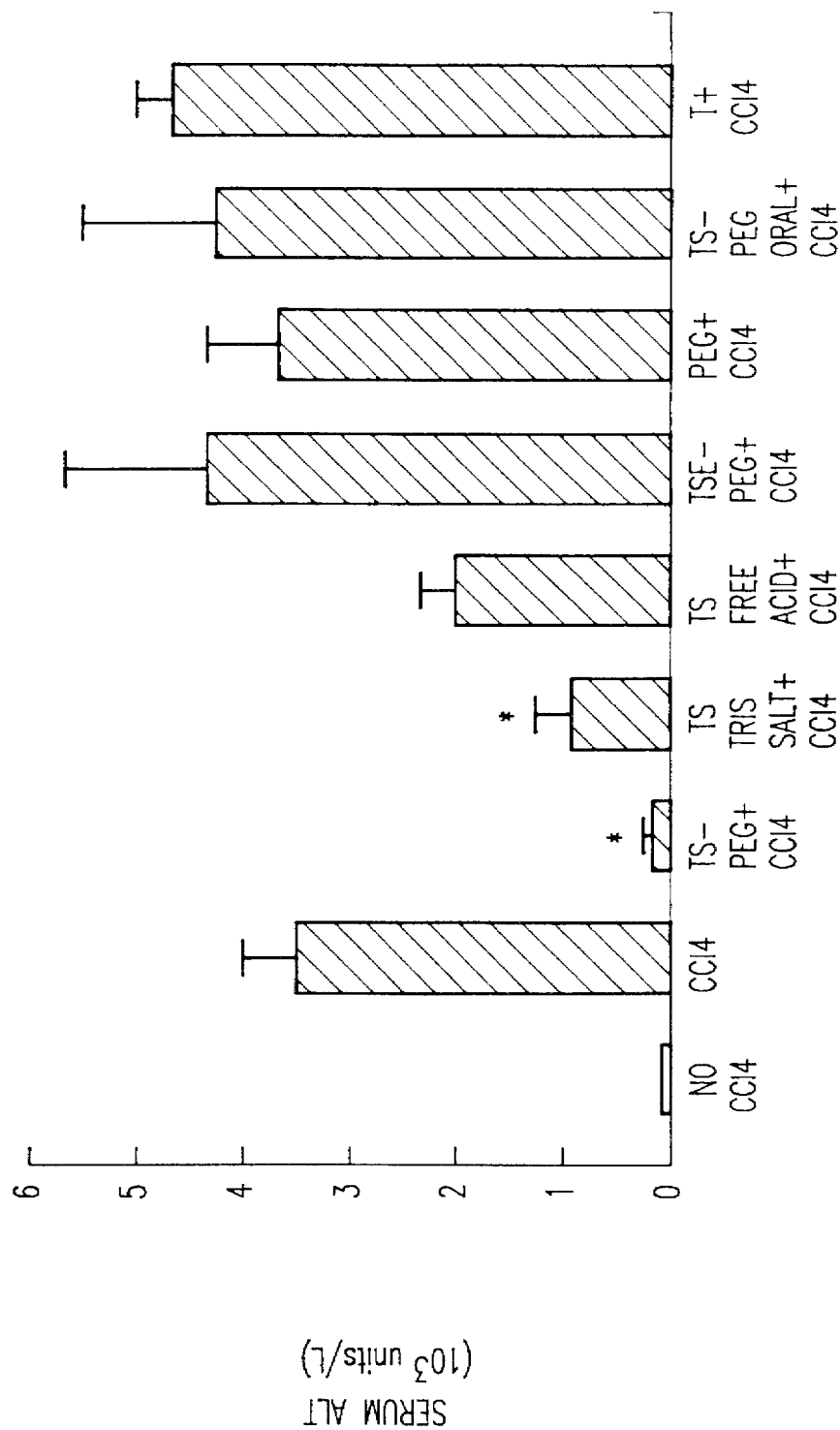
FIG. 28 is a bar graph showing the in vivo effects of TS-PEG, TS tris salt, TS free acid, tocopheryloxybutyric acid(TSE)-PEG, PEG, tocopherol against carbon tetrachloride-induced hepatotoxicity.

Data demonstrating the enhanced hepatoprotective efficacy of water-soluble derivatives of TS are shown in FIG. 28. In this experiment, male Sprague-Dawley rats were given an ip dose in the range of 100–300 mg/kg, depending on the molecular weight of the compound, of TS-PEG; TS, tris salt; TS, free acid; tocopheryloxybutyric acid (TSE)-PEG; PEG 1000; or unesterified alpha tocopherol (T) or an oral dose, 300 mg/kg, of TS-PEG. The rats were then fasted for 24 hours prior to the oral administration of a hepatoxic dose of 1 g/kg of $CCl_4$. The dose of $CCL_4$ was dissolved in peanut oil. One hour after receiving the $CCl_4$, the rats were given food. Forty eight hours later, the serum alanine aminotransferase (ALT) levels were determined using a spectrophotometric procedure with a Cobas Bio Clinical Analyzer. The results shown in the figure are the mean S.D. of 5 rats in each treatment group. As shown in the results the TS-PEG+$CCl_4$ and TS tris salt+$CCl_4$ has a $p<0.05$ as compared to the $CCl_4$ only group.

Water soluble forms of the congeners should enhance their cellular accumulation. As can be seen in Table 6, the potassium salt of the TS results in the enhanced accumulation of TS in the liver. In addition, salts of TS are more effective protective agents. It is believed that the enhanced hydrophilicity (ionic charge) of TS allows this compound greater access and incorporation into intracellular membranes, than the non-charged T, which will provide subcellular membranes with a reservoir of T (esterase hydrolysis provide continuous generation of T from the membrane bound antioxidant precursor, TS), and, hence, protection against aberrant membrane oxidation. Increasing the hydrophilicity of T derivatives increases the access and retention of T in intracellular membranes. By using more water soluble forms of the tocopherol congeners, rapid targeting of exogenous tochopherol to vital intracellular membrane sites to protect tissue from cancer, aging, ischemia, etc., can be achieved.

While the invention has been described in terms of the preferred embodiment of the invention, those skilled in the art will recognize that other cytoprotective agents and different concentrations can be employed within the spirit and scope of the appended claims.

TABLE 18

Protective Effect of Tocopherol and Succinate Analogs on Carbon Tetrachloride Induced Lethality and Hepatotoxicity in Rats

| Tocopherol or Succinate Analog Administered[a] | Survival after $CCl_4$ treatment[b] | Calculated $LD_{50}$ (g $CCl_4$/kg) | SGOT[c] Levels ($10^1$ units/L) |
|---|---|---|---|
| Vehicle (No $CCl_4$) | Yes | | 0.12 ± .03 |
| Vehicle (olive oil) | No | 2.6 | 3.57 ± 1.18 |
| Alpha-Tocopherol | No | 1.5 | |
| Succinic Acid | No | 2.6 | |
| Alpha-Tocopheryl Succinate | Yes | 4.4 | |
| Cholesteryl Succinate tris salt | Yes | 4.4 | 0.10 ± 0.03 |
| Cholesterol | No | 2.6 | 4.08 ± 2.45 |
| Alpha-Tocopheryl Glutarate | No | 2.6 | |
| Alpha-Tocopheryl 3-Methyl Succinate | No | 2.6 | |

[a]-100 mg/kg given i.p., 24 hours prior to $CCl_4$ insult, n > 3.
[b]-2.9 g/kg $CCl_4$ given orally after fasting for 24 hours.
$LD_{50}$-Oral dose of $CCl_4$ required for 50% lethality
[c]-SGOT levels were measured 48 hours following a 1.0 g/kg oral dose of $CCl_4$.

TABLE 19

EFFECT OF ALPHA-TOCOPHERYL SUCCINATE AND CHOLESTERYL SUCCINATE ADMINISTRATION ON SURVIVAL OF CDF$_1$ MICE FOLLOWING INJECTION OF $10^6$ L1210 LEUKEMIA CELLS

| Tocopherol or Succinate Analog Administered[a] | Survival Time (days) |
|---|---|
| Vehicle Control (Saline) | 6.0 ± 0.0 |
| Tocopheryl Succinate tris salt | 7.6 ± 0.6** |
| Cholesteryl Succinate, tris salt | 6.8 ± 0.4* |

[a]100 mg/kg, given i.p., immediately following tumor cell injection.
[b]Survival time was identical for succinate and vehicle treated groups.
*$p < 0.01$ as compared to succinate group, ± SD, n = 5.
**$p < 0.001$ as compared to succinate group, ± SD, n = 5.

TABLE 20

EFFECT OF IN VIVO ADMINISTRATION OF IONIZABLE CONGENERS OF AROMATIC AND ALIPHATIC ALCOHOLS ON $CCl_4$ - INDUCED HEPATOTOXICITY

| Analog Administered[a] | Serum Enzyme Levels[b] | |
|---|---|---|
| | AST ($10^3$ units/L) | ALT ($10^3$ units/L) |
| Tris Succinate (100 mg/kg, ip) (No $CCl_4$) | 0.11 ± 0.02 | 0.048 ± 0.005 |
| Tris Succinate (100 mg/kg, ip) | 11.22 ± 3.15 | 3.617 ± 0.858 |
| Cholesteryl Succinate Tris Salt (100 mg/kg, ip) | 0.41 ± 0.08** | 0.122 ± 0.034** |
| Cholesteryl Succinate Tris Salt (100 mg/kg, oral) | 12.51 ± 41.31 | 4.09 ± 1.191 |
| Alpha Tocopheryl Succinate Tris Salt (100 mg/kg, ip) | 1.86 ± 1.11* | 0.371 ± 0.246** |

[a]Given 20 hours prior to $CCl_4$ administration.
[b]Measured 48 hours following 1 g/kg oral dose of $CCl_4$.
*$p < 0.01$ as compared to Tris Succinate (with $CCl_4$) treatment, ± SD, n = 3–5. All animals were fasted 20 hours prior to $CCl_4$ administration.
**$p < 0.001$, ± SD, n = 4–5.

TABLE 21

EFFECT OF CHOLESTERYL SUCCINATE ADMINISTRATION ON LIVER ISCHEMIA/REPERFUSION-INDUCED LETHALITY

| Ischemia | Pretreatment[a] | % Survival |
|---|---|---|
| Global | Cholesterol (64 mg/kg, ip) + Tris Succinate (100 mg/kg, ip) | 10% (1/10) |
| Global | Cholesteryl Succinate Tris Salt (100 mg/kg, ip) | 90% (9/10) |
| Partial | None | 100% (3/3) |

[a]Global (total) or partial liver ischemia was induced 20 hours following pretreatment with the compounds listed above. After 60 minutes of ischemia, reperfusion was initiated and continued for 24 hrs.

TABLE 22

EFFECT OF CHOLESTERYL SUCCINATE ADMINISTRATION ON PARTIAL LIVER ISCHEMIA/REPERFUSION-INDUCED INJURY[a]

| Time of Treatment | Treatment | Serum Enzyme Levels (Units/L) | |
|---|---|---|---|
| | | AST | ALT |
| 20 hours prior to ischemia | Saline (100 mg/kg, ip) | 6450 ± 2903 | 2907 ± 1094 |
| 20 hours prior to ischemia | Cholesteryl succinate tris salt (100 mg/kg, ip) | 1800 ± 904* | 554 ± 213*** |
| During ischemia | Saline (100 mg/kg, ip) | 1960 ± 389 | 933 ± 238 |
| During ischemia | Cholesteryl succinate tris salt (100 mg/kg, ip) | 967 ± 68** | 387 ± 155* |

[a]Partial liver ischemia was induced in male Sprague Dawley rats (fed) for 60 min, followed by reperfusion for 24 hours, at which time serum was obtained for AST and ALT measurements. Sham operations (Without ischemia) resulted in AST and ALT values of 261 ± 37 and 58 ± 6 respectively.
*$p < 0.05$ as compared to saline vehicle control group, ± SD, n = 3–4.
**$p < 0.02$ as compared to saline vehicle control group, ± SD, n = 3–4.
***$p < 0.01$ as compared to saline vehicle control group, ± SD, n = 3–4.

TABLE 23

EFFECT OF CHOLESTERYL SUCCINATE ADMINISTRATION OF ACETAMINOPHEN (AP) - INDUCED HEPATOTOXICITY

| Analog Administered | Serum AST Level[a] (Units/L) | Serum ALT Level[a] (Units/L) |
|---|---|---|
| Tris Succinate (100 mg/kg, ip) (No AP) | 93 + 34 | 50 ± 7 |
| Tris Succinate (100 mg/kg, ip) (20 hrs prior to AP) | 2286 + 1190 | 623 + 339 |
| Cholesteryl Succinate (100 mg/kg, ip) Tris Salt (20 hrs prior to AP) | 785 ± 495* | 158 ± 77** |

[a]Measured 48 hours following a 2 g/kg oral dose of Acetaminophen.
*$p < 0.05$ as compared to Tris Succinate (20 hours prior) treatment, ±SD, n = 4–6. All rats were fed during the entire experiment.
**$p < 0.02$.

TABLE 24

EFFECT OF CHOLESTERYL SUCCINATE TRIS SALT (CS) ADMINISTRATION ON TETRAHYDROAMINO-ACRIDINE (THA) - INDUCED SIDE EFFECTS IN MALE SPRAGUE-DAWLEY RATS

| THA (mg/kg) | Change From Control | | | | | |
|---|---|---|---|---|---|---|
| | Tremors* | | Salivation* | | Survival* | |
| | Veh. | CS. | Veh. | CS. | Veh. | CS. |
| 30.0 | 3.0 ± 0.0 | 4.0 ± 0.0[a] | 2.2 ± 0.4 | 4.0 ± 0.0[a] | 100% | 40%[a] |

Control = vehicle (ip) + distilled water (oral dose). CS - cholesterol succinate tris salt (100 mg/kg, ip), Veh. - saline, ip. Tremor and salivation were rated on a 0 to 4 scale with 0 meaning no effect. CS and vehicle were given 20 hours prior to THA administration.
[a]$p < 0.001$ as compared to vehicle ±SD, n = 5.
*Measured 3–5 hrs. following oral dose of THA to fasted (20 hrs) rats.

TABLE 25

EFFECTS OF TOCOPHERYL SUCCINATE AND CHOLESTERYL SUCCINATE ADMINISTRATION ON PENTOBARBITONE (PB) SLEEPING TIME IN THE RAT

| Pretreatment[a] | Sleeping Time (min)[b] | Nutritional Status Prior to PB |
|---|---|---|
| Vehicle (olive oil) | 72 ± 14 | Fasted 24 hours |
| Alpha Tocopheryl Succinate (100 mg/kg, ip) | 86 ± 1 | |
| Cholesterol (64 mg/kg, ip) + Tris Succinate (59 mg/kg, ip) | 117 ± 30 | Fasted 24 hours |
| Cholesteryl Succinate Tris Salt (100 mg/kg, ip) | 148 ± 40 | |
| Cholesterol (64 mg/kg, ip) + Tris Succinate (59 mg/kg, ip) | 89 ± 1 | Fed |
| Cholesteryl Succinate Tris Salt (100 mg/kg, ip) | 102 ± 16 | |
| Vehicle (corn oil) | 120 + 9 | Fasted 24 hours |
| Metyrapone (100 mg/kg, ip) | 900 ± 120* | |

[a]Rats are pretreated, with the compounds listed, 20 hours prior to PB except metyrapone which was given 30 min prior to PB.
[b]Pentobarbitone administration (50 mg/kg, ip).
*$p < 0.001$ as compared to control, ±SEM, n = 3–5.

TABLE 26

EFFECT OF CHOLESTERYL SUCCINATE CHEMICAL FORM (FREE ACID OR TRIS SALT) ON ITS PROTECTIVE CAPACITY AGAINST $CCl_4$ HEPATOTOXICITY IN VIVO

| Analog Administered[a] | Serum AST Levels ($10^3$ units/L)[b] | |
|---|---|---|
| | 24 hrs | 48 hrs |
| Vehicle Control (olive oil) (with $CCl_4$) | 2.33 ± 0.35 | 4.39 ± .33 |
| Cholesteryl Succinate free acid (100 mg/kg, ip) | 1.84 ± 1.13 | 1.90 ± 2.64 |
| Cholesteryl Succinate, tris salt (100 mg/kg, ip) | 0.57 ± 0.38* | 0.19 + 0.07* |

[a]Given 20 hours prior to $CCl_4$ administration.
[b]Measured at the time intervals indicated following a 2 g/kg oral dose of $CCl_4$.
*$p < 0.001$ as compared to Vehicle Control (with $CCl_4$), $\bar{x} \pm SD$, n = 3–5.

TABLE 27

EFFECT OF TOCOPHERYL SUCCINATE CHEMICAL FORM (FREE ACID OR TRIS SALT) ON ITS PROTECTIVE CAPACITY AGAINST $CCl_4$ HEPATOTOXICITY IN VIVO

| Analog Administered[a] | Serum AST Levels ($10^3$ units/L)[b] | |
|---|---|---|
| | AST ($10^3$ units/L) | ALT ($10^3$ units/L) |
| Vehicle Control (olive oil) (with $CCl_4$) | 4.41 ± 2.05 | 1.95 ± 0.71 |
| Alpha Tocopheryl Succinate free acid (100 mg/kg, ip) | 2.06 ± 0.53 | 1.08 ± 0.23 |
| Alpha Tocopheryl Succinate tris salt (100 mg/kg, ip) | 0.79 ± 0.26* | 0.52 ± 0.16* |

[a]Given 20 hours prior to $CCl_4$ administration.
[b]Measured 48 hours following a 1 g/kg oral dose of $CCl_4$.
*$p < 0.01$ as compared to Vehicle Control and Tocopherol Succinate Free Acid treatments, $\bar{x} \pm SD$, n = 3–4.

TABLE 28

EFFECT OF THE DOSE OF CHOLESTERYL SUCCINATE TRIS SALT ON ITS PROTECTIVE CAPACITY AGAINST $CCl_4$ HEPATOTOXICITY IN VIVO

| Analog Administered[a] | Serum Enzyme Levels[b] | |
|---|---|---|
| | AST ($10^3$ units/L) | ALT ($10^3$ units/L) |
| Vehicle Control (saline) | 7.58 ± 2.10 | 3.16 ± 0.48 |
| Cholesteryl Succinate tris salt (200 mg/kg, ip) | 0.16 ± 0.08* | 0.03 ± 0.01* |
| Cholesteryl Succinate tris salt (100 mg/kg, ip) | 0.22 ± 0.06* | 0.04 ± 0.02* |
| Cholesteryl Succinate tris salt (50 mg/kg, ip) | 0.56 ± 0.35* | 0.16 ± 0.11* |

[a]Given 20 hours prior to $CCl_4$ administration.
[b]Measured 48 hours following 1 g/kg oral dose of $CCl_4$.
*$p < 0.001$ as compared to Vehicle Control (with $CCl_4$). ±SD, n = 3–5.

TABLE 29

EFFECT OF PRETREATMENT TIME ON CHOLESTERYL SUCCINATE TRIS SALT-MEDIATED PROTECTION AGAINST $CCl_4$ HEPATOTOXICITY IN VIVO

| Analog Administered[a] | Serum Enzyme Levels[b] | |
|---|---|---|
| | AST ($10^3$ units/L) | ALT ($10^3$ units/L) |
| Vehicle Control (Saline) | 6.72 ± 2.76 | 2.60 ± 1.52 |
| Cholesteryl Succinate tris salt (100 mg/kg, ip) (20 hours prior to $CCl_4$) | 0.12 ± 0.02* | 0.04 ± 0.01* |
| Cholesteryl Succinate tris salt (100 mg/kg, ip) (30 min prior to $CCl_4$) | 9.09 ± 4.38 | 2.12 ± 1.43 |
| Cholesteryl Succinate tris salt (100 mg/kg, ip) (immediately prior to $CCl_4$) | 6.69 ± 1.87 | 1.12 ± 1.38 |
| Cholesteryl Succinate tris salt (100 mg/kg, ip) (30 min after to $CCl_4$) | 7.87 ± 4.09 | 1.50 ± 0.79 |

[a]Measured 48 hours following 1 g/kg oral dose of $CCl_4$.
*$p < 0.001$ as compared to Vehicle control (with $CCl_4$), ±SD, n = 4–5.

TABLE 30

EFFECT OF IN VIVO ADMINISTRATION OF IONIZABLE CONGENERS OF AROMATIC AND ALIPHATIC ALCOHOLS ON $CCl_4$-INDUCED HEPATOTOXICITY

| Ionizable Congener Administered[a] | % Hepato-protection[b] | Protective Potency[c] |
|---|---|---|
| Vehicle Control (without $CCl_4$) | 100% | |
| Vehicle Control (with $CCl_4$) | 0% | |
| Tocopherol Derivatives | | |
| Alpha tocopheryl succinate tris salt | 80% | ++ |
| Sterol Derivatives | | |
| Cholesteryl succinate tris salt | 100% | ++++ |
| Cholesteryl 3-sulfate, sodium salt | 90% | +++ |
| Cholesteryl hydrogen phthalate | 100% | ++++ |
| Dihydrocholesterol sulfate, sodium salt | 100% | ++++ |
| Dihydrocholesterol succinate, tris salt | 100% | ++++ |
| Ergosterol sulfate, potassium salt | 86% | +++ |
| Ergosterol succinate, tris salt | 80% | +++ |
| Dehydroepiandosterone 3-succinate | 0% | 0 |
| Dehydroepiandosterane 3-sulfate | 4% | 0 |
| Hydrocortisone 21-succinate | 25% | 0 |
| Straight Chain Alcohol Derivatives | | |
| Lauryl sulfate, sodium salt | 26% | 0 |
| Palmityl succinate | 22% | 0 |
| Linoleyl succinate | 46% | + |
| Phytol succinate | 27% | 0 |
| Others | | |
| Retinoic acid (50 mg/kg, ip) | (−83%) | 0 |

[a]Given at a concentration of 100 mg/kg, ip., 20 hours prior to $CCl_4$ administration (except as noted).
[b]Measured 48 hours following a 1 g/kg oral dose of $CCl_4$. AST and ALT levels from experimental compounds were compared to vehicle controls to assess the % hepatoprotection.
[c]Protective potency was determined on a scale from 0 to 4, based on AST and ALT levels as compared to vehicle controls.

TABLE 31

EFFECT OF THE DOSE OF CHOLESTERYL SUCCINATE TRIS SALT ON ITS PROTECTIVE CAPACITY AGAINST $CCl_4$ HEPATOTOXICITY IN VIVO

| Analog Administered[a] | Serum Enzyme Levels[b] | |
|---|---|---|
| | AST ($10^3$ units/L) | ALT ($10^3$ units/L) |
| Vehicle Control (olive oil) (no $CCl_4$) | 0.12 ± 0.03 | 0.04 ± 0.01 |
| Vehicle Control (olive oil) (+$CCl_4$) | 3.57 ± 1.18 | 0.92 ± 0.14 |
| Cholesteryl Succinate tris salt (100 mg/kg, ip) | 0.10 ± 0.03* | 0.02 ± 0* |
| Cholesterol (100 mg/kg, ip) | 3.03 ± 0.84 | 1.16 ± 0.41 |
| Cholesterol acetate (100 mg/kg, ip) | 3.06 ± 1.06 | 0.96 ± 0.32 |

[a]Given 20 hours prior to $CCl_4$ administration.
[b]Measured 48 hours following 1 g/kg oral dose of $CCl_4$.
*$p < 0.001$ as compared to Vehicle Control (with $CCl_4$). ±SD, n = 3–5.

TABLE 32

EFFECT OF THE DOSE OF CHOLESTERYL SUCCINATE TRIS SALT ON ITS PROTECTIVE CAPACITY AGAINST $CCl_4$ HEPATOTOXICITY IN VIVO

| Analog Administered[a] | Serum AST Levels ($10^3$ units/L)[b] | | |
|---|---|---|---|
| | 24 hrs | 48 hrs | 72 hrs |
| Vehicle Control (polyethylene glycol 400) (no $CCl_4$) | .12 ± .02 | .11 ± .03 | .13 ± .02 |
| Vehicle Control (with $CCl_4$) | .99 ± .36 | 1.04 ± .10 | .26 ± .11 |
| Cholesteryl Succinate tris salt (100 mg/kg, ip) | .19 ± .10*** | .10 ± .02**** | .10 ± .02** |
| Alpha Tocopheryl Succinate (100 mg/kg, ip) | .38 ± .15* | .39 ± .22*** | .14 ± .06 |

TABLE 32-continued

EFFECT OF THE DOSE OF CHOLESTERYL SUCCINATE TRIS SALT ON ITS
PROTECTIVE CAPACITY
AGAINST $CCl_4$ HEPATOTOXICITY IN VIVO

| Analog Administered[a] | Serum AST Levels ($10^3$ units/L.)[b] | | |
|---|---|---|---|
| | 24 hrs | 48 hrs | 72 hrs |
| Cholesterol (100 mg/kg, ip) + Succinic acid (50 mg/kg, ip) | .86 ± .16 | 1.66 ± .50 | .30 ± .07 |

[a]Given 20 hours prior to $CCl_4$ administration.
[b]Measured at the time intervals indicated following a 2 g/kg oral dose of $CCl_4$.
*$p < 0.05$ as compared to Vehicle Control (with $CCl_4$), ±SD, n = 3–5.
**$p < 0.02$ as compared to Vehicle Control (with $CCl_4$), ±SD, n = 3–5.
***$p < 0.01$ as compared to Vehicle Control (with $CCl_4$), ±SD, n = 3–5.
****$p < 0.001$ as compared to Vehicle Control (with $CCl_4$), ±SD, n = 3–5.

TABLE 33

EFFECT OF IN VIVO ADMINISTRATION OF
IONIZABLE CONGENERS OF AROMATIC AND
ALIPHATIC ALCOHOLS ON $CCl_4$ - INDUCED
HEPATOTOXICITY

| Analog Administered[a] | Serum Enzyme Levels[b] | |
|---|---|---|
| | AST ($10^3$ units/L) | ALT ($10^3$ units/L) |
| Tris Succinate (100 mg/kg, ip) (No $CCl_4$) | 0.15 ± 5.02 | 0.058 ± .001 |
| Tris Succinate (100 mg/kg, ip) | 8.32 ± 2.65 | 2.135 ± .881 |
| Cholesteryl 3-Sulfate Sodium Salt (100 mg/kg, ip) | 0.86 ± 0.35** | 0.240 ± .133 |
| Palmityl Succinate Tris Salt (100 mg/kg, ip) | 6.54 ± 3.61 | 1.679 ± 0.883 |
| Palmityl Alcohol (100 mg/kg, ip) | 8.70 ± 3.00 | 1.840 ± 1.106 |
| Hydrocortisone 21-Succinate (100 mg/kg, ip) | 6.18 ± 3.15 | 1.596 ± 0.887 |

[a]Given 20 hours prior to $CCl_4$ administration.
[b]Measured 48 hours following 1 g/kg oral dose of $CCl_4$.
*$p < 0.01$ as compared to Control (with $CCl_4$), ± SD, n = 5.
**$p < 0.001$.

TABLE 34

EFFECT OF IN VIVO ADMINISTRATION OF
IONIZABLE CONGENERS OF AROMATIC AND
ALIPHATIC ALCOHOLS ON $CCl_4$ - INDUCED
HEPATOTOXICITY

| Analog Administered[a] | Serum Enzyme Levels[b] | |
|---|---|---|
| | AST ($10^3$ units/L) | ALT ($10^3$ units/L) |
| Vehicle Control (Polyethylene glycol 400, 4 ml/kg, ip) | 14.35 ± 2.98 | 4.08 ± 1.70 |
| Cholesteryl Succinate tris salt (100 mg/kg, ip) | 0.29 ± 0.22** | 0.07 ± 0.03** |
| Estrone sulfate, potassium salt (100 mg/kg, ip) | 4.19 ± 2.75* | 0.87 ± 0.59* |
| Dehydroepiandrosterane 3-sulfate, sodium salt (100 mg/kg, ip) | 13.85 ± 0.37 | 3.89 ± 0.81 |
| Cholesterol hydrogen phthalate (100 mg/kg, ip) | 0.30 ± 0.12** | 0.06 ± 0.03** |
| Dihydrocholesterol sulfate, sodium salt (100 mg/kg, ip) | 0.15 ± 0.07** | 0.03 ± 0.03** |

[a]Given 20 hours prior to $CCl_4$ administration.
[b]Measured 48 hours following 1 g/kg oral dose of $CCl_4$.
*$p < 0.01$ as compared to Vehicle control (with $CCl_4$), ± SD, n = 3–5.
**$p < 0.001$ as compared to Vehicle control (with $CCl_4$), ± SD, n = 3–5.

TABLE 35

EFFECT OF IN VIVO ADMINISTRATION OF
IONIZABLE CONGENERS OF AROMATIC AND
ALIPHATIC ALCOHOLS ON $CCl_4$ - INDUCED
HEPATOTOXICITY

| Analog Administered[a] | Serum Enzyme Levels[b] | |
|---|---|---|
| | AST ($10^3$ units/L) | ALT ($10^3$ units/L) |
| Vehicle Control (olive oil) | 8.35 ± 2.65 | 2.62 ± 0.70 |
| Cholesteryl Succinate tris salt (100 mg/kg, ip) | 0.22 ± 0.06*** | 0.04 ± 0.02*** |
| Dihydrocholesterol (80 mg/kg, ip) + Sodium sulfate (30 mg/kg, ip) | 6.63 ± 2.58 | 1.97 ± 0.59 |
| Dihydrocholesterol sulfate, sodium salt (100 mg/kg, ip) | 0.17 ± 0.04*** | 0.02 ± 0.01*** |
| Linoleyl succinate (100 mg/kg, ip) | 4.47 ± 2.21 | 1.44 ± 0.59* |
| Linoleyl alcohol (100 mg/kg, ip) | 15.60 ± 2.98** | 5.45 ± 1.10** |

[a]Given 20 hours prior to $CCl_4$ administration.
[b]Measured 48 hours following 1 g/kg oral dose of $CCl_4$.
*$p < 0.05$ as compared to Vehicle control (with $CCl_4$), ± SD, n = 3–5.
**$p < 0.01$ as compared to Vehicle control (with $CCl_4$), ± SD, n = 3–5.
***$p < 0.001$ as compared to Vehicle control (with $CCl_4$), ± SD, n = 3–5.

TABLE 36

EFFECT OF IN VIVO ADMINISTRATION OF
IONIZABLE CONGENERS OF AROMATIC AND
ALIPHATIC ALCOHOLS ON $CCl_4$ - INDUCED
HEPATOTOXICITY

| Analog Administered[a] | Serum Enzyme Levels[b] | |
|---|---|---|
| | AST ($10^3$ units/L) | ALT ($10^3$ units/L) |
| Vehicle Control (olive oil) | 4.74 ± .70 | 3.56 ± 0.41 |
| Dihydrocholesterol succinate | 0.44 ± 0.29* | 0.39 ± 0.40* |

[a]Given 20 hours prior to $CCl_4$ administration.
[b]Measured 48 hours following 1 g/kg oral dose of $CCl_4$.
*$p < 0.001$ as compared to Vehicle control (with $CCl_4$), ± SD, n = 3–4.

acid, or pharmaceutically acceptable salts, tris salts, ethers and esters thereof.

2. The method of claim 1 wherein said compound is in a water soluble form.

3. The method of claim 2 wherein said compound is a polyethylene glycol ester.

4. The method of claim 2 wherein said compound is a tris salt.

5. The method of claim 1 further comprising the step of administering said patient a dose of an anthracycline.

6. The method of claim 1 wherein said compound is tocopheryl succinate or pharmaceutically acceptable salts, tris salts, ethers and esters thereof.

7. The method of claim 6 wherein said tocopheryl succinate is provided as a tris salt or a polyethylene glycol ester.

8. The method of claim 1 wherein said compound is tocopheryloxybutyric acid or pharmaceutically acceptable salts, tris salts, ethers and esters thereof.

9. The method of claim 8 wherein said tocopheryloxybutyric acid is provided as a tris salt or a polyethylene glycol ester.

10. The method of claim 1 wherein said compound is selected from the group consisting of cholesteryl succinate, cholesteryloxybutyric acid or pharmaceutically acceptable salts, tris salts, ethers and esters thereof.

11. The method of claim 10 wherein said compound is provided as a tris salt or a polyethylene glycol ester.

* * * * *